US008685978B2

(12) United States Patent
Lee et al.

(10) Patent No.: US 8,685,978 B2
(45) Date of Patent: Apr. 1, 2014

(54) SPECTINAMIDES AS ANTI-TUBERCULOSIS AGENTS

(75) Inventors: Richard E. Lee, Cordova, TN (US); Jianjun Qi, Houston, TX (US); Julian G. Hurdle, Euless, TX (US); Bernd Meibohm, Germantown, TN (US); Vnr Pavan Kumar Vaddady, Memphis, TN (US); Rakesh, Cordova, TN (US); Jiuyu Liu, Bartlett, TN (US)

(73) Assignee: University of Tennessee Research Foundation, Knoxville, TN (US)

( * ) Notice: Subject to any disclaimer, the term of this patent is extended or adjusted under 35 U.S.C. 154(b) by 355 days.

(21) Appl. No.: 12/843,551

(22) Filed: Jul. 26, 2010

(65) Prior Publication Data

US 2011/0118272 A1 May 19, 2011

Related U.S. Application Data

(60) Provisional application No. 61/228,266, filed on Jul. 24, 2009.

(51) Int. Cl.
| | | |
|---|---|---|
| *A61K 31/501* | (2006.01) | |
| *A61K 31/4965* | (2006.01) | |
| *C07D 239/42* | (2006.01) | |
| *A61K 31/44* | (2006.01) | |
| *A61K 31/425* | (2006.01) | |
| *A61K 31/415* | (2006.01) | |
| *A61K 31/335* | (2006.01) | |

(52) U.S. Cl.
USPC ............ 514/252.01; 514/254.11; 514/255.05; 514/256; 514/338; 514/354; 514/370; 514/397; 514/452

(58) Field of Classification Search
None
See application file for complete search history.

(56) References Cited

U.S. PATENT DOCUMENTS

| 4,173,647 A | 11/1979 | Maier et al. |
| 4,465,848 A | 8/1984 | Thomas et al. |
| 5,628,984 A | 5/1997 | Boucher, Jr. |

FOREIGN PATENT DOCUMENTS

EP         0 079 125       5/1983

OTHER PUBLICATIONS

Stella et al (Prodrugs: Challenges and Rewards, Part 1, 2007).*
Werner et al (Antimicrob Agents Chemother 21:101-106, 1982).*
Written Opinion of the International Searching Authority for international application No. PCT/US10/43244 (Dec. 7, 2010).
International Search Report for international application No. PCT/US10/43244 (Dec. 7, 2010).

Hanessian et al., "Synthesis of 4-Amino-4-(S)-Dihydrospectinomycin", The Journal of Antibiotics (Tokyo), 34(3): 350-352 (1981).
PubChem CID23277625 (Dec. 6, 2007).
Thomas et al., Spectinomycin Modification III Spectinomycin Analogs With C-3'-Branched Chain Sugars, The Journal of Antibiotics (Tokyo), 38(2): 208-219 (1985).
Woitun et al., "Modification of Spectinomycin 2 Derivatives of 4-Dihydro-4-deoxy-4(R)-aminospectinomycin", The Journal of Antibiotics, 34(1): 22-27 (1981).
Borovinskaya et al., "A Steric Block in Translation Caused by the Antibiotic Spectinomycin," ACS Chemical Biology. vol. 2, No. 8 pp. 545-552 (2007).
Gruppo et al., "Rapid Microbiologic and Pharmacologic Evaluation of Experimental Compounds against *Mycobacterium tuberculosis*," Antimicrobial Agents and Chemotherapy. vol. 50, No. 4 pp. 1245-1250 (2006).
Sacchettini et al., "Drugs versus bugs: in pursuit of the persistant predator *Mycobacterium tuberculosis*," Nature Reviews: Microbiology. vol. 6, No. 1 pp. 41-52 (2008).
Spigelman, "New Tuberculosis Therapeutics: A Growing Pipeline," Journal of Infectious Disease. vol. 196, Suppl. 1, pp. S28-S34 (2007).
Thomas, R.C., and Fritzen, E.L., "Spectinomycin Modification. II. Spectinomycin C-3'-Modification via Diazoketone Intermediates," The Journal of Antibiotics. vol. 38, No. 2 pp. 197-207 (1985).
Thomas, R.C., and Fritzen, E.L., "Spectinomycin Modification. III. Spectinomycin Analogs With C-3'-Branced Chain Sugars," The Journal of Antibiotics. vol. 38, No. 2 pp. 208-219 (1985).
White et al., "Synthesis and In Vitro Antibacterial Properties of Alkylspectinomycin Analogs," The Journal of Antibiotics. vol. 36, No. 3 pp. 339-342 (1983).
Zurenko et al., "Trospectomycin, A Novel Spectinomycin Analogue: Antibacterial Activity and Preliminary Human Pharmacokinetics," Drugs Exp. Clin. Res. vol. 14, No. 6 pp. 403-409 (1988).
Berge et al., "Pharmaceutical Salts," Journal of Pharmaceutical Sciences. vol. 66, No. 1 pp. 1-19 (1977).
Budha et al., "Biopharmaceutics, Pharmacokinetics and Pharmacodynamics of Antituberculosis Drugs," Current Medicinal Chemistry. vol. 15, No. 8 pp. 809-825 (2008).
Budha et al., "Pharmacokinetically-Guided Lead Optimization of Nitrofuranylamide Anti-Tuberculosis Agents," The AAPS Journal. vol. 10, No. 1 pp. 157-165 (2008).
Centers for Disease Control, TB and HIV Coinfection. pp. 1-2 (2006).
Clinical and Laboratory Standards Institute, Methods for Dilution Antimicrobial Susceptibility Tests for Bacteria That Grow Aerobically; Approved Standard—Eighth Edition. vol. 29, No. 2 M07-A8, Wayne, Pennsylvania, United States of America. vii-xii, pp. 1, 65 and Abstract (2009).
Criswell et al., "Mutations Conferring Aminoglycoside and Spectinomycin Resistance in *Borrelia burgdorferi*," Antimicrobial Agents and Chemotherapy. vol. 50, No. 2 pp. 445-452 (2006).
Davies, B., and Morris, T., "Physiological Parameters in Laboratory Animals and Humans," Pharmaceutical Research. vol. 10, No. 7 pp. 1093-1095 (1993).
Eliopoulos, G.M., and Moellering, Jr., R.C., "Antimicrobial Combinations," in *In Antibiotics in Laboratory Medicine*, Williams and Wilkins, Co., Baltimore, Maryland, United States of America. pp. 432-449 (2000).

(Continued)

Primary Examiner — Craig Ricci
(74) Attorney, Agent, or Firm — Leon R. Yankwich; David G. O'Brien; Yankwich & Associates, P.C.

(57) ABSTRACT

Novel 3'-deoxy-3'-acylaminospectinomycin compounds are described. Also described are methods of using the 3'-deoxy-3-acylaminospectinomycin compounds and other spectinomycin analogs in treating tuberculosis and in treating microbial infections.

24 Claims, 6 Drawing Sheets

(56) References Cited

OTHER PUBLICATIONS

Galimand et al., "Spectinomycin Resistance in *Neisseria* spp. Due to Mutations in 16S rRNA," Antimicrobial Agents and Chemotherapy. vol. 44, No. 5 pp. 1365-1366 (2000).

Gismondo et al., "In Vitro Activity Against Aerobes and Anaerobes of Trospectomycin Versus Spectinomycin," Drugs Exp. Clin. Res. vol. 17, No. 2 pp. 101-104 (1991).

Greene, T.W., and Wuts, P.G.M., "Greene's Protective Groups in Organic Synthesis," 4th Edition; New York, John Wiley & Sons, Inc. pp. 748-753 (2007).

Holloway, "Spectinomycin," Medical Clinics of North America. vol. 66, No. 1 pp. 169-173 (1982).

Hurdle et al., "A microbiological assessment of novel nitrofuranylamides as anti-tuberculosis agents," Journal of Antimicrobial Chemotherapy. vol. 62, No. 5 pp. 1037-1045 (2008).

Maier et al., "Modification of Spectinomycin. 1. Synthesis of 4-Aminospectinomycins," The Journal of Antibiotics. vol. 34, No. 1 pp. 16-21 (1981).

Murray et al., "Ribosomes from an Oxazolidinone-Resistant Mutant Confer Resistance to Eperezolid in a *Staphylococcus aureus* Cell-Free Transcription-Translation Assay," Antimicrobial Agents and Chemotherapy. vol. 42, No. 4 pp. 947-950 (1998).

Nair et al., "The *rpsL* gene and streptomycin resistance in single and multiple drug-resistant strains of *Mycobacterium tuberculosis*," Molecular Microbiology. vol. 10, No. 3 pp. 521-527 (1993).

Novak et al., "Human Safety and Pharmacokinetics of a Single Intramuscular Dose of a Novel Spectinomycin Analog, Trospectomycin (U-63, 366F)," Antimicrobial Agents and Chemotherapy. vol. 34, No. 12 pp. 2342-2347 (1990).

O'Connor, M., and Dahlberg, A.E., "Isolation of Spectinomycin Resistance Mutations in the 16S rRNA of *Salmonella enterica* serovar Typhimurium and Expression in *Escherichia coli* and *Salmonella*," Current Microbiology. vol. 45, No. 6 pp. 429-433 (2002).

Odds, F. C., "Synergy, antagonism, and what the chequerboard puts between them," Journal of Antimicrobial Chemotherapy. vol. 52 p. 1 (2003).

Ramón-García et al., "Contribution of the Rv2333c efflux pump (the Stp protein) from *Mycobacterium tuberculosis* to intrinsic antibiotic resistance in *Mycobacterium bovis* BCG," Journal of Antimicrobial Chemotherapy. vol. 59, No. 3 pp. 544-547 (2007).

Woitun et al., "Modification of Spectinomycin. 2. Derivatives of 4-Dihydro-4-Deoxy-4($R$)-Aminospectinomycin," The Journal of Antibiotics. vol. 34, No. 1 pp. 22-27 (1981).

World Health Organization, Global tuberculosis control: surveillance, planning, financing. WHO report 2007. Geneva, World Health Organization (WHO/HTM/TB/2007.376) pp. 1-270.

\* cited by examiner

SEQUENCE LISTING

```
<160> NUMBER OF SEQ ID NOS: 4

<210> SEQ ID NO 1
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1
ccgtttgttt tgtcaggata                                              20

<210> SEQ ID NO 2
<211> LENGTH: 20
<212> TYPE: DNA
<213> ORGANISM: Artificial Sequence
<220> FEATURE:
<223> OTHER INFORMATION: Synthesized oligonucleotide

<400> SEQUENCE: 2
ttctcaaaca ccacacccca                                              20

<210> SEQ ID NO 3
<211> LENGTH: 22
<212> TYPE: DNA
<213> ORGANISM: Artificial Sequence
<220> FEATURE:
<223> OTHER INFORMATION: Synthesized oligonucleotide

<400> SEQUENCE: 3
ggcgtgccgg gtgacaaaaa gg                                           22

<210> SEQ ID NO 4
<211> LENGTH: 18
<212> TYPE: DNA
<213> ORGANISM: Artificial Sequence
<220> FEATURE:
<223> OTHER INFORMATION: Synthesized oligonucleotide

<400> SEQUENCE: 4
gaatccttcg taagccca                                                18
```

SPECTINAMIDES AS ANTI-TUBERCULOSIS AGENTS

CROSS-REFERENCE TO RELATED APPLICATION

The presently disclosed subject matter claims the benefit of U.S. Provisional Patent Application Ser. No. 61/228,266, filed Jul. 24, 2009, the disclosure of which is incorporated herein by reference in its entirety.

GOVERNMENT INTEREST

This presently disclosed subject matter was made with U.S. Government support under Grant No. R01AI062415 awarded by National Institutes of Health. Thus, the U.S. Government has certain rights in the presently disclosed subject matter.

TECHNICAL FIELD

The presently disclosed subject matter provides a family of novel spectinomycin analogs and describes the use of spectinomycin analogs in treating tuberculosis and other microbial infections.

ABBREVIATIONS

° C.=degrees Celsius
µg=microgram
µL=microliter
µM=micromolar
ATCC=American Type Culture Collection
CBz=carboxybenzyl
cfu=colony forming units
DIPEA=diisopropylethylamine
DMEM=Dulbecco's Modified Eagle's Medium
DMSO=dimethyl sulfoxide
ESI=electrospray ionization
EtOH ethanol
FBS=fetal bovine serum
FIC=fractional inhibitory concentration
HBTU=O-Benzotriazole-N,N,N',N'-tetramethyl-uronium-hexafluorophosphate
HIV=human immunodeficiency virus
hr=hours
IS=internal standard
IV=intravenous
kg=kilogram
LC=liquid chromatography
MDR=multidrug resistant
MeOH=methanol
mg=milligram
MIC=minimum inhibitory concentration
min=minutes
mL=milliliters
mmol=millimoles
MS=mass spectrometry
MW=molecular weight
rpm=revolutions-per-minute
PCR=polymerase chain reaction
Pd—C=palladium on carbon
Spc=Spectinomycin
Stp=Streptomycin
TB=tuberculosis
XDR=extensively drug resistant

BACKGROUND

*Mycobacterium tuberculosis*, the causative agent of tuberculosis, remains one of the world's most successful and deadly infectious diseases. It is estimated by the World Health Organization that more than three million active cases of tuberculosis occur worldwide annually leading to greater than one million deaths. See *World Health Organization*, WHO Report 2007. HIV infected individuals are more prone to become infected with and develop the active form of the disease, and as the HIV pandemic has spread across the globe this has significantly contributed to the recent increase in the number of tuberculosis cases observed globally. See *Centers for Disease Control*, TB and HIV Coinfection, 2006. The currently recommend treatment for tuberculosis is a four drug regime for a minimum of six months that includes rifampin, isoniazid, pyrazinamide and ethambutol. This lengthy and burdensome regime leads to non-compliance by patients. This in turn has produced an increasing number of multidrug resistant (MDR) and extensively drug resistant (XDR) strains found in the clinic, for which effective therapeutic options are severely limited.

Accordingly, there is a clear need to develop new therapeutics to treat tuberculosis. In particular there is a need for anti-tuberculosis therapeutics that have, for example, potent anti-tuberculosis activity in vivo; activity against drug resistant tuberculosis strains, including MDR and XDR strains; excellent safety/low toxicity; no drug interactions or antagonism with other drugs commonly used to treat tuberculosis or HIV; activity against latent or slow growing bacteria to help reduce treatment time; and long serum half-lives to reduce dosing frequency.

SUMMARY

The presently disclosed subject matter provides, in some embodiments, a compound of Formula (I):

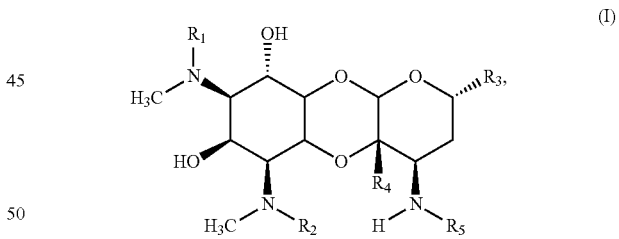

wherein:
$R_1$ and $R_2$ are each independently H, alkoxycarbonyl, or aralkoxycarbonyl;
$R_3$ is alkyl;
$R_4$ is H, hydroxy, alkyl, or alkoxy; and
$R_5$ is —C(=O)$R_6$, wherein $R_6$ is:
(a) selected from the group comprising —CH$_2$NHC(CH$_3$)$_3$, —CH$_2$CH(CH$_3$)$_2$, —CH(NH$_2$)CH(CH$_3$)CH$_2$CH$_3$, —CH(NH$_2$)CH(CH$_3$)$_2$, CH(CH$_2$C$_6$H$_5$)NHC(=O)CH$_2$NH$_2$, —CH$_2$CH$_2$NHC(=O)C$_6$H$_5$, and CH$_2$CH$_2$NHC(=O)CH$_2$C$_6$H$_5$; or
(b) selected from the group comprising heteroaryl, substituted heteroaryl, 2-substituted phenyl, 4-halo-substituted phenyl, —CH$_2$R$_7$, and —C(R$_8$)$_2$; wherein R$_7$ is selected from the group comprising aralkyl, substituted aralkyl, heteroaryl, substituted heteroaryl, and substituted phenyl, wherein said substituted phenyl is selected from the group comprising fluoro-substituted phenyl, alkyl-substituted phenyl, 2-substituted phenyl, 3-monosubstituted phenyl, 2,3-di-substituted phenyl, and di-substituted phenyl wherein two phenyl carbons are together substituted with an alkylene; and each $R_8$ is independently aryl or substituted aryl;

or a pharmaceutically acceptable salt or a prodrug thereof.

In some embodiments, $R_1$ and $R_2$ are each H. In some embodiments, $R_1$ and $R_2$ are each aralkoxycarbonyl selected from the group comprising benzyloxycarbonyl and benzyloxycarbonyl substituted by one or more halo, alkoxy, and nitro groups. In some embodiments, $R_1$ and $R_2$ are each benzyloxycarbonyl.

In some embodiments, $R_3$ is methyl or butyl. In some embodiments, $R_4$ is H, OH, methyl, or methoxy.

In some embodiments, $R_6$ is 4-fluorophenyl or 2-fluorophenyl. In some embodiments, $R_6$ is heteroaryl selected from the group comprising pyridyl, pyrimidinyl, pyridazinyl, oxazolyl, furanyl, triazolyl, triazinyl, benzofuranyl, thiophenyl, pyrrolyl, imidazoyl, thiazoyl, quinolinyl, isoquinolinyl, benzooxazolyl, and benzothiazolyl. In some embodiments, $R_6$ is —$C(R_8)_2$, wherein each $R_5$ is phenyl or substituted phenyl.

In some embodiments, the compound of Formula (I) is a compound of Formula (Ia):

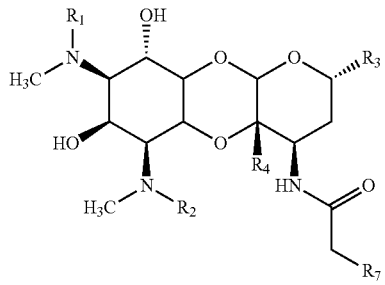

(Ia)

wherein:

$R_1$ and $R_2$ are each independently H, alkoxycarbonyl, or aralkoxycarbonyl;

$R_3$ is alkyl;

$R_4$ is H, hydroxy, alkyl, or alkoxy; and $R_7$ is selected from the group comprising aralkyl, substituted aralkyl, heteroaryl, substituted heteroaryl, and substituted phenyl, wherein said substituted phenyl is selected from the group comprising fluoro-substituted phenyl, alkyl-substituted phenyl, 2-substituted phenyl, 3-mono-substituted phenyl, 2,3-di-substituted phenyl, and di-substituted phenyl wherein two phenyl carbons are together substituted with an alkylene;

or a pharmaceutically acceptable salt or a prodrug thereof.

In some embodiments, $R_7$ is substituted phenyl selected from the group comprising 4-fluorophenyl, 4-methylphenyl, 3-methylphenyl, 3-methoxyphenyl, 2-methoxyphenyl, 3,4-methylenedioxyphenyl, and 2,3-difluorophenyl.

In some embodiments, $R_7$ is heteroaryl or substituted heteroaryl comprising a heteroaryl group selected from the group comprising pyridyl, triazolyl, triazinyl, pyrimidinyl, pyridazinyl, oxazolyl, furanyl, benzofuranyl, thiophenyl, pyrrolyl, imidazoyl, thiazoyl, quinolinyl, isoquinolinyl, benzooxazolyl, and benzothiazolyl.

In some embodiments, $R_7$ is substituted heteroaryl, wherein the heteroaryl is substituted with one or more of the group comprising $NH_2$, OH, alkylamino, arylamino, nitro, halo, alkyl, substituted alkyl, alkoxy, perhaloalkoxy, aralkyl, acyl, aryl, aryloxy, and substituted aryl. In some embodiments, $R_7$ is substituted heteroaryl, wherein the heteroaryl is substituted with one or more of the group comprising fluoro, chloro, bromo, methoxy, methyl, nitro, trifluoromethoxy, phenylamino, phenyl, and trifluoromethyl.

In some embodiments, $R_7$ is aralkyl or substituted aralkyl, wherein said aralkyl or substituted aralkyl comprises a heteroaryl or substituted heteroaryl group.

In some embodiments, $R_7$ comprises a nitrogen-containing heteroaryl group and the compound of Formula (Ia) has a structure of one of Formulas (Ib), (Ic), or (Id):

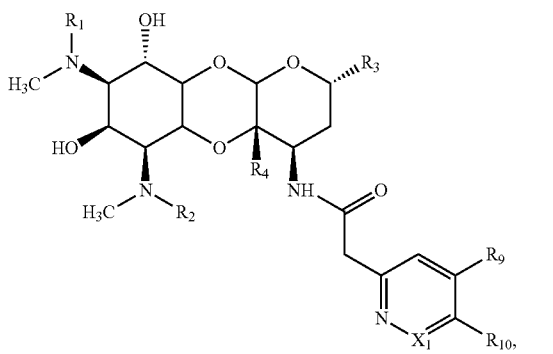

(Ib)

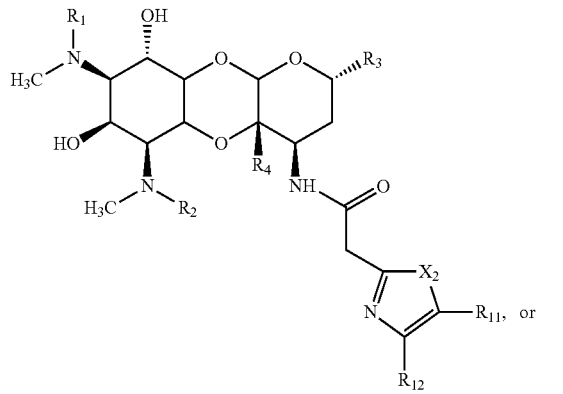

(Ic)

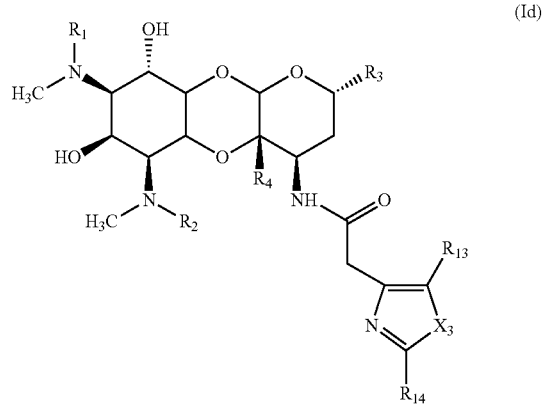

(Id)

wherein:

$R_1$ and $R_2$ are each independently H, alkoxycarbonyl, or aralkoxycarbonyl;

R<sub>3</sub> is alkyl;
R<sub>4</sub> is H, hydroxy, alkyl, or alkoxy;
X<sub>1</sub> is CH or N;
X<sub>2</sub> and X<sub>3</sub> are each O, S, or NH;
$R_9$, $R_{10}$, $R_{11}$, $R_{12}$, $R_{13}$, and $R_{14}$ are independently selected from the group comprising H, halo, hydroxy, nitro, $N(R_{15})_2$, alkyl, substituted alkyl, alkoxy, perhaloalkoxy, aralkyl, substituted aralkyl, aralkoxy, aryl, aryloxy, acyl and substituted aryl;
or wherein $R_9$ and $R_{10}$ together or $R_{11}$ and $R_{12}$ together are alkylene; and
each $R_{15}$ is independently selected from the group comprising H, alkyl, substituted alkyl, aralkyl, substituted aralkyl, aryl, and substituted aryl;
or a pharmaceutically acceptable salt or a prodrug thereof.

In some embodiments, the compound of Formula (I) is selected from the group comprising:

3'-dihydro-3'-deoxy-4(R)-(3-pyridin-3-yl)propionylamino spectinomycin;
3'-dihydro-3'-deoxy-4(R)-(pyridin-2-yl)acetylamino spectinomycin;
3'-dihydro-3'-deoxy-4(R)-4-fluorobenzoylamino spectinomycin;
3'-dihydro-3'-deoxy-4(R)-furan-2-carboxylicamino spectinomycin;
3'-dihydro-3'-deoxy-4(R)-(4-fluorophenyl)acetylamino spectinomycin;
3'-dihydro-3'-deoxy-4(R)-(pyridin-3-yl)acetylamino spectinomycin;
3'-dihydro-3'-deoxy-4(R)-pyridin-2-carboxylicamino spectinomycin;
3'-dihydro-3'-deoxy-4(R)-p-tolylacetylamino spectinomycin;
3'-dihydro-3'-deoxy-4(R)-(3-methoxy-phenyl)acetylamino spectinomycin;
3'-dihydro-3'-deoxy-4(R)-[3,4-(methylene dioxy)phenyl]acetylamino spectinomycin;
3'-dihydro-3'-deoxy-4(R)-m-tolylacetylamino spectinomycin;
3'-dihydro-3'-deoxy-4(R)-(pyridin-4-yl)acetylamino spectinomycin;
3'-dihydro-3'-deoxy-4(R)-(pyrimidin-2-yl)acetylamino spectinomycin;
3'-dihydro-3'-deoxy-4(R)-(thiazol-4-yl)acetylamino spectinomycin;
3'-dihydro-3'-deoxy-4(R)-(2-aminothiazol-4-yl)acetylamino spectino-mycin;
3'-dihydro-3'-deoxy-4(R)-(5-fluoropyridin-2-yl)acetylamino spectinomycin;
3'-dihydro-3'-deoxy-4(R)-(2,3-difluorophenyl)acetylamino spectinomycin;
3'-dihydro-3'-deoxy-4(R)-(2-methoxyphenyl)acetylamino spectinomycin;
3'-dihydro-3'-deoxy-4(R)-(pyridazin-3-yl)acetylamino spectinomycin;
3'-dihydro-3'-deoxy-4(R)-(pyrazine-2-yl)carboxylicamino spectinomycin;
3'-dihydro-3'-deoxy-4(R)-(benzooxazol-2-yl)acetylamino spectinomycin;
3'-dihydro-3'-deoxy-4(R)-(1H-imidazol-4-yl)acetylamino spectinomycin;
3'-dihydro-3'-deoxy-4(R)-[3(R)-amino-3-(4-fluorophenyl)]propanoylamino spectinomycin;
3'-dihydro-3'-deoxy-4(R)-(thiazol-2-yl)acetylamino spectinomycin;
3'-dihydro-3'-deoxy-4(R)-(5-nitropyridin-2-yl)acetylamino spectinomycin;
3'-dihydro-3'-deoxy-4(R)-(benzothiazol-2-yl)acetylamino spectinomycin;
3'-dihydro-3'-deoxy-4(R)-(2-fluorobenzene-1-yl)carboxylicamino spectinomycin;
3'-dihydro-3'-deoxy-4(R)-(2,2-diphenyl)acetylamino spectinomycin;
3'-dihydro-3'-deoxy-4(R)-(5-bromopyridin-2-yl)acetylamino spectino-mycin;
3'-dihydro-3'-deoxy-4(R)-(2-phenylthiazol-4-yl)acetylamino spectinomycin;
3'-dihydro-3'-deoxy-4(R)-(pyridin-2-yl)propanoylamino spectinomycin;
3'-dihydro-3'-deoxy-4(R)-(5-phenylpyridin-2-yl)acetylamino spectinomycin;
3'-dihydro-3'-deoxy-4(R)-(2-(phenylamino)thiazol-4-yl)acetylamino spectinomycin;
3'-Dihydro-3'-deoxy-4(R)-(5-(4-chlorophenyl)pyridin-2-yl)acetylamino spectinomycin;
3'-Dihydro-3'-deoxy-4(R)-(quinoline-8-yl)carbonylamino spectinomycin;
3'-Dihydro-3'-deoxy-4(R)-2-(1-benzyl-1H-1,2,3-triazol-4-yl)acetylamino spectinomycin;
3'-Dihydro-3'-deoxy-4(R)-(2-((4-fluorophenyl)amino)thiazol-4-yl)acetylamino spectinomycin;
3'-Dihydro-3'-deoxy-4(R)-(2-((3-fluorophenyl)amino)thiazol-4-yl)acetylamino spectinomycin;
3'-Dihydro-3'-deoxy-4(R)-(2-((4-(trifluoromethoxy)phenyl)amino)thiazol-4-yl)acetylamino spectinomycin;
3'-Dihydro-3'-deoxy-4(R)-(2-((4-(trifluoromethyl)phenyl)amino)thiazol-4-yl)acetylamino spectinomycin;
3'-Dihydro-3'-deoxy-4(R)-(5-(4-fluorophenyl)pyridin-2-yl)acetylamino spectinomycin;
3'-Dihydro-3'-deoxy-4(R)-(5-(3-methoxyphenyl)pyridin-2-yl)acetylamino spectinomycin;
3'-Dihydro-3'-deoxy-4(R)-(4-chloropyridin-2-yl)acetylamino spectinomycin;
3'-dihydro-3'-deoxy-4(R)-(tert-butylamino)acetylamino spectinomycin;
3'-dihydro-3'-deoxy-4(R)-(3-methyl)butanoylamino spectinomycin;
3'-dihydro-3'-deoxy-4(R)-[(2S,3S)-2-amino-3-methyl]pentanoylamino spectinomycin;
3'-dihydro-3'-deoxy-4(R)-[2(S)-amino-3-methyl]butanoylamino spectinomycin;
3'-dihydro-3'-deoxy-4(R)-[(S)-(2-aminoacetamido)-3-phenyl]propanoyl-amino spectinomycin;
3'-dihydro-3'-deoxy-4(R)-3-benzamido propanoylamino spectinomycin; and
3'-dihydro-3'-deoxy-4(R)-3-(2-phenylacetamido)propanoylamino spectinomycin;
or a pharmaceutically acceptable salt or prodrug thereof.

In some embodiments, the compound is a pharmaceutically acceptable salt. In some embodiments, the compound is a hydrochloride or hydrobromide salt.

In some embodiments, the presently disclosed subject matter provides a pharmaceutical formulation comprising: (a) a compound of Formula (I):

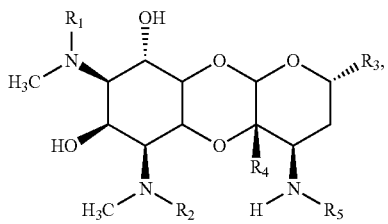

wherein:

$R_1$ and $R_2$ are each independently H, alkoxycarbonyl, or aralkoxycarbonyl;

$R_3$ is alkyl;

$R_4$ is H, hydroxy, alkyl, or alkoxy; and $R_5$ is —C(=O)$R_6$, wherein $R_6$ is:

(i) selected from the group comprising —CH$_2$NHC(CH$_3$)$_3$, —CH$_2$CH(CH$_3$)$_2$, —CH(NH$_2$)CH(CH$_3$)CH$_2$CH$_3$, —CH(NH$_2$)CH(CH$_3$)$_2$, —CH(CH$_2$C$_6$H$_5$)NHC(=O)CH$_2$NH$_2$, —CH$_2$CH$_2$NHC(=O)C$_6$H$_5$, and —CH$_2$CH$_2$NHC(=O)CH$_2$C$_6$H$_5$; or (ii) selected from the group comprising heteroaryl, substituted heteroaryl, 2-substituted phenyl, 4-halo-substituted phenyl, —CH$_2$R$_7$, and —C(R$_8$)$_2$; wherein $R_7$ is selected from the group comprising aralkyl, substituted aralkyl, heteroaryl, substituted heteroaryl, and substituted phenyl, wherein said substituted phenyl is selected from the group comprising fluoro-substituted phenyl, alkyl-substituted phenyl, 2-substituted phenyl, 3-mono-substituted phenyl, 2,3-di-substituted phenyl, and di-substituted phenyl wherein two phenyl carbons are together substituted with an alkylene; and each $R_8$ is independently aryl or substituted aryl;

or a pharmaceutically acceptable salt or a prodrug thereof; and (b) a pharmaceutically acceptable carrier.

In some embodiments, the pharmaceutically acceptable carrier is pharmaceutically acceptable in humans. In some embodiments, the pharmaceutical formulation further comprises an additional therapeutic and/or antibacterial compound. In some embodiments, the additional antibacterial compound is an anti-tuberculosis compound. In some embodiments, the additional antibacterial compound is selected from the group comprising isoniazid, ethambutol, rifampicin, kanamycin, capreomycin, linezolid, and streptomycin. In some embodiments, the pharmaceutical formulation is for oral or topical administration.

In some embodiments, the presently disclosed subject matter provides a method of treating a bacterial infection in a subject in need of treatment thereof, the method comprising administering to the subject an effective amount of a compound of Formula (I):

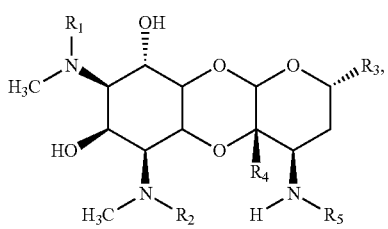

wherein:

$R_1$ and $R_2$ are each independently H, alkoxycarbonyl, or aralkoxycarbonyl;

$R_3$ is alkyl;

$R_4$ is H, hydroxy, alkyl, or alkoxy; and $R_5$ is —C(=O)$R_6$, wherein $R_6$ is:

(a) selected from the group comprising —CH$_2$NHC(CH$_3$)$_3$, —CH$_2$CH(CH$_3$)$_2$, —CH(NH$_2$)CH(CH$_3$)CH$_2$CH$_3$, —CH(NH$_2$)CH(CH$_3$)$_2$, —CH(CH$_2$C$_6$H$_5$)NHC(=O)CH$_2$NH$_2$, —CH$_2$CH$_2$NHC(=O)C$_6$H$_5$, and —CH$_2$CH$_2$NHC(=O)CH$_2$C$_6$H$_5$; or (b) selected from the group comprising heteroaryl, substituted heteroaryl, 2-substituted phenyl, 4-halo-substituted phenyl, —CH$_2$R$_7$, and —C(R$_8$)$_2$; wherein $R_7$ is selected from the group comprising aralkyl, substituted aralkyl, heteroaryl, substituted heteroaryl, and substituted phenyl, wherein said substituted phenyl is selected from the group comprising fluoro-substituted phenyl, alkyl-substituted phenyl, 2-substituted phenyl, 3-mono-substituted phenyl, 2,3-di-substituted phenyl, and di-substituted phenyl wherein two phenyl carbons are together substituted with an alkylene; and each $R_8$ is independently aryl or substituted aryl;

or a pharmaceutically acceptable salt or a prodrug thereof.

In some embodiments, $R_1$ and $R_2$ are each H. In some embodiments, $R_3$ is methyl or butyl. In some embodiments, $R_4$ is H, OH, methyl, or methoxy.

In some embodiments, $R_6$ is 4-fluorophenyl. In some embodiments, $R_6$ is heteroaryl selected from the group comprising pyridyl, triazolyl, triazinyl, pyrimidinyl, pyridazinyl, oxazolyl, furanyl, benzofuranyl, thiophenyl, pyrrolyl, imidazoyl, thiazoyl, quinolinyl, isoquinolinyl, benzooxazolyl, and benzothiazolyl.

In some embodiments, the compound of Formula (I) is a compound of Formula (Ia):

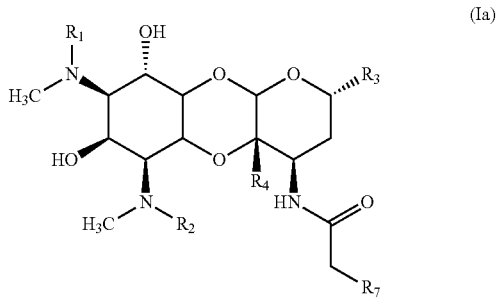

wherein:

$R_1$ and $R_2$ are each independently H, alkoxycarbonyl, or aralkoxycarbonyl;

$R_3$ is alkyl;

$R_4$ is H, hydroxy, alkyl, or alkoxy; and $R_7$ is selected from the group comprising aralkyl, substituted aralkyl, heteroaryl, substituted heteroaryl, and substituted phenyl, wherein said substituted phenyl is selected from the group comprising fluoro-substituted phenyl, alkyl-substituted phenyl, 2-substituted phenyl, 3-mono-substituted phenyl, 2,3-di-substituted phenyl, and di-substituted phenyl wherein two phenyl carbons are together substituted with an alkylene;

or a pharmaceutically acceptable salt or a prodrug thereof.

In some embodiments, $R_7$ is substituted phenyl selected from the group comprising 4-fluorophenyl, 4-methylphenyl, 3-methylphenyl, 3-methoxyphenyl, 2-methoxyphenyl, 3,4- methylenedioxyphenyl, and 2,3-difluorophenyl. In some embodiments, $R_7$ is heteroaryl or substituted heteroaryl comprising a heteroaryl group selected from the group comprising pyridyl, triazolyl, triazinyl, pyrimidinyl, pyridazinyl, oxazolyl, furanyl, benzofuranyl, thiophenyl, pyrrolyl, imidazoyl, thiazoyl, quinolinyl, isoquinolinyl, benzooxazolyl, and benzothiazolyl.

In some embodiments, $R_7$ is substituted heteroaryl, wherein the heteroaryl is substituted with one or more of the group comprising $NH_2$, OH, alkylamino, arylamino, nitro, halo, alkyl, substituted alkyl, alkoxy, perhaloalkoxy, aralkyl, acyl, aryl, aryloxy, and substituted aryl. In some embodiments, $R_7$ is substituted heteroaryl, wherein the heteroaryl is substituted with one or more of the group comprising fluoro, chloro, bromo, methoxy, methyl, nitro, trifluoromethoxy, phenylamino, phenyl, and trifluoromethyl.

In some embodiments, $R_7$ is aralkyl or substituted aralkyl, wherein said aralkyl or substituted aralkyl comprises a heteroaryl or substituted heteroaryl group.

In some embodiments, $R_7$ comprises a nitrogen-containing heteroaryl group and the compound of Formula (Ia) has a structure of one of Formulas (Ib), (Ic), or (Id):

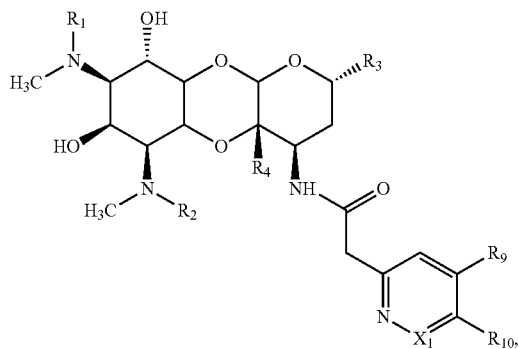

(Ib)

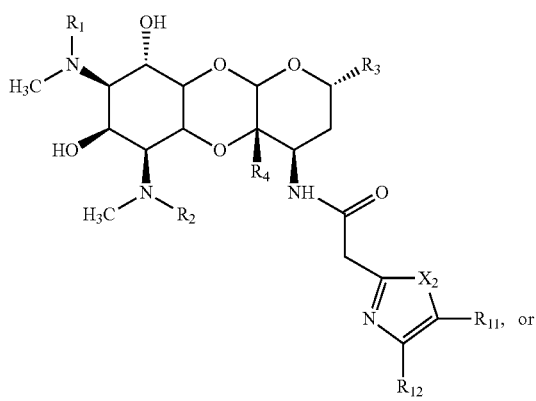

(Ic)

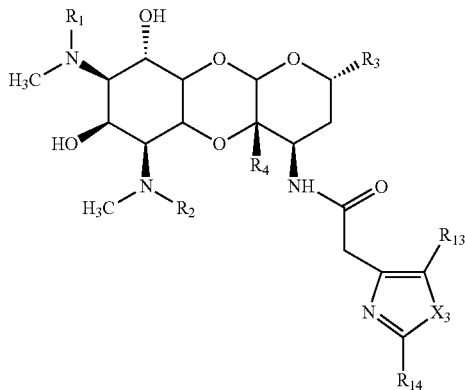

(Id)

wherein:
$R_1$ and $R_2$ are each independently H, alkoxycarbonyl, or aralkoxycarbonyl;
$R_3$ is alkyl;
$R_4$ is H, hydroxy, alkyl, or alkoxy;
$X_1$ is CH or N;
$X_2$ and $X_3$ are each O, S, or NH;
$R_9$, $R_{10}$, $R_{11}$, $R_{12}$, $R_{13}$, and $R_{14}$ are independently selected from the group comprising H, halo, hydroxy, nitro, $N(R_{15})_2$, alkyl, substituted alkyl, alkoxy, perhaloalkoxy, aralkyl, substituted aralkyl, aralkoxy, aryl, aryloxy, acyl and substituted aryl;
or wherein $R_9$ and $R_{10}$ together or $R_{11}$ and $R_{12}$ together are alkylene; and
each $R_{15}$ is independently selected from the group comprising H, alkyl, substituted alkyl, aralkyl, substituted aralkyl, aryl, and substituted aryl;
or a pharmaceutically acceptable salt or a prodrug thereof.

In some embodiments, the compound is selected from the group comprising:
3'-dihydro-3'-deoxy-4(R)-(3-pyridin-3-yl)propionylamino spectinomycin;
3'-dihydro-3'-deoxy-4(R)-(pyridin-2-yl)acetylamino spectinomycin;
3'-dihydro-3'-deoxy-4(R)-4-fluorobenzoylamino spectinomycin;
3'-dihydro-3'-deoxy-4(R)-furan-2-carboxylicamino spectinomycin;
3'-dihydro-3'-deoxy-4(R)-(4-fluorophenyl)acetylamino spectinomycin;
3'-dihydro-3'-deoxy-4(R)-(pyridin-3-yl)acetylamino spectinomycin;
3'-dihydro-3'-deoxy-4(R)-pyridin-2-carboxylicamino spectinomycin;
3'-dihydro-3'-deoxy-4(R)-p-tolylacetylamino spectinomycin;
3'-dihydro-3'-deoxy-4(R)-(3-methoxy-phenyl)acetylamino spectinomycin;
3'-dihydro-3'-deoxy-4(R)-[3,4-(methylene dioxy)phenyl]acetylamino spectinomycin;
3'-dihydro-3'-deoxy-4(R)-m-tolylacetylamino spectinomycin;
3'-dihydro-3'-deoxy-4(R)-(pyridin-4-yl)acetylamino spectinomycin;
3'-dihydro-3'-deoxy-4(R)-(pyrimidin-2-yl)acetylamino spectinomycin;
3'-dihydro-3'-deoxy-4(R)-(thiazol-4-yl)acetylamino spectinomycin;

3'-dihydro-3'-deoxy-4(R)-(2-aminothiazol-4-yl)acetylamino spectino-mycin;
3'-dihydro-3'-deoxy-4(R)-(5-fluoropyridin-2-yl)acetylamino spectinomycin;
3'-dihydro-3'-deoxy-4(R)-(2,3-difluorophenyl)acetylamino spectinomycin;
3'-dihydro-3'-deoxy-4(R)-(2-methoxyphenyl)acetylamino spectinomycin;
3'-dihydro-3'-deoxy-4(R)-(pyridazin-3-yl)acetylamino spectinomycin;
3'-dihydro-3'-deoxy-4(R)-(benzooxazol-2-yl)acetylamino spectinomycin;
3'-dihydro-3'-deoxy-4(R)-(1H-imidazol-4-yl)acetylamino spectinomycin;
3'-dihydro-3'-deoxy-4(R)-[3(R)-amino-3-(4-fluorophenyl)]propanoylamino spectinomycin;
3'-dihydro-3'-deoxy-4(R)-(thiazol-2-yl)acetylamino spectinomycin;
3'-dihydro-3'-deoxy-4(R)-(5-nitropyridin-2-yl)acetylamino spectinomycin;
3'-dihydro-3'-deoxy-4(R)-(benzothiazol-2-yl)acetylamino spectinomycin;
3'-dihydro-3'-deoxy-4(R)-(5-bromopyridin-2-yl)acetylamino spectino-mycin;
3'-dihydro-3'-deoxy-4(R)-(2-phenylthiazol-4-yl)acetylamino spectinomycin;
3'-dihydro-3'-deoxy-4(R)-(pyridin-2-yl)propanoylamino spectinomycin;
3'-dihydro-3'-deoxy-4(R)-(5-phenylpyridin-2-yl)acetylamino spectino-mycin;
3'-dihydro-3'-deoxy-4(R)-(2-(phenylamino)thiazol-4-yl)acetylamino spectinomycin;
3'-Dihydro-3'-deoxy-4(R)-(5-(4-chlorophenyl)pyridin-2-yl)acetylamino spectinomycin;
3'-Dihydro-3'-deoxy-4(R)-(quinoline-8-yl)carbonylamino spectinomycin;
3'-Dihydro-3'-deoxy-4(R)-2-(1-benzyl-1H-1,2,3-triazol-4-yl)acetylamino spectinomycin;
3'-Dihydro-3'-deoxy-4(R)-(2-((4-fluorophenyl)amino)thiazol-4-yl)acetylamino spectinomycin;
3'-Dihydro-3'-deoxy-4(R)-(2-((3-fluorophenyl)amino)thiazol-4-yl)acetylamino spectinomycin;
3'-Dihydro-3'-deoxy-4(R)-(2-((4-(trifluoromethoxy)phenyl)amino)thiazol-4-yl)acetylamino spectinomycin;
3'-Dihydro-3'-deoxy-4(R)-(2-((4-(trifluoromethyl)phenyl)amino)thiazol-4-yl)acetylamino spectinomycin;
3'-Dihydro-3'-deoxy-4(R)-(5-(4-fluorophenyl)pyridin-2-yl)acetylamino spectinomycin;
3'-Dihydro-3'-deoxy-4(R)-(5-(3-methoxyphenyl)pyridin-2-yl)acetylamino spectinomycin;
3'-Dihydro-3'-deoxy-4(R)-(4-chloropyridin-2-yl)acetylamino spectinomycin;
3'-dihydro-3'-deoxy-4(R)-(tert-butylamino)acetylamino spectinomycin;
3'-dihydro-3'-deoxy-4(R)-(3-methyl)butanoylamino spectinomycin;
3'-dihydro-3'-deoxy-4(R)-[(2S,3S)-2-amino-3-methyl]pentanoylamino spectinomycin; and
3'-dihydro-3'-deoxy-4(R)-[2(S)-amino-3-methyl]butanoylamino spectinomycin;
or a pharmaceutically acceptable salt or prodrug thereof.

In some embodiments, the compound is administered orally or topically. In some embodiments, an additional therapeutic compound is administered to the subject prior to, after, or during administration of the compound of Formula (I).

In some embodiments, the infection is an infection of a gram-positive bacterium. In some embodiments, the infection is selected from a mycobacterial infection, a *Bacillus anthracis* infection, a *Enterococcus faecalis* infection, and a *Streptococcus pneumoniae* infection.

In some embodiments, the infection is a *Bacillus anthracis* infection and the compound of Formula (I) is 3'-dihydro-3'-deoxy-4(R)-(pyridin-3-yl)acetylamino spectinomycin; 3'-dihydro-3'-deoxy-4(R)-(thiazol-4-yl)acetylamino spectinomycin; or 3'-dihydro-3'-deoxy-4(R)-(2-aminothiazol-4-yl)acetylamino spectinomycin; or a pharmaceutically acceptable salt or prodrug thereof.

In some embodiments, the infection is a *Streptococcus pneumoniae* infection and the compound of Formula (I) is selected from the group comprising: 3'-dihydro-3'-deoxy-4(R)-(pyridin-2-yl)acetylamino spectinomycin; 3'-dihydro-3'-deoxy-4(R)-(benzooxazol-2-yl)acetylamino spectinomycin; 3'-dihydro-3'-deoxy-4(R)-(1H-imidazol-4-yl)acetylamino spectinomycin; 3'-dihydro-3'-deoxy-4(R)-[3(R)-amino-3-(4-fluorophenyl)]propanoylamino spectinomycin; 3'-dihydro-3'-deoxy-4(R)-(thiazol-2-yl)acetylamino spectinomycin; 3'-dihydro-3'-deoxy-4(R)-(5-nitropyridin-2-yl)acetylamino spectinomycin; 3'-dihydro-3'-deoxy-4(R)-(benzothiazol-2-yl)acetylamino spectinomycin; 3'-dihydro-3'-deoxy-4(R)-(pyrimidin-2-yl)acetylamino spectinomycin; 3'-dihydro-3'-deoxy-4(R)-(5-bromopyridin-2-yl)acetylamino spectinomycin; 3'-dihydro-3'-deoxy-4(R)-(2-phenylthiazol-4-yl)acetylamino spectinomycin; 3'-dihydro-3'-deoxy-4(R)-(pyridin-2-yl)propanoylamino spectinomycin; 3'-dihydro-3'-deoxy-4(R)-(5-phenylpyridin-2-yl)acetylamino spectinomycin; 3'-dihydro-3'-deoxy-4(R)-(2-(phenylamino)-thiazol-4-yl)acetylamino spectinomycin; 3'-dihydro-3'-deoxy-4(R)-(thiazol-4-yl)acetylamino spectinomycin; 3'-dihydro-3'-deoxy-4(R)-(5-fluoropyridin-2-yl)acetylamino spectinomycin; 3'-dihydro-3'-deoxy-4(R)-(2,3-difluorophenyl)-acetylamino spectinomycin; 3'-Dihydro-3'-deoxy-4(R)-(5-(4-chlorophenyl)-pyridin-2-yl)acetylamino spectinomycin; 3'-Dihydro-3'-deoxy-4(R)-2-(1-benzyl-1H-1,2,3-triazol-4-yl)acetylamino spectinomycin; 3'-Dihydro-3'-deoxy-4(R)-(2-((4-fluorophenyl)amino)thiazol-4-yl)acetylamino spectinomycin; 3'-Dihydro-3'-deoxy-4(R)-(2-((3-fluorophenyl)amino)thiazol-4-yl)acetylamino spectinomycin; 3'-Dihydro-3'-deoxy-4(R)-(2-((4-(trifluoromethoxy)phenyl)-amino)thiazol-4-yl)acetylamino spectinomycin; 3'-Dihydro-3'-deoxy-4(R)-(2-((4-(trifluoro-methyl)phenyl)-amino)thiazol-4-yl)acetylamino spectinomycin; 3'-Dihydro-3'-deoxy-4(R)-(5-(4-fluorophenyl)pyridin-2-yl)acetylamino spectinomycin; 3'-Dihydro-3'-deoxy-4(R)-(5-(3-methoxyphenyl)pyridin-2-yl)acetylamino spec-tinomycin; and 3'-Dihydro-3'-deoxy-4(R)-(4-chloropyridin-2-yl)acetylamino spectinomycin; or a pharmaceutically acceptable salt or prodrug thereof.

In some embodiments, the infection is a *Enterococcus faecalis* infection and the compound of Formula (I) is selected from the group comprising: 3'-dihydro-3'-deoxy-4(R)-(5-fluoropyridin-2-yl)acetylamino spectinomycin; 3'-dihydro-3'-deoxy-4(R)-(benzothiazol-2-yl)acetylamino spectinomycin; 3'-dihydro-3'-deoxy-4(R)-(5-phenylpyridin-2-yl)acetylamino spec-tinomycin; 3'-Dihydro-3'-deoxy-4(R)-(5-(4-chlorophenyl)pyridin-2-yl)acetylamino spectino-mycin; 3'-Dihydro-3'-deoxy-4(R)-2-(1-benzyl-1H-1,2,3-triazol-4-yl)acetylamino spectinomycin; 3'-Dihydro-3'-deoxy-4(R)-(2-((4-fluorophenyl)amino)thiazol-4-yl)acetylamino spectinomycin; 3'-Dihydro-3'-deoxy-4(R)-(2-((3-fluorophenyl)-amino)thiazol-4-yl)acetylamino spectinomycin; 3'-Dihydro-3'-deoxy-4(R)-(2-((4-(trifluoromethoxy)phenyl)amino) thiazol-4-yl)acetylamino spectinomycin; 3'-Dihydro-3'-deoxy-4(R)-(2-((4-(trifluoromethyl)phenyl)-amino)thiazol-4-yl)acetyl-amino spectinomycin; 3'-Dihydro-3'-deoxy-4

(R)-(5-(4-fluorophenyl)pyridin-2-yl)acetylamino spectinomycin; and 3'-Dihydro-3'-deoxy-4(R)-(5-(3-methoxyphenyl)pyridin-2-yl)acetylamino spectinomycin; or a pharmaceutically acceptable salt or prodrug thereof.

In some embodiments, the infection is a *Mycobacterium tuberculosis* infection and the compound of Formula (I) is selected from the group comprising: 3'-dihydro-3'-deoxy-4 (R)-(pyridin-2-yl)acetylamino spectinomycin; 3'-dihydro-3'-deoxy-4(R)-(4-fluorophenyl)-acetylamino spectinomycin; 3'-dihydro-3'-deoxy-4(R)-(pyridin-3-yl)acetylamino spectinomycin; 3'-dihydro-3'-deoxy-4(R)-p-tolylacetylamino spectinomycin; 3'-dihydro-3'-deoxy-4(R)-(3-methoxy-phenyl)acetylamino spectinomycin; 3'-dihydro-3'-deoxy-4(R)-(thiazol-4-yl)acetylamino spectino-mycin; 3'-dihydro-3'-deoxy-4(R)-(2-aminothiazol-4-yl)acetylamino spectinomycin; 3'-dihydro-3'-deoxy-4(R)-(5-fluoropyridin-2-yl)acetylamino spectino-mycin; 3'-dihydro-3'-deoxy-4(R)-(1H-imidazol-4-yl)acetylamino spectinomycin; 3'-dihydro-3'-deoxy-4(R)-(benzooxazol-2-yl)acetylamino spectinomycin; 3'-dihydro-3'-deoxy-4(R)-(thiazol-2-yl)acetylamino spectinomycin; 3'-dihydro-3'-deoxy-4(R)-(5-nitropyridin-2-yl)acetylamino spectinomycin; 3'-dihydro-3'-deoxy-4(R)-(benzothiazol-2-yl)acetylamino spectinomycin; 3'-dihydro-3'-deoxy-4(R)-(5-bromopyridin-2-yl)acetylamino spectinomycin; 3'-dihydro-3'-deoxy-4(R)-(5-phenylpyridin-2-yl)acetylamino spectinomycin; 3'-dihydro-3'-deoxy-4(R)-(2-phenylamino)thiazol-4-yl)acetylamino spectinomycin; 3'-Dihydro-3'-deoxy-4(R)-(5-(4-chlorophenyl)pyridin-2-yl) acetylamino spectinomycin; 3'-Dihydro-3'-deoxy-4(R)-(2-((4-fluorophenyl)amino)thiazol-4-yl)acetylamino spectinomycin; 3'-Dihydro-3'-deoxy-4(R)-(2-((3-fluorophenyl) amino)thiazol-4-yl)acetylamino spectinomycin; 3'-Dihydro-3'-deoxy-4(R)-(2-((4-(trifluoromethoxy)phenyl)-amino) thiazol-4-yl)acetylamino spectinomycin; 3'-Dihydro-3'-deoxy-4(R)-(2-((4-(trifluoromethyl)phenyl)amino)thiazol-4-yl)acetylamino spectinomycin; 3'-Dihydro-3'-deoxy-4(R)-(5-(4-fluorophenyl)pyridin-2-yl)acetylamino spectinomycin; 3'-Dihydro-3'-deoxy-4(R)-(5-(3-methoxyphenyl) pyridin-2-yl)acetylamino spectinomycin; 3'-Dihydro-3'-deoxy-4(R)-(4-chloropyridin-2-yl)acetylamino spectinomycin; or a pharmaceutically acceptable salt or prodrug thereof.

In some embodiments, the compound of Formula (I) is administered prophylactically to prevent or reduce the incidence of one of: (a) a bacterial infection in a subject at risk of infection; (b) a recurrence of a bacterial infection; and (c) combinations thereof. In some embodiments, the compound of Formula (I) is administered to treat an existing bacterial infection.

In some embodiments, the presently disclosed subject matter provides a method of treating tuberculosis in a subject in need of treatment thereof, the method comprising administering to the subject an effective amount of a compound of Formula (I):

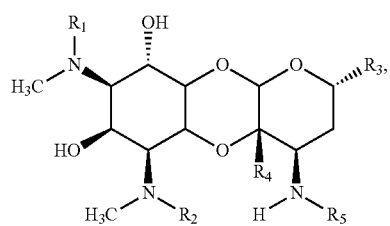

(I)

wherein:
R$_1$ and R$_2$ are each independently H, alkoxycarbonyl, or aralkoxycarbonyl;
R$_3$ is alkyl;
R$_4$ is H, hydroxy, alkyl, or alkoxy; and
R$_5$ is selected from the group comprising alkyl, substituted alkyl, aralkyl, substituted aralkyl, aryl, substituted aryl, and acyl;
or a pharmaceutically acceptable salt or a prodrug thereof.

In some embodiments, R$_1$ and R$_2$ are each H. In some embodiments, R$_3$ is methyl or butyl. In some embodiments, R$_4$ is H, OH, methyl, or methoxy.

In some embodiments, R$_5$ is acyl. In some embodiments, R$_5$ has the structure —C(=O)R$_6$, wherein R$_6$ is selected from the group comprising alkyl, substituted alkyl, aralkyl, substituted aralkyl, aryl, and substituted aryl. In some embodiments, R$_6$ is selected from the group comprising heteroaryl, substituted heteroaryl, 2-substituted phenyl, 4-halo-substituted phenyl, —CH$_2$R$_7$, and —C(R$_8$)$_2$; R$_7$ is selected from the group comprising aralkyl, substituted aralkyl, heteroaryl, substituted heteroaryl, and substituted phenyl, wherein said substituted phenyl is selected from the group comprising fluoro-substituted phenyl, alkyl-substituted phenyl, 2-substituted phenyl, 3-mono-substituted phenyl, 2,3-di-substituted phenyl, and di-substituted phenyl wherein two phenyl carbons are together substituted with an alkylene; and each R$_8$ is independently aryl or substituted aryl. In some embodiments, R$_6$ is selected from the group comprising —CH$_2$NHC(CH$_3$)$_3$, —CH$_2$CH(CH$_3$)$_2$, —CH(NH$_2$)CH(CH$_3$)CH$_2$CH$_3$, —CH(NH$_2$)CH(CH$_3$)$_2$, —CH(CH$_2$C$_6$H$_5$)NHC(=O)CH$_2$NH$_2$, —CH$_2$CH$_2$NHC(=O)C$_6$H$_5$, and —CH$_2$CH$_2$NHC(=O) CH$_2$C$_6$H$_5$; or a pharmaceutically acceptable salt or a prodrug thereof.

In some embodiments, the compound of Formula (I) is a compound of Formula (Ia):

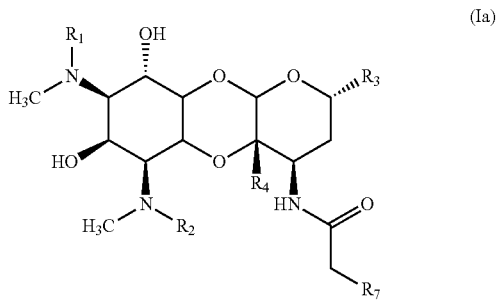

(Ia)

wherein:
R$_1$ and R$_2$ are each independently H, alkoxycarbonyl, or aralkoxycarbonyl;
R$_3$ is alkyl;
R$_4$ is H, hydroxy, alkyl, or alkoxy; and
R$_7$ is selected from the group comprising aralkyl, substituted aralkyl, heteroaryl, substituted heteroaryl, and substituted phenyl, wherein said substituted phenyl is selected from the group comprising fluoro-substituted phenyl, alkyl-substituted phenyl, 2-substituted phenyl, 3-mono-substituted phenyl, 2,3-di-substituted phenyl, and di-substituted phenyl wherein two phenyl carbons are together substituted with an alkylene; and
or a pharmaceutically acceptable salt or prodrug thereof.

In some embodiments, R$_7$ is substituted phenyl selected from the group comprising 4-fluorophenyl, 4-methylphenyl, 3-methylphenyl, 3-methoxyphenyl, 2-methoxyphenyl, 3,4- methylenedioxyphenyl, and 2,3-difluorophenyl. In some embodiments, $R_7$ is heteroaryl or substituted heteroaryl comprising a heteroaryl group selected from the group comprising pyridyl, triazolyl, triazinyl, pyrimidinyl, pyridazinyl, oxazolyl, furanyl, benzofuranyl, thiophenyl, pyrrolyl, imidazoyl, thiazoyl, quinolinyl, isoquinolinyl, benzooxazolyl, and benzothiazolyl. In some embodiments, $R_7$ is heteroaryl or substituted heteroaryl comprising a heteroaryl group selected from pyridyl, thiazoyl, benzooxazolyl, and benzothiazolyl.

In some embodiments, $R_7$ is substituted heteroaryl, wherein the heteroaryl is substituted with one or more of the group comprising $NH_2$, OH, alkylamino, arylamino, nitro, halo, alkyl, substituted alkyl, alkoxy, perhaloalkoxy, aralkyl, acyl, aryl, aryloxy, and substituted aryl. In some embodiments, $R_7$ is substituted heteroaryl, wherein the heteroaryl is substituted with one or more of the group comprising fluoro, chloro, bromo, methoxy, methyl, nitro, trifluoromethoxy, phenylamino, phenyl, and trifluoromethyl.

In some embodiments, $R_7$ is aralkyl or substituted aralkyl, wherein said aralkyl or substituted aralkyl comprises a heteroaryl or substituted heteroaryl group.

In some embodiments, $R_7$ comprises a nitrogen-containing heteroaryl group and the compound of Formula (Ia) has a structure of one of Formulas (Ib), (Ic), or (Id):

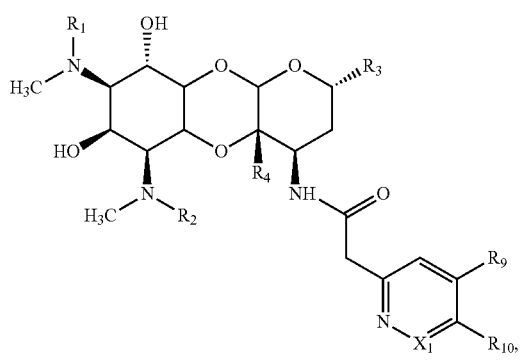

(Ib)

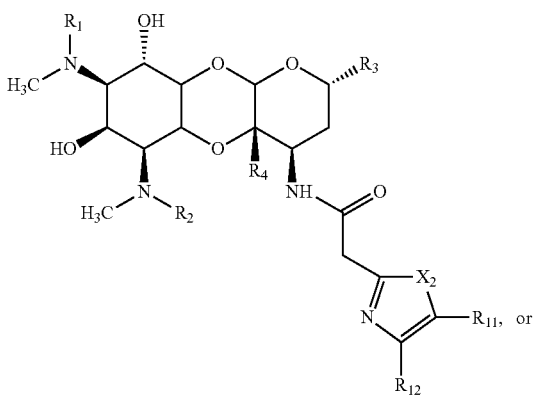

(Ic)

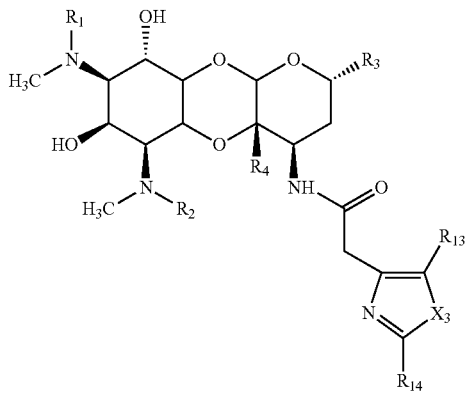

(Id)

wherein:

$R_1$ and $R_2$ are each independently H, alkoxycarbonyl, or aralkoxycarbonyl;

$R_3$ is alkyl;

$R_4$ is H, hydroxy, alkyl, or alkoxy;

$X_1$ is CH or N;

$X_2$ and $X_3$ are each O, S, or NH;

$R_9$, $R_{10}$, $R_{11}$, $R_{12}$, $R_{13}$, and $R_{14}$ are independently selected from the group comprising H, halo, hydroxy, nitro, $N(R_{15})_2$, alkyl, substituted alkyl, alkoxy, perhaloalkoxy, aralkyl, substituted aralkyl, aralkoxy, aryl, aryloxy, acyl and substituted aryl;

or wherein $R_9$ and $R_{10}$ together or $R_{11}$ and $R_{12}$ together are alkylene; and each $R_{15}$ is independently selected from the group comprising H, alkyl, substituted alkyl, aralkyl, substituted aralkyl, aryl, and substituted aryl;

or a pharmaceutically acceptable salt or a prodrug thereof.

In some embodiments, the compound is selected from the group comprising:

3'-dihydro-3'-deoxy-4(R)-(3-pyridin-3-yl)propionylamino spectinomycin;

3'-dihydro-3'-deoxy-4(R)-(pyridin-2-yl)acetylamino spectinomycin;

3'-dihydro-3'-deoxy-4(R)-4-fluorobenzoylamino spectinomycin;

3'-dihydro-3'-deoxy-4(R)-furan-2-carboxylicamino spectinomycin;

3'-dihydro-3'-deoxy-4(R)-(4-fluorophenyl)acetylamino spectinomycin;

3'-dihydro-3'-deoxy-4(R)-(pyridin-3-yl)acetylamino spectinomycin;

3'-dihydro-3'-deoxy-4(R)-pyridin-2-carboxylicamino spectinomycin;

3'-dihydro-3'-deoxy-4(R)-p-tolylacetylamino spectinomycin;

3'-dihydro-3'-deoxy-4(R)-(3-methoxy-phenyl)acetylamino spectinomycin;

3'-dihydro-3'-deoxy-4(R)-[3,4-(methylene dioxy)phenyl]acetylamino spectinomycin;

3'-dihydro-3'-deoxy-4(R)-m-tolylacetylamino spectinomycin;

3'-dihydro-3'-deoxy-4(R)-(pyridin-4-yl)acetylamino spectinomycin;

3'-dihydro-3'-deoxy-4(R)-(thiazol-4-yl)acetylamino spectinomycin;

3'-dihydro-3'-deoxy-4(R)-(2-aminothiazol-4-yl)acetylamino spectino-mycin;

3'-dihydro-3'-deoxy-4(R)-(5-fluoropyridin-2-yl)acetylamino spectinomycin;
3'-dihydro-3'-deoxy-4(R)-(2,3-difluorophenyl)acetylamino spectinomycin;
3'-dihydro-3'-deoxy-4(R)-(2-methoxyphenyl)acetylamino spectinomycin;
3'-dihydro-3'-deoxy-4(R)-(pyridazin-3-yl)acetylamino spectinomycin;
3'-dihydro-3'-deoxy-4(R)-(benzooxazol-2-yl)acetylamino spectinomycin;
3'-dihydro-3'-deoxy-4(R)-(1H-imidazol-4-yl)acetylamino spectinomycin;
3'-dihydro-3'-deoxy-4(R)-[3(R)-amino-3-(4-fluorophenyl)]propanoylamino spectinomycin;
3'-dihydro-3'-deoxy-4(R)-(thiazol-2-yl)acetylamino spectinomycin;
3'-dihydro-3'-deoxy-4(R)-(5-nitropyridin-2-yl)acetylamino spectinomycin;
3'-dihydro-3'-deoxy-4(R)-(benzothiazol-2-yl)acetylamino spectinomycin;
3'-dihydro-3'-deoxy-4(R)-[2(S)-amino-3-phenyl]propanoylamino spectino-mycin;
3'-dihydro-3'-deoxy-4(R)-(5-bromopyridin-2-yl)acetylamino spectino-mycin;
3'-dihydro-3'-deoxy-4(R)-(2-phenylthiazol-4-yl)acetylamino spectino-mycin;
3'-dihydro-3'-deoxy-4(R)-(pyridin-2-yl)propanoylamino spectinomycin;
3'-dihydro-3'-deoxy-4(R)-(5-phenylpyridin-2-yl)acetylamino spectino-mycin;
3'-dihydro-3'-deoxy-4(R)-(2-(phenylamino)thiazol-4-yl)acetylamino spectinomycin;
3'-Dihydro-3'-deoxy-4(R)-(5-(4-chlorophenyl)pyridin-2-yl)acetylamino spectinomycin;
3'-Dihydro-3'-deoxy-4(R)-(quinoline-8-yl)carbonylamino spectinomycin;
3'-Dihydro-3'-deoxy-4(R)-2-(1-benzyl-1H-1,2,3-triazol-4-yl)acetylamino spectinomycin;
3'-Dihydro-3'-deoxy-4(R)-(2-((4-fluorophenyl)amino)thiazol-4-yl)acetylamino spectinomycin;
3'-Dihydro-3'-deoxy-4(R)-(2-((3-fluorophenyl)amino)thiazol-4-yl)acetylamino spectinomycin;
3'-Dihydro-3'-deoxy-4(R)-(2-((4-(trifluoromethoxy)phenyl)amino)thiazol-4-yl)acetylamino spectinomycin;
3'-Dihydro-3'-deoxy-4(R)-(2-((4-(trifluoromethyl)phenyl)amino)thiazol-4-yl)acetylamino spectinomycin;
3'-Dihydro-3'-deoxy-4(R)-(5-(4-fluorophenyl)pyridin-2-yl)acetylamino spectinomycin;
3'-Dihydro-3'-deoxy-4(R)-(5-(3-methoxyphenyl)pyridin-2-yl)acetylamino spectinomycin;
3'-Dihydro-3'-deoxy-4(R)-(4-chloropyridin-2-yl)acetylamino spectino-mycin;
3'-dihydro-3'-deoxy-4(R)-(tert-butylamino)acetylamino spectinomycin;
3'-dihydro-3'-deoxy-4(R)-(3-methyl)butanoylamino spectinomycin;
3'-dihydro-3'-deoxy-4(R)-[(2S,3S)-2-amino-3-methyl]pentanoylamino spectinomycin;
3'-dihydro-3'-deoxy-4(R)-[2(S)-amino-3-methyl]butanoylamino spectinomycin;
3'-dihydro-3'-deoxy-4(R)-dodecanoylamino spectinomycin;
3'-dihydro-3'-deoxy-4(R)-(3-amino)-propanoylamino spectinomycin;
3'-dihydro-3'-deoxy-4(R)-phenylacetylamino spectinomycin;
3'-dihydro-3'-deoxy-4(R)-cyclopropylmethylamino spectinomycin;
3'-dihydro-3'-deoxy-4(R)-(3-methyl)butylamino spectinomycin;
3'-dihydro-3'-deoxy-4(R)-dodecylamino spectinomycin;
3'-dihydro-3'-deoxy-4(R)-furan-2-yl-methylamino spectinomycin;
3'-dihydro-3'-deoxy-4(R)-(3-methoxy)benzylamino spectinomycin;
3'-dihydro-3'-deoxy-4(R)-(4-fluoro)benzylamino spectinomycin;
3'-dihydro-3'-deoxy-4(R)-(4-methyl)benzylamino spectinomycin;
3'-dihydro-3'-deoxy-4(R)-2-phenylethylamino spectinomycin;
3'-dihydro-3'-deoxy-4(R)-(4-methoxyphenyl)acetylamino spectinomycin;
3'-dihydro-3'-deoxy-4(R)-[2(S)-aminopropanoylamino spectinomycin; and
3'-dihydro-3'-deoxy-4(R)-(2-amino)acetylamino spectinomycin;
or a pharmaceutically acceptable salt or prodrug thereof.

In some embodiments, the compound is a pharmaceutically acceptable salt. In some embodiments, the compound is a hydrochloride or hydrobromide salt. In some embodiments, the compound is administered orally or via inhalation.

In some embodiments, the method further comprises administering to the subject an additional therapeutic compound. In some embodiments, the additional therapeutic compound is an antibiotic. In some embodiments, the additional therapeutic compound is an anti-tuberculosis therapeutic. In some embodiments, the additional therapeutic compound is selected from the group comprising isoniazid, ethambutol, rifampicin, kanamycin, capreomycin, linezolid, and streptomycin.

In some embodiments, the compound of Formula (I) is administered prophylactically to prevent or reduce the incidence of one of: (a) a *Mycobacterium tuberculosis* infection in a subject at risk of infection; (b) a recurrence of a *Mycobacterium tuberculosis* infection; and (c) combinations thereof. In some embodiments, the compound of Formula (I) is administered to treat an existing *Mycobacterium tuberculosis* infection. In some embodiments, the compound of Formula (I) is administered to treat an infection of a multi-drug resistant strain of *Mycobacterium tuberculosis*. In some embodiments, the compound of Formula (I) has a minimum inhibitory concentration (MIC) against *Mycobacterium tuberculosis* of 25 µg/mL or less.

In some embodiments, the presently disclosed subject matter provides a compound selected from the group comprising:
3'-dihydro-3'-deoxy-4(R)-cyclopropylmethylamino spectinomycin;
3'-dihydro-3'-deoxy-4(R)-furan-2-yl-methylamino spectinomycin;
3'-dihydro-3'-deoxy-4(R)-(3-methoxy)benzylamino spectinomycin;
3'-dihydro-3'-deoxy-4(R)-(4-fluoro)benzylamino spectinomycin; and
3'-dihydro-3'-deoxy-4(R)-2-phenylethylamino spectinomycin;
or a pharmaceutically acceptable salt or prodrug thereof.

In some embodiments, the presently disclosed subject matter provides a method of treating an a bacterial infection in a subject in need of treatment thereof, wherein the method comprises administering to the subject an effective amount of a compound selected from the group comprising: 3'-dihydro-3'-deoxy-4(R)-cyclopropylmethylamino spectinomycin; 3'-dihydro-3'-deoxy-4(R)-furan-2-yl-methylamino spectinomycin; 3'-dihydro-3'-deoxy-4(R)-(3-methoxy)benzylamino spectinomycin; 3'-dihydro-3'-deoxy-4(R)-(4-fluoro)benzylamino spectinomycin; and 3'-dihydro-3'-deoxy-4(R)-2-phenylethylamino spectinomycin; or a pharmaceutically acceptable salt or prodrug thereof. In some embodiments, the bacterial infection is an *Enterococcus faecalis* infection, and the method comprises administering to the subject an effective amount of 3'-dihydro-3'-deoxy-4(R)-furan-2-yl-methylamino spectinomycin, or a pharmaceutically acceptable salt or prodrug thereof.

It is an object of the presently disclosed subject matter to provide novel spectinomycin derivatives, such as, but not limited to, 3'-dihydro-3'-(R)-acylamino spectinomycin derivatives, and compounds for treating microbial infections, including infections of *Mycobacterium tuberculosis* complex.

An object of the presently disclosed subject matter having been stated hereinabove, and which is achieved in whole or in part by the presently disclosed subject matter, other objects will become evident as the description proceeds when taken in connection with the accompanying drawings as best described hereinbelow.

Figure 1:
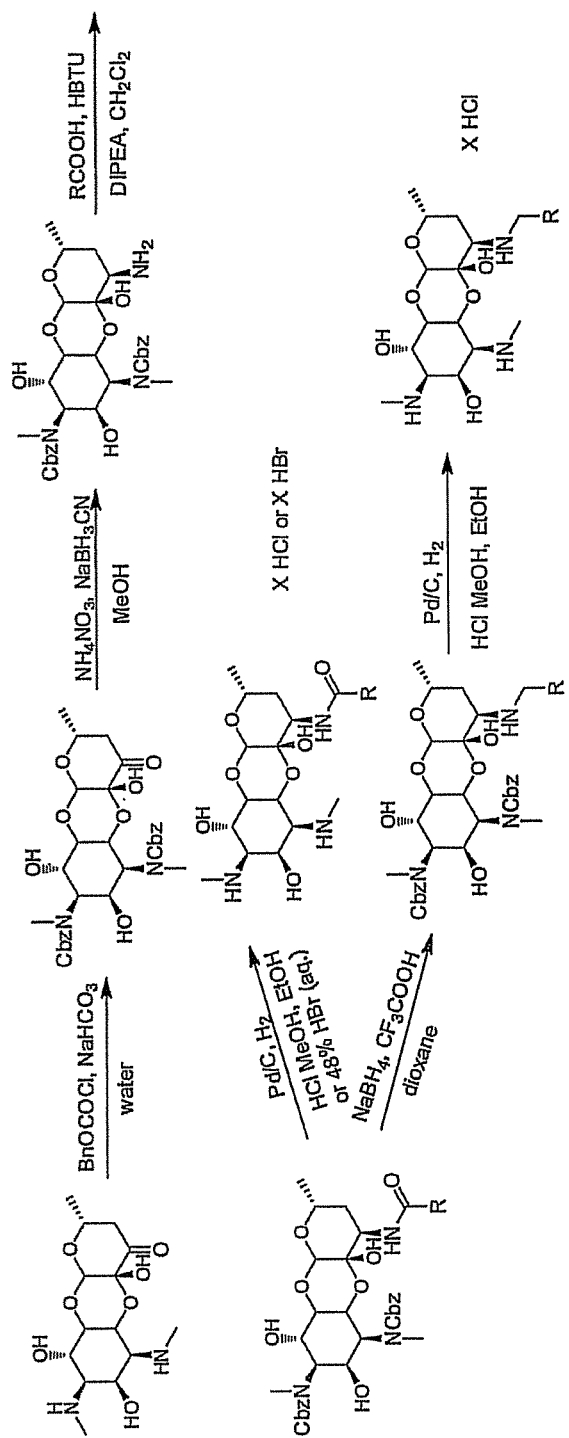
FIG. 1 is a schematic drawing of exemplary methods for synthesizing compounds of the presently disclosed subject matter.

FIG. 5 is a bar graph showing the comparative activity of spectinomycin analogs in an *E. coli* transcription/translation assay at either 6.6 μM (lighter bars) or 0.66 μM (darker bars).

FIG. 6 is a graph showing the pharmacokinetic profile of compound 1329 (intravenous, 10 mg/kg body weight) in rats. Each set of data is from one animal. Set 1 (circles) refers to data from animal 1. Set 2 (triangles) refers to data from animal 2. Set 3 (squares) refers to data from animal 3. Set 4 (diamonds) refers to data from animal 4.

DETAILED DESCRIPTION

The presently disclosed subject matter will now be described more fully hereinafter with reference to the accompanying Examples, in which representative embodiments are shown. The presently disclosed subject matter can, however, be embodied in different forms and should not be construed as limited to the embodiments set forth herein. Rather, these embodiments are provided so that this disclosure will be thorough and complete, and will fully convey the scope of the embodiments to those skilled in the art.

Unless otherwise defined, all technical and scientific terms used herein have the same meaning as commonly understood by one of ordinary skill in the art to which this presently described subject matter belongs. All publications, patent applications, patents, and other references mentioned herein are incorporated by reference in their entirety.

Throughout the specification and claims, a given chemical formula or name shall encompass all optical and stereoisomers, as well as racemic mixtures where such isomers and mixtures exist.

I. Definitions

Following long-standing patent law convention, the terms “a” and “an” mean “one or more” when used in this application, including the claims. Thus, “a compound” can refer to a plurality (i.e., two or more) compounds.

Unless otherwise indicated, all numbers expressing quantities of ingredients, reaction conditions, and so forth used in the specification and claims are to be understood as being modified in all instances by the term “about”. Accordingly, unless indicated to the contrary, the numerical parameters set forth in this specification and attached claims are approximations that can vary depending upon the desired properties sought to be obtained by the presently disclosed subject matter. Thus, the term “about”, as used herein when referring to a value or to an amount of mass, weight, time, temperature, volume, or percentage is meant to encompass variations of ±20% or ±10%, more preferably ±5%, even more preferably ±1%, and still more preferably ±0.1% from the specified amount, as such variations are appropriate to perform the disclosed method.

The term “and/or” when used to describe two or more activities, conditions, or outcomes refers to situations wherein both of the listed conditions are included or wherein only one of the two listed conditions are included.

The term “comprising”, which is synonymous with “including,” “containing,” or “characterized by” is inclusive or open-ended and does not exclude additional, unrecited elements or method steps. “Comprising” is a term of art used in claim language which means that the named elements are essential, but other elements can be added and still form a construct within the scope of the claim.

As used herein, the phrase “consisting of” excludes any element, step, or ingredient not specified in the claim. When the phrase “consists of” appears in a clause of the body of a claim, rather than immediately following the preamble, it limits only the element set forth in that clause; other elements are not excluded from the claim as a whole.

As used herein, the phrase “consisting essentially of” limits the scope of a claim to the specified materials or steps, plus those that do not materially affect the basic and novel characteristic(s) of the claimed subject matter.

With respect to the terms “comprising”, “consisting of”, and “consisting essentially of”, where one of these three terms is used herein, the presently disclosed and claimed subject matter can include the use of either of the other two terms.

As used herein the term “alkyl” refers to $C_{1-20}$ inclusive, linear (i.e., “straight-chain”), branched, or cyclic, saturated or at least partially and in some cases fully unsaturated (i.e., alkenyl and alkynyl)hydrocarbon chains, including for example, methyl, ethyl, propyl, isopropyl, butyl, isobutyl, tert-butyl, pentyl, hexyl, octyl, ethenyl, propenyl, butenyl, pentenyl, hexenyl, octenyl, butadienyl, propynyl, butynyl, pentynyl, hexynyl, heptynyl, and allenyl groups. “Branched” refers to an alkyl group in which a lower alkyl group, such as methyl, ethyl or propyl, is attached to a linear alkyl chain. “Lower alkyl” refers to an alkyl group having 1 to about 8 carbon atoms (i.e., a $C_{1-8}$ alkyl), e.g., 1, 2, 3, 4, 5, 6, 7, or 8 carbon atoms. “Higher alkyl” refers to an alkyl group having about 10 to about 20 carbon atoms, e.g., 10, 11, 12, 13, 14, 15, 16, 17, 18, 19, or 20 carbon atoms. In certain embodiments, "alkyl" refers, in particular, to $C_{1-8}$ straight-chain alkyls. In other embodiments, "alkyl" refers, in particular, to $C_{1-8}$ branched-chain alkyls.

Alkyl groups can optionally be substituted (a "substituted alkyl") with one or more alkyl group substituents, which can be the same or different. The term "alkyl group substituent" includes but is not limited to alkyl, substituted alkyl (including, but not limited to, perhaloalkyl, such as perfluoroalkyl), aralkyl, substituted aralkyl, halo, amino, alkylamino, arylamino, aryl, substituted aryl, nitro, thio, acyl, hydroxyl, aryloxyl, alkoxyl, perhaloalkoxy, alkylthio, arylthio, aralkyloxyl, aralkylthio, carboxyl, alkoxycarbonyl, oxo, and cycloalkyl. There can be optionally inserted along the alkyl chain one or more oxygen, sulfur or substituted or unsubstituted nitrogen atoms, wherein the nitrogen substituent is hydrogen, lower alkyl (also referred to herein as "alkylaminoalkyl"), or aryl.

Thus, as used herein, the term "substituted alkyl" includes alkyl groups, as defined herein, in which one or more atoms or functional groups of the alkyl group are replaced with another atom or functional group, including for example, alkyl, substituted alkyl, aralkyl, substituted aralkyl, halogen, aryl, substituted aryl, alkoxyl, carboxyl, acyl, hydroxyl, nitro, amino, alkylamino, dialkylamino, sulfate, and mercapto.

The term "aryl" is used herein to refer to an aromatic substituent that can be a single aromatic ring, or multiple aromatic rings that are fused together. The term "aryl" specifically encompasses heterocyclic aromatic compounds. The aromatic ring(s) can comprise phenyl, naphthyl, furanyl, thiophenyl, and pyridyl, among others. In particular embodiments, the term "aryl" means a cyclic aromatic comprising about 5 to about 10 carbon atoms, e.g., 5, 6, 7, 8, 9, or 10 carbon atoms, and including 5- and 6-membered hydrocarbon and heterocyclic aromatic rings.

The aryl group can be optionally substituted (a "substituted aryl") with one or more aryl group substituents, which can be the same or different, wherein "aryl group substituent" includes but is not limited to alkyl, substituted alkyl (including but not limited to perhaloalkyl (e.g., perfluoroalkyl)), aryl, substituted aryl, aralkyl, hydroxyl, alkoxyl, perhaloalkoxyl, aryloxyl, aralkyloxyl, carboxyl, acyl, halo, nitro, alkoxycarbonyl, aryloxycarbonyl, aralkoxycarbonyl, acyloxyl, acylamino (e.g., aroylamino), amido, carbamoyl, alkylcarbamoyl, dialkylcarbamoyl, arylthio, alkylthio, alkylene, and —NR'R", wherein R' and R" can each be independently hydrogen, alkyl, substituted alkyl, aryl, substituted aryl, and aralkyl.

Thus, as used herein, the term "substituted aryl" includes aryl groups, as defined herein, in which one or more atoms or functional groups of the aryl group are replaced with another atom or functional group, including for example, alkyl, substituted alkyl, halogen, aryl, substituted aryl, alkoxyl, aryloxy (e.g., phenoxy), hydroxyl, nitro, amino, alkylamino (e.g., phenylamino), dialkylamino, arylamino, carboxy, acyl (e.g., benzoyl), sulfate, and mercapto. Thus, substituted aryl includes aryl-substituted aryl (i.e., "biaryl").

Specific examples of aryl groups include, but are not limited to, cyclopentadienyl, phenyl, napthyl, and heteroaryl groups, including, but not limited to, furan, thiophene, pyrrole, oxazole, triazole, pyran, pyridine, imidazole, benzimidazole, benzofuran, benzooxazole, benzothiazole, isothiazole, isoxazole, pyrazole, pyrazine, thiazole, triazine, pyrimidine, pyridazine, quinoline, isoquinoline, indole, carbazole, and the like.

The term "heteroaryl" refers to aryl groups as defined above, wherein the backbone of the aromatic ring or rings includes at least one heteroatom such as, but not limited to, oxygen, sulfur, nitrogen, or selenium. Exemplary heteroaryl groups include, but are not limited to, furan, thiophene, pyrrole, pyran, triazole (e.g., 1,2,3-triazolyl or 1,2,4-triazolyl), pyridine (e.g., 2-pyridinyl, 3-pyridinyl, or 4-pyridinyl), imidazole, benzimidazole, oxazole, isothiazole, benzofuran, benzooxazole, isoxazole, pyrazole, pyrazine, pyridazine, triazine, thiazole (e.g., 4-thiazoyl or 5-thiazoyl), benzothiazole, benzotriazine, pyrimidine (e.g., 4-pyrimidyl or 2-pyrimidyl), quinoline, isoquinoline, indole, and carbazole. "Nitrogen-containing heteroaryl" refers to heteroaryl groups wherein the backbone of the aromatic ring or rings includes at least one nitrogen. Exemplary nitrogen-containing heteroaryl groups include, but are not limited to, pyrrole, triazole, pyridine, imidazole, benzimidazole, oxazole, isothiazole, benzooxazole, isoxazole, pyrazole, pyrazine, pyridazine, triazine, thiazole, benzothiazole, benzotriazine, pyrimidine, quinoline, isoquinoline, indole, and carbazole.

As used herein, the term "acyl" refers to an organic acid group wherein the —OH of the carboxyl group has been replaced with another substituent. Thus, the acyl group can be represented by the formula: RC(=O)—, wherein R is an alkyl, aralkyl, or aryl group, as defined herein, optionally substituted by one or more alkyl or aryl group substituent. As such, the term "acyl" specifically includes arylacyl groups (also referred to herein as "aroyl" groups), wherein R is aryl (e.g., furanyl or phenyl) or substituted aryl. Specific examples of acyl groups include acetyl and benzoyl.

The term "acylamino" refers to the —NHC(=O)R group, wherein R is alkyl, aralkyl or aryl, optionally substituted by one or more alkyl or aryl group substituents.

"Cyclic" and "cycloalkyl" refer to a non-aromatic mono- or multicyclic ring system of about 3 to about 10 carbon atoms, e.g., 3, 4, 5, 6, 7, 8, 9, or 10 carbon atoms. The cycloalkyl group can be optionally partially unsaturated. The cycloalkyl group also can be optionally substituted with an alkyl group substituent as defined herein, oxo, and/or alkylene. There can be optionally inserted along the cyclic alkyl chain one or more oxygen, sulfur or substituted or unsubstituted nitrogen atoms, wherein the nitrogen substituent is hydrogen, alkyl, substituted alkyl, aryl, or substituted aryl, thus providing a heterocyclic group. Representative monocyclic cycloalkyl rings include cyclopentyl, cyclohexyl, and cycloheptyl. Multicyclic cycloalkyl rings include adamantyl, octahydronaphthyl, decalin, camphor, camphane, and noradamantyl.

"Alkylene" refers to a straight or branched bivalent aliphatic hydrocarbon group having from 1 to about 20 carbon atoms, e.g., 1, 2, 3, 4, 5, 6, 7, 8, 9, 10, 11, 12, 13, 14, 15, 16, 17, 18, 19, or 20 carbon atoms. The alkylene group can be straight, branched or cyclic. The alkylene group also can be optionally unsaturated and/or substituted with one or more "alkyl group substituents." There can be optionally inserted along the alkylene group one or more oxygen, sulfur or substituted or unsubstituted nitrogen atoms (also referred to herein as "alkylaminoalkyl"), wherein the nitrogen substituent is alkyl as previously described. Exemplary alkylene groups include methylene (—CH$_2$—); ethylene (—CH$_2$—CH$_2$—); propylene (—(CH$_2$)$_3$—); cyclohexylene (—C$_6$H$_{10}$—); —CH=CH—CH=CH—; —CH=CH—CH$_2$—; —(CH$_2$)$_q$—N(R)—(CH$_2$)$_r$—, wherein each of q and r is independently an integer from 0 to about 20, e.g., 0, 1, 2, 3, 4, 5, 6, 7, 8, 9, 10, 11, 12, 13, 14, 15, 16, 17, 18, 19, or 20, and R is hydrogen or lower alkyl; methylenedioxyl (—O—CH$_2$—O—); and ethylenedioxyl (—O—(CH$_2$)$_2$—O—). An alkylene group can have about 2 to about 3 carbon atoms and can further have 6-20 carbons.

"Alkoxyl" or "alkoxy" refer to an alkyl-O— group wherein alkyl is as previously described. The term "alkoxyl" as used herein can refer to $C_{1-20}$ inclusive, linear, branched, or cyclic, saturated or unsaturated oxo-hydrocarbon chains, including, for example, methoxyl, ethoxyl, propoxyl, isopropoxyl, butoxyl, t-butoxyl, and pentoxyl.

"Aryloxyl" and "aryloxy" refer to an aryl-O— group wherein the aryl group is as previously described, including a substituted aryl. The term "aryloxyl" as used herein can refer to phenyloxyl or hexyloxyl, and alkyl, substituted alkyl, halo, or alkoxyl substituted phenyloxyl or hexyloxyl.

"Aralkyl" refers to an aryl-alkyl-group wherein aryl and alkyl are as previously described, and can include substituted aryl (and heteroaryl and substituted heteroaryl) and substituted alkyl. Exemplary aralkyl groups include, but are not limited to, benzyl, phenylethyl, furanylmethyl, pyridinylmethyl, pyridinylethyl, and naphthylmethyl.

"Substituted aralkyl" refers to an aralkyl group wherein the aryl portion, the alkyl portion, or both the aryl and alkyl portions of the aralkyl group are substituted by one or more alkyl or aryl group substituents.

"Aralkyloxyl," "aralkyloxy," and "aralkoxy" refer to an aralkyl-O— group wherein the aralkyl group is as previously described. The aralkyl group of an aralkyloxyl group can be a heteroaryl group. An exemplary aralkyloxyl group is benzyloxyl.

"Perhaloalkyl" refers to an alkyl group as defined hereinabove, wherein each of the hydrogen atoms attached to the carbon chain is replaced by halide. "Perfluoroalkyl" is a perhaloalkyl group wherein the halide is fluoride (i.e., —F), such as but not limited to trifluoromethyl (i.e., —$CF_3$).

"Perhaloalkoxy" or "perhaloalkoxyl" refer to an —O-perhaloalkyl group. Perhaloalkoxy groups include, but are not limited to, "perfluoroalkoxy" groups (i.e., —O-perfluoroalkyl groups). Exemplary perhaloalkoxy groups are trifluoromethoxy (i.e., —$OCF_3$) and tribromomethoxy (i.e., —$OCBr_3$).

"Alkylamino" refers to an —NRR' group wherein R and R' are hydrogen, alkyl, or substituted alkyl as previously described, so long as at least one of R and R' is not H. Exemplary alkylamino groups include methylamino, t-butylamino, ethylamino, isopropylamino, ethylmethylamino, dimethylamino, and diethylamino.

"Arylamino" refers to an —NRR' group wherein R and R' are H, aryl or substituted aryl as previously described, so long as at least one of R and R' is not H. Exemplary aryl amino groups include phenylamino, p-chlorophenylamino, p-fluorophenylamino, m-fluorophenylamino, p-methoxyphenylamino, p-trifluoromethylphenylamino, and the like.

"Alkoxycarbonyl" refers to an alkyl-O—C(=O)— group. Exemplary alkoxycarbonyl groups include methoxycarbonyl, ethoxycarbonyl, butyloxycarbonyl, and t-butyloxycarbonyl.

"Aryloxycarbonyl" refers to an aryl-O—C(=O)— group. Exemplary aryloxycarbonyl groups include phenoxy- and naphthoxy-carbonyl.

"Aralkoxycarbonyl" refers to an aralkyl-O—C(=O)— group. An exemplary aralkoxycarbonyl group is benzyloxycarbonyl.

The term "amino" refers to the —$NH_2$ group.
The term "carbonyl" refers to the —C(=O)— group.
The term "carboxyl" refers to the —C(O)OH or —C(=O)$O^-$ group.
The term "amido" refers to the —C(=O)$NR_2$ group, wherein each R group is independently H, alkyl, substituted alkyl, aralkyl, substituted aralkyl, aryl or substituted aryl.

The terms "halo", "halide", or "halogen" as used herein refer to fluoro, chloro, bromo, and iodo groups.

The terms "hydroxyl" and "hydroxy" refer to the —OH group.

The term "nitro" refers to the —$NO_2$ group.

The term "thio" refers to a —SR group, wherein R is H, alkyl, substituted alkyl, aralkyl, substituted aralkyl, aryl, or substituted aryl.

When the term "independently selected" is used, the substituents being referred to (e.g., R groups, such as groups $R_1$ and $R_2$, or groups X and Y), can be identical or different. For example, both $R_1$ and $R_2$ can be substituted alkyls, or $R_1$ can be hydrogen and $R_2$ can be a substituted alkyl, and the like.

A named "R", "R'," or "X" group will generally have the structure that is recognized in the art as corresponding to a group having that name, unless specified otherwise herein. For the purposes of illustration, certain representative "R" and "X" groups as set forth above are defined below. These definitions are intended to supplement and illustrate, not preclude, the definitions that would be apparent to one of ordinary skill in the art upon review of the present disclosure.

II. General Considerations

Spectinomycin (MW 332) is the lowest molecular weight member of the aminoglycoside family of antibiotics. It binds selectively to a unique binding site in the bacterial ribosome, in RNA helix 34 of the head domain of the 30S ribosomal sub unit, blocking translocation and consequently protein synthesis. This is a distinct location from the binding sites of the other ribosomally active anti-tubercular therapeutics including streptomycin, kanamycin, capreomycin and linezolid. Spectinomycin is principally used as a second line therapeutic option to treat *Neisseria gonorrhoeae* infections in patients who are intolerant of the more clinically efficacious frontline anti-neisseria therapeutics such as cephalosporins or fluoroquinolones. See Holloway, *The Medical Clinics of North America*, 66(1), 169-173 (1982); and Novak et al., *Antimicrob. Agents Chemother.*, 34(12), 2342-2347 (1990).

Since the discovery and development of spectinomycin, the structurally similar compounds trospectomycin and acmimycin have been clinically evaluated, with trospectomycin advancing to Phase III clinical trials for the treatment of general gram positive bacterial infections. See Gismondo et al., *Drugs Exp. Clin. Res.*, 17(2), 101-104 (1991). The structures of spectinomycin, trospectomycin and acmimycin are shown below in Scheme 1.

Scheme 1. Structures of Spectinomycin, Trospectomycin and Acmimycin.

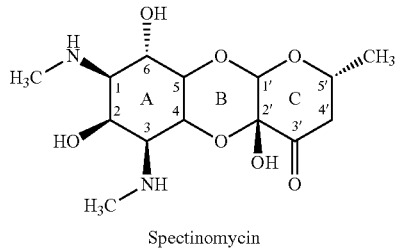

Spectinomycin

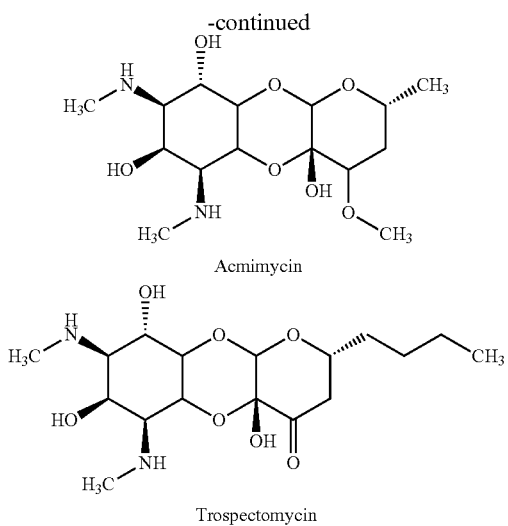

Acmimyin

Trospectomycin

III. 3'-Acylamino and 3'-Alkylamino Spectinomycin Derivatives

The presently disclosed subject matter relates, in part, to 3'-deoxy 3'-acylamino and 3'-deoxy 3'-alkylamino spectinomycin analogs. In some embodiments, the presently disclosed subject matter provides a compound of Formula (I):

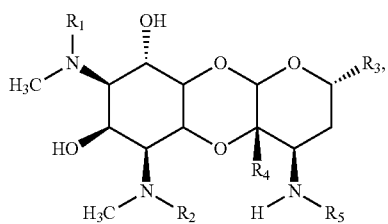

wherein:

$R_1$ and $R_2$ are each independently selected from the group including, but not limited to, H, alkoxycarbonyl, and aralkoxycarbonyl;

$R_3$ is alkyl;

$R_4$ are independently selected from the group including, but not limited to, H, hydroxy, alkyl, or alkoxy; and $R_5$ is selected from the group including, but not limited to, alkyl, substituted alkyl, aralkyl, substituted aralkyl, aryl, substituted aryl, and acyl; or a pharmaceutically acceptable salt or a prodrug thereof.

In some embodiments, $R_1$ and $R_2$ are each H. In some embodiments, one or both of $R_1$ and $R_2$ are nitrogen-protecting groups. Nitrogen-protecting groups that can be used according to the presently disclosed subject matter are described, for example, Greene and Wuts, Protective Groups in Organic Synthesis, 3$^{rd}$ Edition; New York, John Wiley & Sons, Inc., 1999. In some embodiments, $R_1$ and/or $R_2$ are alkoxycarbonyl or aralkoxycarbonyl groups that can form a carbamate with the spectinomycin nitrogen atom(s). In some embodiments, $R_1$ and/or $R_2$ are groups that can be removed via catalytic hydrogenation. For instance, a variety of aralkoxycarbonyl groups can be used to mask amino groups and can be removed via catalytic hydrogenation (e.g., using a palladium catalyst). In some embodiments, $R_1$ and/or $R_2$ are aralkoxylcarbonyl selected from benzyloxycarbonyl and benzyloxycarbonyl substituted by one or more halo, alkoxy, and nitro groups. Such groups include, but are not limited to, benzyloxycarbonyl (CBz), p-methoxybenzyloxycarbonyl (Moz), p-nitrobenzyloxycarbonyl (PNZ), p-bromobenzyloxycarbonyl, p-chlorobenzyloxycarbonyl, 2,4-dichlorobenzyloxycarbonyl, and 3,4-dimethoxy-6-nitrobenzyloxycarbonyl. Additional aralkoxycarbonyl protecting groups include, but are not limited to, diphenylmethyloxycarbonyl, 5-benzisoxazolylmethyloxycarbonyl (Bic) and 9-anthrylmethyloxycarbonyl. In some embodiments, both $R_1$ and $R_2$ are CBz.

In some embodiments, $R_3$ is a $C_1$-$C_8$ alkyl group (e.g., methyl, ethyl, or a branched, straight-chain or cyclic propyl, butyl, pentyl, hexyl, heptyl, or octyl). In some embodiments, $R_3$ is methyl or butyl (e.g., n-butyl).

In some embodiments, $R_4$ is selected from H, OH, methyl and methoxy. In some embodiments, $R_4$ is hydroxy.

In some embodiments, $R_5$ is alkyl, substituted alkyl, aralkyl, substituted aralkyl, aryl, or substituted aryl. In some embodiments, $R_5$ includes a heteroaryl group or a cycloalkyl group (e.g., —$CH_2$-heteroaryl or —$CH_2$-cycloalkyl). In some embodiments, the compound of Formula (I) is selected from the group comprising:

3'-dihydro-3'-deoxy-4(R)-cyclopropylmethylamino spectinomycin (1419);

3'-dihydro-3'-deoxy-4(R)-furan-2-yl-methylamino spectinomycin (1422);

3'-dihydro-3'-deoxy-4(R)-(3-methoxy)benzylamino spectinomycin (1423);

3'-dihydro-3'-deoxy-4(R)-(4-fluoro)benzylamino spectinomycin (1424); and

3'-dihydro-3'-deoxy-4(R)-2-phenylethylamino spectinomycin (1450);

or the pharmaceutically acceptable salts or prodrugs thereof.

In some embodiments, $R_5$ is acyl and the compound of Formula (I) is an 3'-acylamino spectinomycin derivative, which can also be referred to as a "spectinamide". Thus, $R_5$ can have the structure —C(=O)$R_6$, wherein $R_6$ is selected from the group comprising alkyl, substituted alkyl, aralkyl, substituted aralkyl, aryl, and substituted aryl. In some embodiments, $R_6$ is or comprises a heteroaryl group.

In some embodiments, $R_6$ is selected from the group comprising heteroaryl, substituted heteroaryl, 2-substituted phenyl, 4-halo-substituted phenyl, —$CH_2R_7$, and —$C(R_8)_2$; wherein $R_7$ is selected from the group comprising aralkyl, substituted aralkyl, heteroaryl, substituted heteroaryl, and substituted phenyl, wherein said substituted phenyl is a phenyl radical that can be classified as one or more of the group comprising fluoro-substituted phenyl, alkyl-substituted phenyl, 2-substituted phenyl, 3-mono-substituted phenyl, 2,3-disubstituted phenyl, and di-substituted phenyl wherein two phenyl carbons are together substituted with an alkylene; and wherein each $R_8$ is independently aryl or substituted aryl. In some embodiments $R_6$ is an alkyl, alkylaminoalkyl, or alkylaminoacyl group selected from —$CH_2NHC(CH_3)_3$, —$CH_2CH(CH_3)_2$, —$CH(NH_2)CH(CH_3)CH_2CH_3$, —$CH(NH_2)CH(CH_3)_2$, —$CH(CH_2C_6H_5)NHC(=O)CH_2NH_2$, —$CH_2CH_2NHC(=O)C_6H_5$, and —$CH_2CH_2NHC(=O)CH_2C_6H_6$.

In some embodiments, $R_6$ is 2-fluorophenyl or 4-fluorophenyl. In some embodiments, $R_6$ is heteroaryl or substituted heteroaryl, wherein the heteroaryl group is selected from pyridyl, pyrimidinyl, pyridazinyl, oxazolyl, furanyl, triazolyl, triazinyl, benzofuranyl, thiophenyl, pyrrolyl, imidazoyl, thiazoyl, quinolinyl, isoquinolinyl, benzooxazolyl, and benzothiazolyl. When $R_6$ is substituted heteroaryl, the heteroaryl ring can be substituted by one or more substituents selected from halo, nitro, hydroxy, amino, alkylamino, arylamino, alkyl, alkoxyl, substituted alkyl (e.g., perhaloalkyl), perhaloalkoxy, aralkyl, aralkoxy, aryl, aryloxy, substituted aryl, carboxyl, acyl, and amido. For example the heteroaryl substituent can be fluoro, chloro, bromo, methyl, methoxy, $NH_2$, $NO_2$, trifluoromethoxy, phenyl, substituted phenyl (e.g., halo-substituted phenyl) or trifluoromethyl, and the like.

In some embodiments, $R_6$ is a diarylmethylene group having the structure: $—C(R_8)_2$, wherein each $R_8$ group is independently aryl or substituted aryl. Thus, $R_8$ can be phenyl or heteroaryl (such as one of the heteroaryl groups described above for $R_6$), substituted phenyl, or substituted heteroaryl. In some embodiments, both $R_8$ groups are phenyl.

In some embodiments, $R_6$ has the structure $—CH_2R_7$ and the compound of Formula (I) is a compound of Formula (Ia):

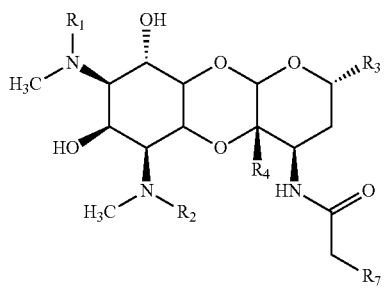

wherein:

$R_1$ and $R_2$ are each independently H, alkoxycarbonyl, or aralkoxycarbonyl;

$R_3$ is alkyl;

$R_4$ is H, hydroxy, alkyl, or alkoxy; and $R_7$ is selected from the group comprising aralkyl, substituted aralkyl, heteroaryl, substituted heteroaryl, and substituted phenyl, wherein said substituted phenyl can be classified as one or more of fluoro-substituted phenyl, alkyl-substituted phenyl, 2-substituted phenyl, 3-mono-substituted phenyl, 2,3-di-substituted phenyl, and di-substituted phenyl wherein two phenyl carbons are together substituted with an alkylene; or a pharmaceutically acceptable salt or a prodrug thereof.

In some embodiments, $R_7$ is substituted phenyl selected from the group comprising 4-fluorophenyl, 4-methylphenyl, 3-methylphenyl, 3-methoxyphenyl, 2-methoxyphenyl, 3,4-methylenedioxyphenyl, and 2,3-difluorophenyl.

In some embodiments, $R_7$ is heteroaryl or substituted heteroaryl comprising a heteroaryl group selected from the group comprising pyridyl, triazolyl, triazinyl, pyrimidinyl, pyridazinyl, oxazolyl, furanyl, benzofuranyl, thiophenyl, pyrrolyl, imidazoyl, thiazoyl, quinolinyl, isoquinolinyl, benzooxazolyl, and benzothiazolyl. In some embodiments, $R_7$ comprises heteroaryl selected from pyridyl, thiazoyl, benzooxazolyl, and benzothiazolyl.

In some embodiments, $R_7$ is substituted heteroaryl, wherein the heteroaryl is substituted with one or more of the group comprising amino, alkylamino, arylamino, nitro, halo, hydroxy, carboxyl, acyl, alkyl, substituted alkyl (e.g., perhaloalkyl), alkoxy, perhaloalkoxy, aralkyl, aryl, aryloxy, and substituted aryl. Thus, the $R_7$ heteroaryl group can be substituted with one or more fluoro, chloro, bromo, methoxy, methyl, $NO_2$, trifluoromethoxy, phenylamino, phenyl, or trifluoromethyl groups. In some embodiments, the $R_7$ heteroaryl group is substituted with an aryl or aryl containing group such that the $R_7$ group as a whole is biaryl (i.e., the $R_7$ heteroaryl group is directly attached to another aryl or substituted aryl group or attached to the other aryl or substituted aryl group via a linker such as alkylene (e.g., methylene), $—O—$, $—C(=O)—$, or $—NH—$). The aryl containing group attached to the $R_7$ heteroaryl group can be, for example, phenyl, benzyl, phenoxy, benzoyl, halo-substituted phenyl (e.g., p-fluorophenyl), alkoxy-substituted phenyl (e.g., m-methoxyphenyl) and the like or a phenylamino or substituted phenylamino group (e.g, halo-, alkyl-, alkoxy-, perhaloalkyl-, or perhaloalkoxy-substituted phenylamino).

In some embodiments, $R_7$ is an aralkyl or substituted aralkyl group that comprises a heteroaryl or substituted heteroaryl group. In some embodiments, the aralkyl or substituted aralkyl group can comprise a heteroaryl selected from the group comprising pyridyl, triazolyl, triazinyl, pyrimidinyl, pyridazinyl, oxazolyl, furanyl, benzofuranyl, thiophenyl, pyrrolyl, imidazoyl, thiazoyl, quinolinyl, isoquinolinyl, benzooxazolyl, and benzothiazolyl. In some embodiments, $R_7$ is aralkyl or substituted aralkyl comprising pyridyl, thiazoyl, benzooxazolyl, or benzothiazolyl. The heteroaryl moiety of the aralkyl group can be substituted with one or more of the group comprising amino, alkylamino, arylamino, nitro, halo, hydroxy carboxyl, acyl, alkyl, substituted alkyl (e.g., perhaloalkyl), alkoxy, perhaloalkoxy, aralkyl, aryl, aryloxy, and substituted aryl. For example, the heteroaryl group can be substituted with one or more fluoro, chloro, bromo, methoxy, methyl, $NO_2$, trifluoromethoxy, phenylamino, phenyl, or trifluoromethyl groups. In addition, the alkyl moiety of the aralkyl $R_7$ group can also be substituted, e.g., with an alkyl, acyl, amino, acylamino, halo, hydroxy or other alkyl group substituent.

In some embodiments, $R_7$ is a nitrogen-containing heteroaryl group, optionally substituted by one or more aryl group substituents. In some embodiments, at least one nitrogen atom in the nitrogen-containing heteroaryl group is positioned adjacent (i.e., in the 2-position) to the atom attached directly to the acyl methylene group of the structure of Formula (Ia). In some embodiments, the compound of Formula (Ia) is a compound of Formula (Ib), (Ic), or (Id):

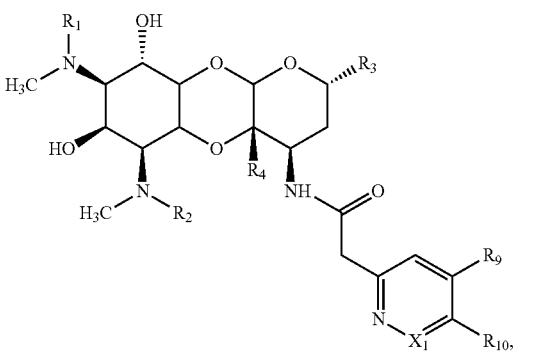

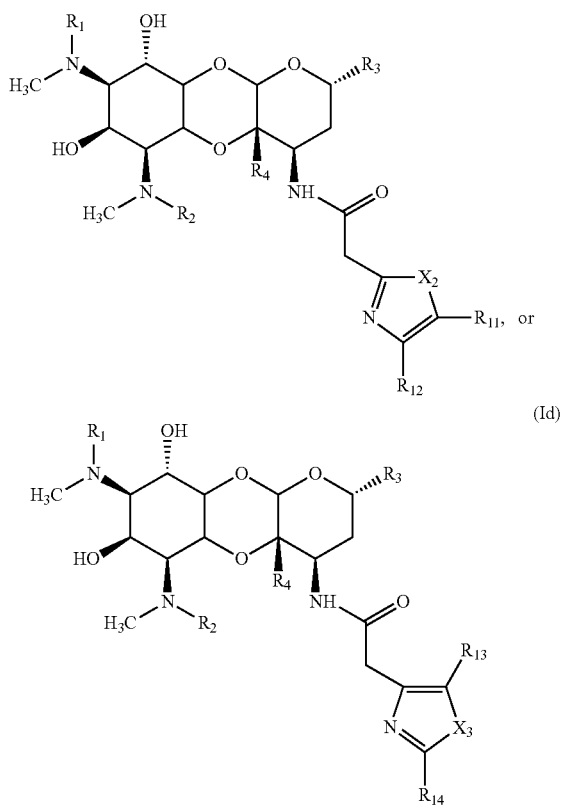

wherein:

R$_1$ and R$_2$ are each independently H, alkoxycarbonyl, or aralkoxycarbonyl;

R$_3$ is alkyl;

R$_4$ is H, hydroxy, alkyl, or alkoxy;

X$_1$ is CH or N;

X$_2$ and X$_3$ are O, S, or NH;

R$_9$, R$_{10}$, R$_{11}$, R$_{12}$, R$_{13}$, and R$_{14}$ are independently selected from the group comprising H, halo, hydroxy, nitro, N(R$_{15}$)$_2$, alkyl, substituted alkyl, alkoxy, perhaloalkoxy, aralkyl, substituted aralkyl, aralkoxy, aryl (e.g., phenyl or heteroaryl), aryloxy, acyl (e.g., aroyl), and substituted aryl (e.g., substituted heteroaryl or substituted phenyl); or wherein R$_9$ and R$_{10}$ together or R$_{11}$ and R$_{12}$ together are alkylene (e.g., —CH═CH—CH═CH—); and wherein each R$_{15}$ is independently selected from the group comprising H, alkyl, substituted alkyl, aralkyl, substituted aralkyl, aryl (e.g., phenyl or heteroaryl), and substituted aryl (e.g., substituted phenyl or substituted heteroaryl);

or a pharmaceutically acceptable salt or a prodrug thereof.

In some embodiments, at least one of R$_9$, R$_{10}$, R$_{11}$, R$_{12}$, R$_{13}$, and R$_{14}$ is N(R$_{15}$)$_2$, for example, wherein one R$_{15}$ is aryl or substituted aryl. In some embodiments, at least one of R$_9$, R$_{10}$, R$_{11}$, R$_{12}$, R$_{13}$, and R$_{14}$ is aryl or substituted aryl.

In some embodiments, the compound is a compound of Formula (Ib), wherein X$_1$ is CH and wherein R$_{10}$ is other than H (e.g., wherein R$_{10}$ is selected from aryl, substituted aryl, halo or nitro). In some embodiments, the compound is a compound of Formula (Id), wherein X$_3$ is S and R$_{13}$ is H. In some embodiments, R$_{14}$ is N(R$_{15}$)$_2$.

In some embodiments, the compound of Formula (I) is selected from the group comprising:

3'-dihydro-3'-deoxy-4(R)-(3-pyridin-3-yl)propionylamino spectinomycin (1299);
3'-dihydro-3'-deoxy-4(R)-(pyridin-2-yl)acetylamino spectinomycin (1329);
3'-dihydro-3'-deoxy-4(R)-4-fluorobenzoylamino spectinomycin (1364);
3'-dihydro-3'-deoxy-4(R)-furan-2-carboxylicamino spectinomycin (1365);
3'-dihydro-3'-deoxy-4(R)-(4-fluorophenyl)acetylamino spectinomycin (1367);
3'-dihydro-3'-deoxy-4(R)-(pyridin-3-yl)acetylamino spectinomycin (1368);
3'-dihydro-3'-deoxy-4(R)-pyridin-2-carboxylicamino spectinomycin (1370);
3'-dihydro-3'-deoxy-4(R)-p-tolylacetylamino spectinomycin (1399);
3'-dihydro-3'-deoxy-4(R)-(3-methoxy-phenyl)acetylamino spectinomycin (1400);
3'-dihydro-3'-deoxy-4(R)-[3,4-(methylene dioxy)phenyl]acetylamino spectinomycin (1411);
3'-dihydro-3'-deoxy-4(R)-m-tolylacetylamino spectinomycin (1412);
3'-dihydro-3'-deoxy-4(R)-(pyridin-4-yl)acetylamino spectinomycin (1413);
3'-dihydro-3'-deoxy-4(R)-(pyrimidin-2-yl)acetylamino spectinomycin (1439);
3'-dihydro-3'-deoxy-4(R)-(thiazol-4-yl)acetylamino spectinomycin (1443);
3'-dihydro-3'-deoxy-4(R)-(2-aminothiazol-4-yl)acetylamino spectino-mycin (1444);
3'-dihydro-3'-deoxy-4(R)-(5-fluoropyridin-2-yl) acetylamino spectinomycin (1445);
3'-dihydro-3'-deoxy-4(R)-(2,3-difluorophenyl)acetylamino spectinomycin (1447);
3'-dihydro-3'-deoxy-4(R)-(2-methoxyphenyl)acetylamino spectinomycin (1448)
3'-dihydro-3'-deoxy-4(R)-(pyridazin-3-yl)acetylamino spectinomycin (1449);
3'-dihydro-3'-deoxy-4(R)-(pyrazine-2-yl)carboxylicamino spectinomycin (1453);
3'-dihydro-3'-deoxy-4(R)-(benzooxazol-2-yl)acetylamino spectinomycin (1465);
3'-dihydro-3'-deoxy-4(R)-(1H-imidazol-4-yl)acetylamino spectinomycin (1466);
3'-dihydro-3'-deoxy-4(R)-[3(R)-amino-3-(4-fluorophenyl)]propanoylamino spectinomycin (1487);
3'-dihydro-3'-deoxy-4(R)-(thiazol-2-yl)acetylamino spectinomycin (1489);
3'-dihydro-3'-deoxy-4(R)-(5-nitropyridin-2-yl)acetylamino spectinomycin (1490);
3'-dihydro-3'-deoxy-4(R)-(benzothiazol-2-yl)acetylamino spectinomycin (1491);
3'-dihydro-3'-deoxy-4(R)-(2-fluorobenzene-1-yl)carboxylicamino spectinomycin (1492);
3'-dihydro-3'-deoxy-4(R)-(2,2-diphenyl)acetylamino spectinomycin (1514);
3'-dihydro-3'-deoxy-4(R)-(5-bromopyridin-2-yl)acetylamino spectinomycin (1516);
3'-dihydro-3'-deoxy-4(R)-(2-phenylthiazol-4-yl)acetylamino spectinomycin (1517);
3'-dihydro-3'-deoxy-4(R)-(pyridin-2-yl)propanoylamino spectinomycin (1518);
3'-dihydro-3'-deoxy-4(R)-(5-phenylpyridin-2-yl)acetylamino spectinomycin (1519);
3'-dihydro-3'-deoxy-4(R)-(2-(phenylamino)thiazol-4-yl)acetylamino spectinomycin (1520);

3'-Dihydro-3'-deoxy-4(R)-(5-(4-chlorophenyl)pyridin-2-yl)acetylamino spectinomycin (1535);
3'-Dihydro-3'-deoxy-4(R)-(quinoline-8-yl)carbonylamino spectinomycin (1536);
3'-Dihydro-3'-deoxy-4(R)-2-(1-benzyl-1H-1,2,3-triazol-4-yl)acetylamino spectinomycin (1537);
3'-Dihydro-3'-deoxy-4(R)-(2-((4-fluorophenyl)amino)thiazol-4-yl)acetylamino spectinomycin (1538);
3'-Dihydro-3'-deoxy-4(R)-(2-((3-fluorophenyl)amino)thiazol-4-yl)acetylamino spectinomycin (1539);
3'-Dihydro-3'-deoxy-4(R)-(2-((4-(trifluoromethoxy)phenyl)amino)thiazol-4-yl)acetylamino spectinomycin (1540);
3'-Dihydro-3'-deoxy-4(R)-(2-((4-(trifluoromethyl)phenyl)amino)thiazol-4-yl)acetylamino spectinomycin (1541);
3'-Dihydro-3'-deoxy-4(R)-(5-(4-fluorophenyl)pyridin-2-yl)acetylamino spectinomycin (1542);
3'-Dihydro-3'-deoxy-4(R)-(5-(3-methoxyphenyl)pyridin-2-yl)acetylamino spectinomycin (1543);
3'-Dihydro-3'-deoxy-4(R)-(4-chloropyridin-2-yl)acetylamino spectinomycin (1544);
3'-dihydro-3'-deoxy-4(R)-(tert-butylamino)acetylamino spectinomycin (1351);
3'-dihydro-3'-deoxy-4(R)-(3-methyl)butanoylamino spectinomycin (1369);
3'-dihydro-3'-deoxy-4(R)-[(2S,3S)-2-amino-3-methyl]pentanoylamino spectinomycin (1485);
3'-dihydro-3'-deoxy-4(R)-[2(S)-amino-3-methyl]butanoylamino spectinomycin (1486);
3'-dihydro-3'-deoxy-4(R)-[2(S)-(2-aminoacetamido)-3-phenyl]propanoyl-amino spectinomycin (1502);
3'-dihydro-3'-deoxy-4(R)-3-benzamido propanoylamino spectinomycin (1503); and
3'-dihydro-3'-deoxy-4(R)-3-(2-phenylacetamido)propanoylamino spectinomycin (1504);
or a pharmaceutically acceptable salt or prodrug thereof.

In some embodiments, the compound of Formula (I) has increased cellular uptake into *Mycobacterium tuberculosis*, another bacteria, or infected host tissues as compared to spectinomycin. In some embodiments, the compound has superior bioavailability after oral administration as compared to spectinomycin. In some embodiments, the compound has increased affinity to the *Mycobacterium tuberculosis* 30S ribosome as compared to spectinomycin. In some embodiments, the compound has decreased susceptibility to extrusion by drug efflux mechanisms as compared to spectinomycin.

IV. Prodrugs

In representative embodiments, compounds disclosed herein are prodrugs. A prodrug means a compound that, upon administration to a recipient, is capable of providing (directly or indirectly) a compound of the presently disclosed subject matter or an active metabolite or residue thereof. Prodrugs can increase the bioavailability of the compounds of the presently disclosed subject matter when such compounds are administered to a subject (e.g., by allowing an orally administered compound to be more readily absorbed into the blood) or can enhance the delivery of the compound to a particular biological compartment (e.g., cell, tissue, biological system).

Prodrugs of the presently disclosed compounds can include esters formed from the reaction of one of the hydroxyl groups of a compound of Formula (I), (Ia), (Ib), (Ic), and/or (Id) with an acyl halide, anhydride or activated ester (e.g., a pentafluorophenyl ester). The ester of the prodrug can be cleaved in vivo by an esterase present in plasma or in a tissue or can be hydrolyzed under aqueous conditions at a physiological pH. Prodrugs of the presently disclosed compounds can also be formed by derivatizing an amino or hydroxyl group of a compound of Formula (I), (Ia), (Ib), (Ic), and/or (Id) to form a carbamate, carbonate, phosphate ester, azo group or amide that is cleavable under physiological conditions (e.g., at a certain pH or by an enzyme).

V. Pharmaceutically Acceptable Salts

The compounds described herein can be administered as pharmaceutically acceptable salts. Pharmaceutically acceptable salts are described, for example, in Berge et al., (*J. Pharm. Sci.*, 66(1), 1-19 (1977)), incorporated herein by reference in its entirety. The term "pharmaceutically acceptable" can refer to salts (or carriers) that are pharmaceutically acceptable in humans.

Pharmaceutically acceptable salts include, but are not limited to, the gluconate, lactate, acetate, tartarate, citrate, phosphate, maleate, borate, nitrate, sulfate, and hydrochloride salts. The salts of the compounds described herein can be prepared, for example, by reacting the base compound with the desired acid in solution. After the reaction is complete, the salts are crystallized from solution by the addition of an appropriate amount of solvent in which the salt is insoluble. In some embodiments, the hydrochloride salt is made by passing hydrogen chloride gas into an ethanolic solution of the free base. In some embodiments, the pharmaceutically acceptable salt is a hydrochloride or hydrobromide salt.

VI. Methods for Treating Microbial Infections

In some embodiments, the presently disclosed subject matter is related to a method of treating a microbial infection in a subject in need of treatment thereof wherein the method comprises administering to the subject a spectinomycin derivative (e.g., a compound of Formula (I), (Ia), (Ib), (Ic), and/or (Id), or a prodrug and/or pharmaceutically acceptable salt thereof).

Infections treatable by the presently disclosed subject matter can be caused by a variety of microbes, including fungi, algae, protozoa, bacteria, and viruses. In some embodiments, the infection is a bacterial infection. Exemplary microbial infections that can be treated by the method of the presently disclosed subject matter include, but are not limited to, infections caused by *Staphylococcus aureaus, Enterococcus faecalis, Bacillus anthracis*, a *Streptococcus* species (e.g., *Streptococcus pyogenes* and *Streptococcus pneumoniae*), *Escherichia coli, Pseudomonas aeruginosa, Burkholderia cepacia*, a *Proteus* species (e.g., *Proteus mirabilis* and *Proteus vulgaris*), *Klebsiella pneumoniae, Acinetobacter baumannii, Strenotrophomonas maltophillia, Mycobacterium tuberculosis, Mycobacterium bovis*, other mycobacteria of the tuberculosis complex, and non-tuberculous mycobacteria, including *Mycobacterium ulcerans*.

The methods of the presently disclosed subject matter are useful for treating these conditions in that they inhibit the onset, growth, or spread of the condition, cause regression of the condition, cure the condition, or otherwise improve the general well-being of a subject afflicted with, or at risk of, contracting the condition. Thus, in accordance with the presently disclosed subject matter, the terms "treat", "treating", and grammatical variations thereof, as well as the phrase "method of treating", are meant to encompass any desired therapeutic intervention, including but not limited to a method for treating an existing infection in a subject, and a method for the prophylaxis (i.e., preventing) of infection, such as in a subject that has been exposed to a microbe as disclosed herein or that has an expectation of being exposed to a microbe as disclosed herein.

In some embodiments, the spectinomycin derivative is provided in a pharmaceutical formulation for oral, intravenous, intramuscular, nasal, or topical administration. Thus, in some embodiments, the formulation can be prepared in a dosages form, such as but not limited to, a tablet, capsule, liquid (solution or suspension), suppository, ointment, cream, or aerosol. In some embodiments, the presently disclosed subject matter provides such compounds and/or formulations that have been lyophilized and that can be reconstituted to form pharmaceutically acceptable formulations for administration, for example, as by intravenous or intramuscular injection.

In some embodiments, the spectinomycin derivative is administered to the subject before, after, or at the same time as one or more additional therapeutic compounds. The additional therapeutic compound can be a known antimicrobial compound or a therapeutic that reduces pain and/or fever (e.g., an anti-inflammatory compound). For example, the additional therapeutic compound can be an antibiotic, such as a penicillin, e.g., penicillin G, penicillin V, methicillin, oxacillin, carbenicillin, nafcillin, ampicillin, etc.; a cephalosporin, e.g., cefaclor, cefazolin, cefuroxime, moxalactam, etc.; a carbapenem; a monobactam; a tetracycline; a macrolide; a lincomycin; a polymyxin; a sulfonamide; a quinolone; cloramphenical; metronidazole; trimethoprim; vancomycin; streptomycin; etc. In some embodiments, the additional compound is a known anti-tuberculosis compound, such as, but not limited to, isoniazid, ethambutol, and rifampin (i.e., rifampicin).

In some embodiments, the spectinomycin derivative is selectively active against a particular type of bacterial infection. For example, in some embodiments, the compound is selectively active against *Mycobacterium tuberculosis, Bacillus anthracis, Enterococcus faecalis, Streptococcus pneumoniae, Acintobacter baumannii,* or *Strenotrophomonas maltophiffia.* By "selectively active" is meant that the compound shows greater activity against a particular type of infection than against other types of infections. In some embodiments, the compound is 2, 5, 10, 20, 50, 100 or more times as active against one type of infection than it is against another type of infection as measured by minimum inhibitory concentration (MIC).

In some embodiments, the microbial infection comprises an infection caused by mycobacteria including the organism *Mycobacterium tuberculosis.* In some embodiments, the infection is caused by a multi-drug resistant strain of *Mycobacterium tuberculosis.* The infection can also be caused by other mycobacteria, as well, including, but not limited to *M. bovis,* another mycobacterium of the tuberculosis complex (e.g., *M. africanum, M. canetti, M. micron*), or a non-tuberculous mycobacteria, such as, but, not limited to *M. ulcerans, M. avium intracellulare, M. kansasii, M. fortuitum, M. chelonae, M. leprae.*

In some embodiments, the specintomycin derivative is administered to a subject with an existing microbial infection. In some embodiments, the spectinomycin derivative is administered prophylactically to prevent a microbial infection or to prevent the recurrence of a microbial infection. Thus, in some embodiments, the spectinomycin derivative is administered prophylactically to prevent or reduce the incidence of one of: (a) a microbial infection in a subject at risk of infection; (b) a recurrence of the microbial infection; and (c) combinations thereof.

In some embodiments, the presently disclosed subject matter provides a method of treating a bacterial infection in a subject in need of treatment thereof, wherein the method comprises administering to the subject a compound of Formula (I):

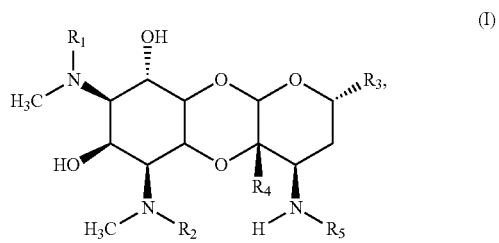

wherein:
$R_1$ and $R_2$ are each independently H, alkoxycarbonyl, or aralkoxycarbonyl;
$R_3$ is alkyl;
$R_4$ is H, hydroxy, alkyl, or alkoxy; and
$R_5$ is selected from the group consisting of alkyl, substituted alkyl, aralkyl, substituted aralkyl, aryl, substituted aryl, and acyl;
or a pharmaceutically acceptable salt or a prodrug thereof.

In some embodiments, $R_1$ and $R_2$ are each H. In some embodiments, $R_3$ is a $C_1$-$C_8$ alkyl group (e.g., methyl, ethyl, or a branched, straight-chain or cyclic propyl, butyl, pentyl, hexyl, heptyl, or octyl). In some embodiments, $R_3$ is methyl or butyl (e.g., n-butyl). In some embodiments, $R_4$ is selected from H, OH, methyl and methoxy. In some embodiments, $R_4$ is hydroxy.

In some embodiments, the compound of Formula (I) is a spectinamide (i.e., wherein $R_5$ is acyl). In some embodiments, $R_5$ is —C(=O)$R_6$, wherein $R_6$ is selected from the group comprising alkyl, substituted alkyl, aralkyl, substituted aralkyl, aryl and substituted aralkyl. In some embodiments, $R_5$ is —C(=O)$R_6$, wherein:

(a) $R_6$ is selected from the group comprising —CH$_2$NHC(CH$_3$)$_3$, —CH$_2$CH(CH$_3$)$_2$, —CH(NH$_2$)CH(CH$_3$)CH$_2$CH$_3$, —CH(NH$_2$)CH(CH$_3$)$_2$, —CH(CH$_2$C$_6$H$_5$)NHC(=O)CH$_2$NH$_2$, —CH$_2$CH$_2$NHC(=O)C$_6$H$_5$, and —CH$_2$CH$_2$NHC(=O)CH$_2$C$_6$H$_6$; or (b) $R_6$ is selected from the group comprising heteroaryl, substituted heteroaryl, 2-substituted phenyl, 4-halo-substituted phenyl, —CH$_2$R$_7$, and —C(R$_8$)$_2$; wherein $R_7$ is selected from the group comprising aralkyl, substituted aralkyl, heteroaryl, substituted heteroaryl, and substituted phenyl, wherein said substituted phenyl is selected from the group comprising fluoro-substituted phenyl, alkyl-substituted phenyl, 2-substituted phenyl, 3-mono-substituted phenyl, 2,3-di-substituted phenyl, and di-substituted phenyl wherein two phenyl carbons are together substituted with an alkylene; and each $R_8$ is independently aryl or substituted aryl;
or a pharmaceutically acceptable salt or a prodrug thereof.

In some embodiments, $R_6$ is 2-fluorophenyl or 4-fluorophenyl. In some embodiments, $R_6$ is heteroaryl or substituted heteroaryl, wherein the heteroaryl group is selected from the group comprising pyridyl, pyrimidinyl, pyridazinyl, oxazolyl, furanyl, triazolyl, triazinyl, benzofuranyl, thiophenyl, pyrrolyl, imidazoyl, thiazoyl, quinolinyl, isoquinolinyl, benzooxazolyl, and benzothiazolyl. When $R_6$ is substituted heteroaryl, the heteroaryl ring can be substituted by one or more substituents selected from halo, nitro, hydroxy, amino, alkylamino, arylamino, alkyl, alkoxyl, substituted alkyl (e.g., perhaloalkyl), perhaloalkoxy, aralkyl, aralkoxy, aryl, aryloxy, substituted aryl, carboxyl, acyl, and amido. For example the heteroaryl substituent can be fluoro, chloro, bromo, methyl, methoxy, NH$_2$, NO$_2$, trifluoromethoxy, phenyl, substituted phenyl, or trifluuoromethyl, and the like.

In some embodiments, R$_6$ is a diarylmethylene group having the structure: —C(R$_8$)$_2$, wherein each R$_8$ group is independently aryl or substituted aryl. Thus, R$_8$ can be phenyl or heteroaryl (such as one of the heteroaryl groups described above for R$_6$), substituted phenyl, or substituted heteroaryl. In some embodiments, both R$_8$ groups are phenyl.

In some embodiments, R$_6$ has the structure —CH$_2$R$_7$ and the compound of Formula (I) is a compound of Formula (Ia):

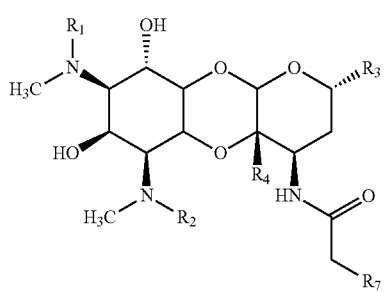

wherein:
R$_1$ and R$_2$ are each independently H, alkoxycarbonyl, or aralkoxycarbonyl;
R$_3$ is alkyl;
R$_4$ is H, hydroxy, alkyl, or alkoxy; and
R$_7$ is selected from the group comprising aralkyl, substituted aralkyl, heteroaryl, substituted heteroaryl, and substituted phenyl, wherein said substituted phenyl is selected from the group comprising fluoro-substituted phenyl, alkyl-substituted phenyl, 2-substituted phenyl, 3-mono-substituted phenyl, 2,3-di-substituted phenyl, and di-substituted phenyl wherein two phenyl carbons are together substituted with an alkylene; or a pharmaceutically acceptable salt or a prodrug thereof.

In some embodiments, R$_7$ is substituted phenyl selected from the group comprising 4-fluorophenyl, 4-methylphenyl, 3-methylphenyl, 3-methoxyphenyl, 2-methoxyphenyl, 3,4-methylenedioxyphenyl, and 2,3-difluorophenyl.

In some embodiments, R$_7$ is heteroaryl or substituted heteroaryl comprising a heteroaryl group selected from the group comprising pyridyl, triazolyl, triazinyl, pyrimidinyl, pyridazinyl, oxazolyl, furanyl, benzofuranyl, thiophenyl, pyrrolyl, imidazoyl, thiazoyl, quinolinyl, isoquinolinyl, benzooxazolyl, and benzothiazolyl. In some embodiments, R$_7$ comprises heteroaryl selected from pyridyl, thiazoyl, benzooxazolyl, and benzothiazolyl.

In some embodiments, R$_7$ is substituted heteroaryl, wherein the heteroaryl is substituted with one or more of the group comprising amino, alkylamino, arylamino, nitro, halo, hydroxy, carboxyl, acyl, alkyl, substituted alkyl (e.g., perhaloalkyl), alkoxy, perhaloalkoxy, aralkyl, aryl, aryloxy, and substituted aryl. For example, the R$_7$ heteroaryl group can be substituted with one or more fluoro, chloro, bromo, methoxy, methyl, NO$_2$, trifluoromethoxy, phenylamino, phenyl, or trifluoromethyl groups. In some embodiments, the R$_7$ heteroaryl group is substituted with an aryl or aryl-containing group such that the R$_7$ group as a whole is biaryl (i.e., the R$_7$ heteroaryl group is directly attached to another aryl or substituted aryl group or attached to the other aryl or substituted aryl group via a linker such as alkylene (e.g., methylene), —O—, —C(═O)—, or —NH—). The aryl-containing group attached to the R$_7$ heteroaryl group can be, for example, phenyl, benzyl, phenoxy, benzoyl, halo-substituted phenyl (e.g., p-fluorophenyl), alkoxy-substituted phenyl (e.g., m-methoxyphenyl) and the like or a phenylamino or substituted phenylamino group (e.g. halo-, alkyl-, alkoxy-, perhaloalkyl-, or perhaloalkoxy-substituted phenylamino).

In some embodiments, R$_7$ is an aralkyl or substituted aralkyl group that comprises a heteroaryl or substituted heteroaryl group. In some embodiments, the aralkyl or substituted aralkyl group can comprise a heteroaryl selected from the group comprising pyridyl, triazolyl, triazinyl, pyrimidinyl, pyridazinyl, oxazolyl, furanyl, benzofuranyl, thiophenyl, pyrrolyl, imidazoyl, thiazoyl, quinolinyl, isoquinolinyl, benzooxazolyl, and benzothiazolyl. In some embodiments, R$_7$ is aralkyl or substituted aralkyl comprising pyridyl, thiazoyl, benzooxazolyl, or benzothiazolyl. The heteroaryl moiety of the aralkyl group can be substituted with one or more of the group comprising amino, alkylamino, arylamino, nitro, halo, hydroxy, carboxyl, acyl, alkyl, substituted alkyl (e.g., perhaloalkyl), alkoxy, perhaloalkoxy, aralkyl, aryl, aryloxy, and substituted aryl. For example, the heteroaryl group can be substituted with one or more fluoro, chloro, bromo, methoxy, methyl, NO$_2$, trifluoromethoxy, phenylamino, phenyl, or trifluoromethyl groups. In addition, the alkyl moiety of the aralkyl R$_7$ group can also be substituted, e.g., with an alkyl, acyl, amino, acylamino, halo, hydroxy or other alkyl group substituent.

In some embodiments, R$_7$ is a nitrogen-containing heteroaryl group, optionally substituted by one or more aryl group substituents. In some embodiments, at least one nitrogen atom in the nitrogen-containing heteroaryl group is positioned adjacent (i.e., in the 2-position) to the atom attached directly to the acyl methylene group of the structure of Formula (Ia). In some embodiments, the compound of Formula (Ia) is a compound of Formula (Ib), (Ic), or (Id):

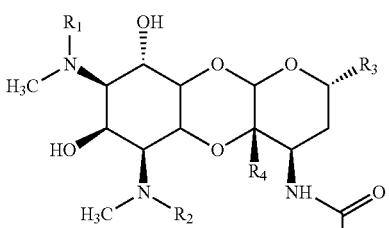

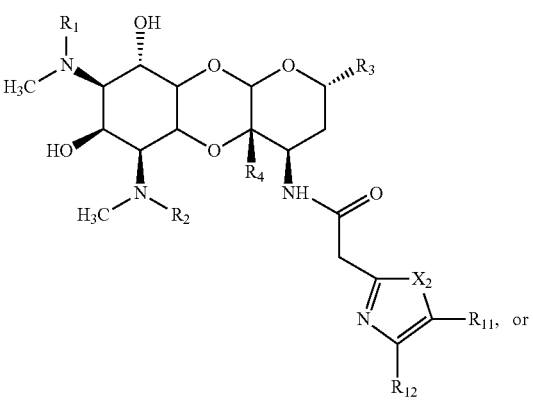

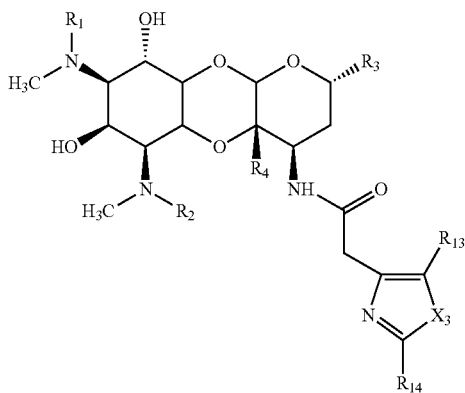

wherein:

R$_1$ and R$_2$ are each independently H, alkoxycarbonyl, or aralkoxycarbonyl;
R$_3$ is alkyl;
R$_4$ is H, hydroxy, alkyl, or alkoxy;
X$_1$ is CH or N;
X$_2$ and X$_3$ are O, S, or NH;
R$_9$, R$_{10}$, R$_{11}$, R$_{12}$, R$_{13}$, and R$_{14}$ are independently selected from the group comprising H, halo, hydroxy, nitro, N(R$_{15}$)$_2$, alkyl, substituted alkyl, alkoxy, perhaloalkoxy, aralkyl, substituted aralkyl, aralkoxy, aryl (e.g., phenyl or heteroaryl), aryloxy, acyl (e.g., aroyl), and substituted aryl (e.g., substituted phenyl or substituted heteroaryl); or wherein R$_9$ and R$_{10}$ together or R$_{11}$ and R$_{12}$ together are alkylene (e.g., —CH═CH—CH═CH—); and wherein each R$_{15}$ is independently selected from the group comprising H, alkyl, substituted alkyl, aralkyl, substituted aralkyl, aryl (e.g, phenyl or heteroaryl), and substituted aryl (e.g., substituted phenyl or substituted heteroaryl);
or a pharmaceutically acceptable salt or a prodrug thereof.

In some embodiments, at least one of R$_9$, R$_{10}$, R$_{11}$, R$_{12}$, R$_{13}$, and R$_{14}$ is N(R$_{15}$)$_2$, for example, wherein one R$_{15}$ is aryl or substituted aryl. In some embodiments, at least one of R$_9$, R$_{10}$, R$_{11}$, R$_{12}$, R$_{13}$, and R$_{14}$ is aryl or substituted aryl.

In some embodiments, the compound is a compound of Formula (Ib), wherein X$_1$ is CH and wherein R$_{10}$ is other than H (e.g., wherein R$_{10}$ is selected from aryl, substituted aryl, halo or nitro). In some embodiments, the compound is a compound of Formula (Id), wherein X$_3$ is S and R$_{13}$ is H. In some embodiments, R$_{14}$ is N(R$_{15}$)$_2$.

In some embodiments, the compound of Formula (I) is selected from the group comprising:
3'-dihydro-3'-deoxy-4(R)-(3-pyridin-3-yl)propionylamino spectinomycin (1299);
3'-dihydro-3'-deoxy-4(R)-(pyridin-2-yl)acetylamino spectinomycin (1329);
3'-dihydro-3'-deoxy-4(R)-4-fluorobenzoylamino spectinomycin (1364);
3'-dihydro-3'-deoxy-4(R)-furan-2-carboxylicamino spectinomycin (1365);
3'-dihydro-3'-deoxy-4(R)-(4-fluorophenyl)acetylamino spectinomycin (1367);
3'-dihydro-3'-deoxy-4(R)-(pyridin-3-yl)acetylamino spectinomycin (1368);
3'-dihydro-3'-deoxy-4(R)-pyridin-2-carboxylicamino spectinomycin (1370);
3'-dihydro-3'-deoxy-4(R)-p-tolylacetylamino spectinomycin (1399);
3'-dihydro-3'-deoxy-4(R)-(3-methoxy-phenyl)acetylamino spectinomycin (1400);
3'-dihydro-3'-deoxy-4(R)-[3,4-(methylene dioxy)phenyl]acetylamino spectinomycin (1411);
3'-dihydro-3'-deoxy-4(R)-m-tolylacetylamino spectinomycin (1412);
3'-dihydro-3'-deoxy-4(R)-(pyridin-4-yl)acetylamino spectinomycin (1413);
3'-dihydro-3'-deoxy-4(R)-(pyrimidin-2-yl)acetylamino spectinomycin (1439);
3'-dihydro-3'-deoxy-4(R)-(thiazol-4-yl)acetylamino spectinomycin (1443);
3'-dihydro-3'-deoxy-4(R)-(2-aminothiazol-4-yl)acetylamino spectino-mycin (1444);
3'-dihydro-3'-deoxy-4(R)-(5-fluoropyridin-2-yl)acetylamino spectinomycin (1445);
3'-dihydro-3'-deoxy-4(R)-(2,3-difluorophenyl)acetylamino spectinomycin (1447);
3'-dihydro-3'-deoxy-4(R)-(2-methoxyphenyl)acetylamino spectinomycin (1448);
3'-dihydro-3'-deoxy-4(R)-(pyridazin-3-yl)acetylamino spectinomycin (1449);
3'-Dihydro-3'-deoxy-4(R)-(pyrazine-2-yl)carboxylicamino spectinomycin (1453);
3'-dihydro-3'-deoxy-4(R)-(benzooxazol-2-yl)acetylamino spectinomycin (1465);
3'-dihydro-3'-deoxy-4(R)-(1H-imidazol-4-yl)acetylamino spectinomycin (1466);
3'-dihydro-3'-deoxy-4(R)-[3(R)-amino-3-(4-fluorophenyl)]propanoylamino spectinomycin (1487);
3'-dihydro-3'-deoxy-4(R)-(thiazol-2-yl)acetylamino spectinomycin (1489);
3'-dihydro-3'-deoxy-4(R)-(5-nitropyridin-2-yl)acetylamino spectinomycin (1490);
3'-dihydro-3'-deoxy-4(R)-(benzothiazol-2-yl)acetylamino spectinomycin (1491);
3'-dihydro-3'-deoxy-4(R)-(5-bromopyridin-2-yl)acetylamino spectinomycin (1516);
3'-dihydro-3'-deoxy-4(R)-(2-phenylthiazol-4-yl)acetylamino spectinomycin (1517);
3'-dihydro-3'-deoxy-4(R)-(pyridin-2-yl)propanoylamino spectinomycin (1518);
3'-dihydro-3'-deoxy-4(R)-(5-phenylpyridin-2-yl)acetylamino spectinomycin (1519);
3'-dihydro-3'-deoxy-4(R)-(2-(phenylamino)thiazol-4-yl) acetylamino spectinomycin (1520);
3'-Dihydro-3'-deoxy-4(R)-(5-(4-chlorophenyl)pyridin-2-yl) acetylamino spectinomycin (1535);
3'-Dihydro-3'-deoxy-4(R)-(quinoline-8-yl)carbonylamino Spectinomycin (1536);
3'-Dihydro-3'-deoxy-4(R)-2-(1-benzyl-1H-1,2,3-triazol-4-yl)acetylamino spectinomycin (1537);
3'-Dihydro-3'-deoxy-4(R)-(2-((4-fluorophenyl)amino)thiazol-4-yl)acetylamino spectinomycin (1538);
3'-Dihydro-3'-deoxy-4(R)-(2-((3-fluorophenyl)amino)thiazol-4-yl)acetylamino spectinomycin (1539);
3'-Dihydro-3'-deoxy-4(R)-(2-((4-(trifluoromethoxy)phenyl)amino)thiazol-4-yl)acetylamino spectinomycin (1540);
3'-Dihydro-3'-deoxy-4(R)-(2-((4-(trifluoromethyl)phenyl)amino)thiazol-4-yl)acetylamino spectinomycin (1541);
3'-Dihydro-3'-deoxy-4(R)-(5-(4-fluorophenyl)pyridin-2-yl) acetylamino spectinomycin (1542);
3'-Dihydro-3'-deoxy-4(R)-(5-(3-methoxyphenyl)pyridin-2-yl)acetylamino spectinomycin (1543);
3'-Dihydro-3'-deoxy-4(R)-(4-chloropyridin-2-yl)acetylamino spectinomycin (1544);

3'-dihydro-3'-deoxy-4(R)-(tert-butylamino)acetylamino spectinomycin (1351);

3'-dihydro-3'-deoxy-4(R)-(3-methyl)butanoylamino spectinomycin (1369);

3'-dihydro-3'-deoxy-4(R)-[(2S,3S)-2-amino-3-methyl]pentanoylamino spectinomycin (1485);

3'-dihydro-3'-deoxy-4(R)-[2(S)-amino-3-methyl]butanoylamino spectinomycin (1486);

3'-dihydro-3'-deoxy-4(R)-cyclopropylmethylamino spectinomycin (1419);

3'-dihydro-3'-deoxy-4(R)-furan-2-yl-methylamino spectinomycin (1422);

3'-dihydro-3'-deoxy-4(R)-(3-methoxy)benzylamino spectinomycin (1423);

3'-dihydro-3'-deoxy-4(R)-(4-fluoro)benzylamino spectinomycin (1424); and

3'-dihydro-3'-deoxy-4(R)-2-phenylethylamino spectinomycin (1450);

or a pharmaceutically acceptable salt or prodrug thereof.

In some embodiments, the compound is administered orally, topically, intravenously, or via inhalation. In some embodiments, an additional therapeutic compound is administered to the subject prior to, after, or during administration of the compound of Formula (I).

In some embodiments, the infection is an infection of a gram-positive bacterium, such as, but not limited to, a mycobacterial infection, a *Bacillus anthracis* infection, *Enterococcus faecalis* and a *Streptococcus pneumoniae* infection.

In some embodiments, the infection is a *Bacillus anthracis* infection and the compound of Formula (I) is selected from the group comprising 3'-dihydro-3'-deoxy-4(R)-(pyridin-3-yl)acetylamino spectinomycin (1368), 3'-dihydro-3'-deoxy-4(R)-(thiazol-4-yl)acetylamino spectinomycin (1443), or 3'-dihydro-3'-deoxy-4(R)-(2-aminothiazol-4-yl)acetylamino spectinomycin (1444).

In some embodiments, the infection is a *Streptococcus pneumoniae* infection and the compound of Formula (I) is selected from the group comprising:

3'-dihydro-3'-deoxy-4(R)-(pyridin-2-yl)acetylamino spectinomycin (1329);

3'-dihydro-3'-deoxy-4(R)-(benzooxazol-2-yl)acetylamino spectinomycin (1465);

3'-dihydro-3'-deoxy-4(R)-(1H-imidazol-4-yl)acetylamino spectinomycin (1466);

3'-dihydro-3'-deoxy-4(R)-[3(R)-amino-3-(4-fluorophenyl)]propanoylamino spectinomycin (1487);

3'-dihydro-3'-deoxy-4(R)-(thiazol-2-yl)acetylamino spectinomycin (1489);

3'-dihydro-3'-deoxy-4(R)-(5-nitropyridin-2-yl)acetylamino spectinomycin (1490);

3'-dihydro-3'-deoxy-4(R)-(benzothiazol-2-yl)acetylamino spectinomycin (1491);

3'-dihydro-3'-deoxy-4(R)-(pyrimidin-2-yl)acetylamino spectinomycin (1439);

3'-dihydro-3'-deoxy-4(R)-(5-bromopyridin-2-yl)acetylamino spectinomycin (1516);

3'-dihydro-3'-deoxy-4(R)-(2-phenylthiazol-4-yl)acetylamino spec-tinomycin (1517);

3'-dihydro-3'-deoxy-4(R)-(pyridin-2-yl)propanoylamino spectinomycin (1518);

3'-dihydro-3'-deoxy-4(R)-(5-phenylpyridin-2-yl)acetylamino spec-tinomycin (1519);

3'-dihydro-3'-deoxy-4(R)-(2-(phenylamino)thiazol-4-yl)acetylamino spectinomycin (1520);

3'-dihydro-3'-deoxy-4(R)-(thiazol-4-yl)acetylamino spectinomycin (1443);

3'-dihydro-3'-deoxy-4(R)-(5-fluoropyridin-2-yl)acetylamino spectinomycin (1445);

3'-dihydro-3'-deoxy-4(R)-(2,3-difluorophenyl)acetylamino spectinomycin (1447);

3'-Dihydro-3'-deoxy-4(R)-(5-(4-chlorophenyl)pyridin-2-yl) acetylamino spectinomycin (1535);

3'-Dihydro-3'-deoxy-4(R)-2-(1-benzyl-1H-1,2,3-triazol-4-yl)acetylamino spectinomycin (1537);

3'-Dihydro-3'-deoxy-4(R)-(2-((4-fluorophenyl)amino)thiazol-4-yl)acetylamino spectinomycin (1538);

3'-Dihydro-3'-deoxy-4(R)-(2-((3-fluorophenyl)amino)thiazol-4-yl)acetylamino spectinomycin (1539);

3'-Dihydro-3'-deoxy-4(R)-(2-((4-(trifluoromethoxy)phenyl)amino)thiazol-4-yl)acetylamino spectinomycin (1540);

3'-Dihydro-3'-deoxy-4(R)-(2-((4-(trifluoromethyl)phenyl)amino)thiazol-4-yl)acetylamino spectinomycin (1541);

3'-Dihydro-3'-deoxy-4(R)-(5-(4-fluorophenyl)pyridin-2-yl) acetylamino spectinomycin (1542);

3'-Dihydro-3'-deoxy-4(R)-(5-(3-methoxyphenyl)pyridin-2-yl)acetylamino spectinomycin (1543);

3'-Dihydro-3'-deoxy-4(R)-(4-chloropyridin-2-yl)acetylamino spec-tinomycin (1544);

3'-dihydro-3'-deoxy-4(R)-(4-methoxyphenyl)acetylamino spectinomycin (1446); and

3'-dihydro-3'-deoxy-4(R)-[2(S)-amino-3-phenyl]propanoylamino spectinomycin (1515).

In some embodiments, the infection is an *Enterococcus faecalis* infection and the compound of Formula (I) is selected from the group comprising:

3'-dihydro-3'-deoxy-4(R)-furan-2-yl-methylamino spectinomycin (1422);

3'-dihydro-3'-deoxy-4(R)-(5-fluoropyridin-2-yl)acetylamino spectinomycin (1445);

3'-dihydro-3'-deoxy-4(R)-(benzothiazol-2-yl)acetylamino spectinomycin (1491);

3'-dihydro-3'-deoxy-4(R)-(5-phenylpyridin-2-yl)acetylamino spec-tinomycin (1519);

3'-Dihydro-3'-deoxy-4(R)-(5-(4-chlorophenyl)pyridin-2-yl) acetylamino spectinomycin (1535);

3'-Dihydro-3'-deoxy-4(R)-2-(1-benzyl-1H-1,2,3-triazol-4-yl)acetylamino spectinomycin (1537);

3'-Dihydro-3'-deoxy-4(R)-(2-((4-fluorophenyl)amino)thiazol-4-yl)acetylamino spectinomycin (1538);

3'-Dihydro-3'-deoxy-4(R)-(2-((3-fluorophenyl)amino)thiazol-4-yl)acetylamino spectinomycin (1539);

3'-Dihydro-3'-deoxy-4(R)-(2-((4-(trifluoromethoxy)phenyl)amino)thiazol-4-yl)acetylamino spectinomycin (1540);

3'-Dihydro-3'-deoxy-4(R)-(2-((4-(trifluoromethyl)phenyl)amino)thiazol-4-yl)acetylamino spectinomycin (1541);

3'-Dihydro-3'-deoxy-4(R)-(5-(4-fluorophenyl)pyridin-2-yl) acetylamino spectinomycin (1542); and 3'-Dihydro-3'-deoxy-4(R)-(5-(3-methoxyphenyl)pyridin-2-yl)acetylamino spectinomycin (1543).

In some embodiments, the infection is a *Mycobacterium tuberculosis* infection and the compound of Formula (I) is selected from the group comprising:

3'-dihydro-3'-deoxy-4(R)-(pyridin-2-yl)acetylamino spectinomycin (1329);

3'-dihydro-3'-deoxy-4(R)-(4-fluorophenyl)acetylamino spectinomycin (1367);

3'-dihydro-3'-deoxy-4(R)-(pyridin-3-yl)acetylamino spectinomycin (1368);

3'-dihydro-3'-deoxy-4(R)-p-tolylacetylamino spectinomycin (1399);

3'-dihydro-3'-deoxy-4(R)-(3-methoxy-phenyl)acetylamino spectinomycin (1400);

3'-dihydro-3'-deoxy-4(R)-(thiazol-4-yl)acetylamino spectinomycin (1443);
3'-dihydro-3'-deoxy-4(R)-(2-aminothiazol-4-yl)acetylamino spectino-mycin (1444);
3'-dihydro-3'-deoxy-4(R)-(5-fluoropyridin-2-yl)acetylamino spectinomycin (1445);
3'-dihydro-3'-deoxy-4(R)-(1H-imidazol-4-yl)acetylamino spectinomycin (1466);
3'-dihydro-3'-deoxy-4(R)-(benzooxazol-2-yl)acetylamino spectinomycin (1465)
3'-dihydro-3'-deoxy-4(R)-(thiazol-2-yl)acetylamino spectinomycin (1489);
3'-dihydro-3'-deoxy-4(R)-(5-nitropyridin-2-yl)acetylamino spectinomycin (1490);
3'-dihydro-3'-deoxy-4(R)-(benzothiazol-2-yl)acetylamino spectinomycin (1491);
3'-dihydro-3'-deoxy-4(R)-(5-bromopyridin-2-yl)acetylamino spectinomycin (1516);
3'-dihydro-3'-deoxy-4(R)-(5-phenylpyridin-2-yl)acetylamino spectinomycin (1519);
3'-dihydro-3'-deoxy-4(R)-(2-phenylamino)thiazol-4-yl) acetylamino spectinomycin (1520);
3'-Dihydro-3'-deoxy-4(R)-(5-(4-chlorophenyl)pyridin-2-yl) acetylamino spectinomycin (1535);
3'-Dihydro-3'-deoxy-4(R)-(2-((4-fluorophenyl)amino)thiazol-4-yl)acetylamino spectinomycin (1538);
3'-Dihydro-3'-deoxy-4(R)-(2-((3-fluorophenyl)amino)thiazol-4-yl)acetylamino spectinomycin (1539);
3'-Dihydro-3'-deoxy-4(R)-(2-((4-(trifluoromethoxy)phenyl) amino)thiazol-4-yl)acetylamino spectinomycin (1540);
3'-Dihydro-3'-deoxy-4(R)-(2-((4-(trifluoromethyl)phenyl) amino)thiazol-4-yl)acetylamino spectinomycin (1541);
3'-Dihydro-3'-deoxy-4(R)-(5-(4-fluorophenyl)pyridin-2-yl) acetylamino spectinomycin (1542);
3'-Dihydro-3'-deoxy-4(R)-(5-(3-methoxyphenyl)pyridin-2-yl)acetylamino spectinomycin (1543); and
3'-Dihydro-3'-deoxy-4(R)-(4-chloropyridin-2-yl)acetylamino spectinomycin (1544);
or a pharmaceutically acceptable salt or prodrug thereof.

VII. Methods of Treating Tuberculosis

The present disclosure is believed to be the first to show that 3'-amino spectinomycin derivatives and 3'-acylamino spectinomycin derivatives are effective in treating infections related to tuberculosis. Accordingly, in some embodiments, the presently disclosed subject matter provides a method of treating tuberculosis in a subject in need of treatment thereof, the method comprising administering to the subject an effective amount of a compound of Formula (I):

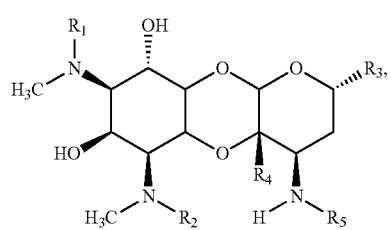

(I)

wherein:
$R_1$ and $R_2$ are each independently H, alkoxycarbonyl, or aralkoxycarbonyl;
$R_3$ is alkyl;
$R_4$ is H, hydroxy, alkyl, or alkoxy; and
$R_5$ is selected from the group comprising alkyl, substituted alkyl, aralkyl, substituted aralkyl, aryl, substituted aryl, and acyl;
or a pharmaceutically acceptable salt or a prodrug thereof.

Thus, the methods of the presently disclosed subject matter are useful for treating these tuberculosis in that they inhibit the onset, growth, or spread of a TB infection, cause regression of the TB infection, cure the TB infection, or otherwise improve the general well-being of a subject afflicted with, or at risk of, contracting tuberculosis.

In some embodiments, $R_1$ and $R_2$ are each H. In some embodiments, $R_3$ is a $C_1$-$C_8$ alkyl group (e.g., methyl, ethyl, or a branched, straight-chain or cyclic propyl, butyl, pentyl, hexyl, heptyl, or octyl). In some embodiments, $R_3$ is methyl or butyl (e.g., n-butyl). In some embodiments, $R_4$ is selected from H, OH, methyl and methoxy. In some embodiments, $R_4$ is hydroxy.

In some embodiments, $R_5$ is alkyl or aralkyl that includes a heteroaryl group or a cycloalkyl group (e.g., —$CH_2$-heteroaryl or —$CH_2$-cycloalkyl). In some embodiments, $R_5$ is substituted aralkyl that comprises a substituted phenyl group.

In some embodiments, $R_5$ is acyl and has the structure —C(=O)$R_6$, wherein $R_6$ is selected from the group comprising alkyl, substituted alkyl, aralkyl, substituted aralkyl, aryl, and substituted aryl.

In some embodiments, $R_6$ is selected from the group comprising: —$CH_2$NHC($CH_3$)$_3$, —$CH_2$CH($CH_3$)$_2$, —CH($NH_2$)CH($CH_3$)$CH_2$CH_3$, —CH($NH_2$)CH($CH_3$)$_2$, —CH($CH_2$$C_6$$H_5$)NHC(=O)$CH_2$$NH_2$, —$CH_2$$CH_2$NHC(=O)$C_6$$H_5$, and —$CH_2$$CH_2$NHC(=O)$CH_2$$C_6$$H_5$.

In some embodiments, $R_6$ is selected from the group comprising heteroaryl, substituted heteroaryl, 2-substituted phenyl, 4-halo-substituted phenyl, —$CH_2$$R_7$, and —C($R_8$)$_2$; wherein $R_7$ is selected from the group comprising aralkyl, substituted aralkyl, heteroaryl, substituted heteroaryl, and substituted phenyl, wherein said substituted phenyl can be characterized as one or more of fluoro-substituted phenyl, alkyl-substituted phenyl, 2-substituted phenyl, 3-mono-substituted phenyl, 2,3-di-substituted phenyl, and di-substituted phenyl wherein two phenyl carbons are together substituted with an alkylene; and each $R_8$ is independently aryl or substituted aryl.

In some embodiments, the compound of Formula (I) is a compound of Formula (Ia):

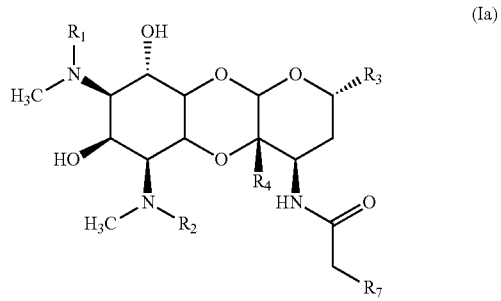

(Ia)

wherein:
$R_1$ and $R_2$ are each independently H, alkoxycarbonyl, or aralkoxycarbonyl;
$R_3$ is alkyl;
$R_4$ is H, hydroxy, alkyl, or alkoxy; and
$R_7$ is selected from the group comprising aralkyl, substituted aralkyl, heteroaryl, substituted heteroaryl, and substituted phenyl, wherein said substituted phenyl is selected from the group comprising fluoro-substituted phenyl, alkyl-substituted phenyl, 2-substituted phenyl, 3-mono-substituted phenyl, 2,3-di-substituted phenyl, and di-substituted phenyl wherein two phenyl carbons are together substituted with an alkylene; and or a pharmaceutically acceptable salt or a prodrug thereof.

In some embodiments, $R_7$ is substituted phenyl selected from the group comprising 4-fluorophenyl, 4-methylphenyl, 3-methylphenyl, 3-methoxyphenyl, 2-methoxyphenyl, 3,4-methylenedioxyphenyl, and 2,3-difluorophenyl.

In some embodiments, $R_7$ is heteroaryl or substituted heteroaryl comprising a heteroaryl group selected from the group comprising pyridyl, triazolyl, triazinyl, pyrimidinyl, pyridazinyl, oxazolyl, furanyl, benzofuranyl, thiophenyl, pyrrolyl, imidazoyl, thiazoyl, quinolinyl, isoquinolinyl, benzooxazolyl, and benzothiazolyl. In some embodiments, $R_7$ comprises heteroaryl selected from pyridyl, thiazoyl, benzooxazolyl, and benzothiazolyl.

In some embodiments, $R_7$ is substituted heteroaryl, wherein the heteroaryl is substituted with one or more of the group consisting of amino, alkylamino, arylamino, nitro, halo, hydroxy, carboxyl, acyl, alkyl, substituted alkyl (e.g., perhaloalkyl), alkoxy, perhaloalkoxy, aralkyl, aryl, aryloxy, and substituted aryl. For example, the $R_7$ heteroaryl group can be substituted with one or more fluoro, chloro, bromo, methoxy, methyl, $NO_2$, trifluoromethoxy, phenylamino, phenyl, or trifluoromethyl groups. In some embodiments, the $R_7$ heteroaryl group is substituted with an aryl or aryl-containing group such that the $R_7$ group as a whole is biaryl (i.e., the $R_7$ heteroaryl group is directly attached to another aryl or substituted aryl group or attached to the other aryl or substituted aryl group via a linker such as alkylene (e.g., methylene), —O—, —C(=O)—, or —NH—). The aryl-containing group attached to the $R_7$ heteroaryl group can be, for example, phenyl, benzyl, phenoxy, benzoyl, halo-substituted phenyl (e.g., p-fluorophenyl), alkoxy-substituted phenyl (e.g., m-methoxyphenyl) and the like or a phenylamino or substituted phenylamino group (e.g, halo-, alkyl-, alkoxy-, perhaloalkyl-, or perhaloalkoxy-substituted phenylamino).

In some embodiments, $R_7$ is an aralkyl or substituted aralkyl group that comprises a heteroaryl or substituted heteroaryl group. In some embodiments, the aralkyl or substituted aralkyl group can comprise a heteroaryl selected from the group comprising pyridyl, triazolyl, triazinyl, pyrimidinyl, pyridazinyl, oxazolyl, furanyl, benzofuranyl, thiophenyl, pyrrolyl, imidazoyl, thiazoyl, quinolinyl, isoquinolinyl, benzooxazolyl, and benzothiazolyl. In some embodiments, $R_7$ is aralkyl or substituted aralkyl comprising pyridyl, thiazoyl, benzooxazolyl, or benzothiazolyl. The heteroaryl moiety of the aralkyl group can be substituted with one or more of the group comprising amino, alkylamino, arylamino, nitro, halo, hydroxy carboxyl, acyl, alkyl, substituted alkyl (e.g., perhaloalkyl), alkoxy, perhaloalkoxy, aralkyl, aryl, aryloxy, and substituted aryl. For example, the heteroaryl group can be substituted with one or more fluoro, chloro, bromo, methoxy, Methyl, $NO_2$, trifluoromethoxy, phenylamino, phenyl or trifluoromethyl groups. In addition, the alkyl moiety of the aralkyl $R_7$ group can also be substituted, e.g., with an alkyl, acyl, amino, acylamino, halo, hydroxy or other alkyl group substituent.

In some embodiments, $R_7$ is a nitrogen-containing heteroaryl group, optionally substituted by one or more aryl group substituents. In some embodiments, at least one nitrogen atom in the nitrogen-containing heteroaryl group is positioned adjacent (i.e., in the 2-position) to the atom attached directly to the acyl methylene group of the structure of Formula (Ia). In some embodiments, the compound of Formula (Ia) is a compound of Formula (Ib), (Ic), or (Id):

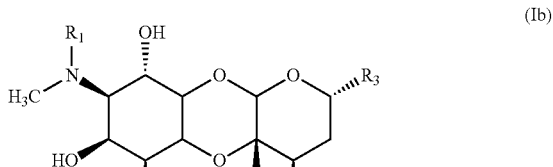

(Ib)

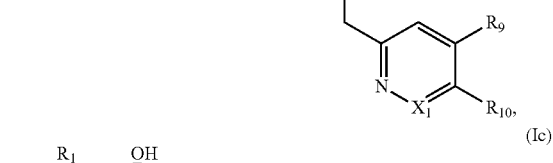

(Ic)

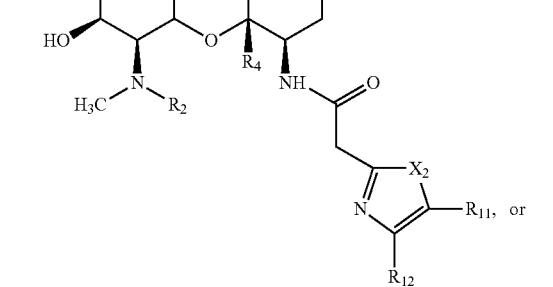

(Id)

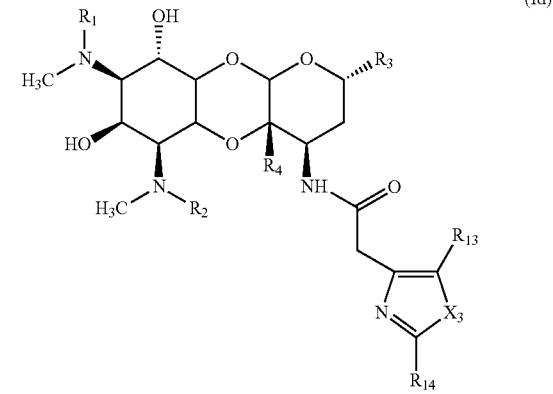

wherein:

$R_1$ and $R_2$ are each independently H, alkoxycarbonyl, or aralkoxycarbonyl;

$R_3$ is alkyl;

$R_4$ is H, hydroxy, alkyl, or alkoxy;

$X_1$ is CH or N;

$X_2$ and $X_3$ are O, S, or NH;

$R_9$, $R_{10}$, $R_{11}$, $R_{12}$, $R_{13}$, and $R_{14}$ are independently selected from the group comprising H, halo, hydroxy, nitro, $N(R_{15})_2$, alkyl, substituted alkyl, alkoxy, perhaloalkoxy, aralkyl, substituted aralkyl, aralkoxy, aryl (e.g., phenyl or heteroaryl), aryloxy, acyl (e.g., aroyl), and substituted aryl (e.g., substituted phenyl or substituted heteroaryl); or wherein $R_9$ and $R_{10}$ together or $R_{11}$ and $R_{12}$ together are alkylene (e.g., —CH=CH—CH=CH—); and wherein each $R_{15}$ is independently selected from the group comprising H, alkyl, substituted alkyl, aralkyl, substituted aralkyl, aryl (e.g., phenyl or heteroaryl), and substituted aryl (e.g., substituted phenyl or substituted heteroaryl);

or a pharmaceutically acceptable salt or a prodrug thereof.

In some embodiments, at least one of $R_9$, $R_{10}$, $R_{11}$, $R_{12}$, $R_{13}$, and $R_{14}$ is $N(R_{15})_2$, for example, wherein one $R_{15}$ is aryl or substituted aryl. In some embodiments, at least one of $R_9$, $R_{10}$, $R_{11}$, $R_{12}$, $R_{13}$, and $R_{14}$ is aryl or substituted aryl.

In some embodiments, the compound is a compound of Formula (Ib), wherein $X_1$ is CH and wherein $R_{10}$ is other than H (e.g., wherein $R_{10}$ is selected from aryl, substituted aryl, halo or nitro). In some embodiments, the compound is a compound of Formula (Id), wherein $X_3$ is S and $R_{13}$ is H. In some embodiments, $R_{14}$ is $N(R_{15})_2$.

In some embodiments, the compound is selected from the group comprising:

3'-dihydro-3'-deoxy-4(R)-(3-pyridin-3-yl)propionylamino spectinomycin (1299);

3'-dihydro-3'-deoxy-4(R)-(pyridin-2-yl)acetylamino spectinomycin (1329);

3'-dihydro-3'-deoxy-4(R)-4-fluorobenzoylamino spectinomycin (1364);

3'-dihydro-3'-deoxy-4(R)-furan-2-carboxylicamino spectinomycin (1365);

3'-dihydro-3'-deoxy-4(R)-(4-fluorophenyl)acetylamino spectinomycin (1367);

3'-dihydro-3'-deoxy-4(R)-(pyridin-3-yl)acetylamino spectinomycin (1368);

3'-dihydro-3'-deoxy-4(R)-pyridin-2-carboxylicamino spectinomycin (1370);

3'-dihydro-3'-deoxy-4(R)-p-tolylacetylamino spectinomycin (1399);

3'-dihydro-3'-deoxy-4(R)-(3-methoxy-phenyl)acetylamino spectinomycin (1400);

3'-dihydro-3'-deoxy-4(R)-[3,4-(methylene dioxy)phenyl]acetylamino spectinomycin (1411);

3'-dihydro-3'-deoxy-4(R)-m-tolylacetylamino spectinomycin (1412);

3'-dihydro-3'-deoxy-4(R)-(pyridin-4-yl)acetylamino spectinomycin (1413);

3'-dihydro-3'-deoxy-4(R)-(thiazol-4-yl)acetylamino spectinomycin (1443);

3'-dihydro-3'-deoxy-4(R)-(2-aminothiazol-4-yl)acetylamino spectino-mycin (1444);

3'-dihydro-3'-deoxy-4(R)-(5-fluoropyridin-2-yl)acetylamino spectinomycin (1445);

3'-dihydro-3'-deoxy-4(R)-(2,3-difluorophenyl)acetylamino spectinomycin (1447);

3'-dihydro-3'-deoxy-4(R)-(2-methoxyphenyl)acetylamino spectinomycin (1448);

3'-dihydro-3'-deoxy-4(R)-(pyridazin-3-yl)acetylamino spectinomycin (1449);

3'-dihydro-3'-deoxy-4(R)-(benzooxazol-2-yl)acetylamino spectinomycin (1465);

3'-dihydro-3'-deoxy-4(R)-(1H-imidazol-4-yl)acetylamino spectinomycin (1466);

3'-dihydro-3'-deoxy-4(R)-[3(R)-amino-3-(4-fluorophenyl)]propanoylamino spectinomycin (1487);

3'-dihydro-3'-deoxy-4(R)-(thiazol-2-yl)acetylamino spectinomycin (1489);

3'-dihydro-3'-deoxy-4(R)-(5-nitropyridin-2-yl)acetylamino spectinomycin (1490);

3'-dihydro-3'-deoxy-4(R)-(benzothiazol-2-yl)acetylamino spectinomycin (1491);

3'-dihydro-3'-deoxy-4(R)-[2(S)-amino-3-phenyl]propanoylamino spectinomycin (1515);

3'-dihydro-3'-deoxy-4(R)-(5-bromopyridin-2-yl)acetylamino spectinomycin (1516);

3'-dihydro-3'-deoxy-4(R)-(2-phenylthiazol-4-yl)acetylamino spectinomycin (1517);

3'-dihydro-3'-deoxy-4(R)-(pyridin-2-yl)propanoylamino spectinomycin (1518);

3'-dihydro-3'-deoxy-4(R)-(5-phenylpyridin-2-yl)acetylamino spectinomycin (1519);

3'-dihydro-3'-deoxy-4(R)-(2-(phenylamino)thiazol-4-yl)acetylamino spectinomycin (1520);

3'-Dihydro-3'-deoxy-4(R)-(5-(4-chlorophenyl)pyridin-2-yl)acetylamino spectinomycin (1535);

3'-Dihydro-3'-deoxy-4(R)-(quinoline-8-yl)carbonylamino Spectinomycin (1536);

3'-Dihydro-3'-deoxy-4(R)-2-(1-benzyl-1H-1,2,3-triazol-4-yl)acetylamino spectinomycin (1537);

3'-Dihydro-3'-deoxy-4(R)-(2-((4-fluorophenyl)amino)thiazol-4-yl)acetylamino spectinomycin (1538);

3'-Dihydro-3'-deoxy-4(R)-(2-((3-fluorophenyl)amino)thiazol-4-yl)acetylamino spectinomycin (1539);

3'-Dihydro-3'-deoxy-4(R)-(2-((4-(trifluoromethoxy)phenyl)amino)thiazol-4-yl)acetylamino spectinomycin (1540);

3'-Dihydro-3'-deoxy-4(R)-(2-((4-(trifluoromethyl)phenyl)amino)thiazol-4-yl)acetylamino spectinomycin (1541);

3'-Dihydro-3'-deoxy-4(R)-(5-(4-fluorophenyl)pyridin-2-yl)acetylamino spectinomycin (1542);

3'-Dihydro-3'-deoxy-4(R)-(5-(3-methoxyphenyl)pyridin-2-yl)acetylamino spectinomycin (1543);

3'-Dihydro-3'-deoxy-4(R)-(4-chloropyridin-2-yl)acetylamino spectinomycin (1544);

3'-dihydro-3'-deoxy-4(R)-(tert-butylamino)acetylamino spectinomycin (1351);

3'-dihydro-3'-deoxy-4(R)-(3-methyl)butanoylamino spectinomycin (1369);

3'-dihydro-3'-deoxy-4(R)-[(2S,3S)-2-amino-3-methyl]pentanoylamino spectinomycin (1485);

3'-dihydro-3'-deoxy-4(R)-[2(S)-amino-3-methyl]butanoylamino spectinomycin (1486);

3'-dihydro-3'-deoxy-4(R)-dodecanoylamino spectinomycin (1366);

3'-dihydro-3'-deoxy-4(R)-(3-amino)-propanoylamino spectinomycin (1469);

3'-dihydro-3'-deoxy-4(R)-phenylacetylamino spectinomycin (1398);

3'-dihydro-3'-deoxy-4(R)-cyclopropylmethylamino spectinomycin (1419);

3'-dihydro-3'-deoxy-4(R)-(3-methyl)butylamino spectinomycin (1420);

3'-dihydro-3'-deoxy-4(R)-dodecylamino spectinomycin (1421);

3'-dihydro-3'-deoxy-4(R)-furan-2-yl-methylamino spectinomycin (1422);

3'-dihydro-3'-deoxy-4(R)-(3-methoxy)benzylamino spectinomycin (1423);

3'-dihydro-3'-deoxy-4(R)-(4-fluoro)benzylamino spectinomycin (1424);

3'-dihydro-3'-deoxy-4(R)-(4-methyl)benzylamino spectinomycin (1425);

3'-dihydro-3'-deoxy-4(R)-2-phenylethylamino spectinomycin (1450);

3'-dihydro-3'-deoxy-4(R)-(4-methoxyphenyl)acetylamino spectinomycin (1446);

3'-dihydro-3'-deoxy-4(R)-[2(S)-aminopropanoylamino spectinomycin (1467); and

3'-dihydro-3'-deoxy-4(R)-(2-amino)acetylamino spectinomycin (1470);

or a pharmaceutically acceptable salt or prodrug thereof.

The compound can be administered via any suitable route: orally, topically, intravenously, etc. In some embodiments, the compound is administered orally or via inhalation.

In some embodiments, an additional therapeutic compound is administered to the subject (e.g., simultaneously with the compound of Formula (I) or prior to or after the compound of Formula (I)). In some embodiments, the additional therapeutic compound is an antibiotic or a therapeutic compound that can reduce pain and/or fever (e.g., an anti-inflammatory). Antibiotics include, but are not limited to, penicillins, e.g., penicillin G, penicillin V, methicillin, oxacillin, carbenicillin, nafcillin, ampicillin, etc.; penicillins in combination with beta-lactamase inhibitors, cephalosporins, e.g., cefaclor, cefazolin, cefuroxime, moxalactam, etc.; carbapenems; monobactams; aminoglycosides; tetracyclines; macrolides; lincomycins; polymyxins; sulfonamides; quinolones; cloramphenical; metronidazole; trimethoprim; vancomycin; streptomycin; etc. In some embodiments, the additional therapeutic is an anti-tuberculosis compound, such as, but not limited to isoniazid, ethambutol, rifampicin, kanamycin, capreomycin, linezolid, and streptomycin.

In some embodiments, the compound of Formula (I) is administered prophylactically to prevent or reduce the incidence of one of: (a) a *Mycobacterium tuberculosis* infection in a subject at risk of infection; (b) a recurrence of a *Mycobacterium tuberculosis* infection; and (c) combinations thereof. In some embodiments, the compound of Formula (I) is administered to treat an existing *Mycobacterium tuberculosis* infection, in some embodiments, the compound is administered to treat, prevent, or reduce the incidence of an infection related to another mycobacterium of the tuberculosis complex (e.g., *M. africanum, M. canetti, M. microti*) or *M. bovis*.

Subjects suffering from a *M. tuberculosis* or other tuberculosis-related infection can be determined via a number of techniques, e.g., sputum smear, chest X-ray, tuberculin skin test (i.e., Mantoux test) and/or the presence of other clinical symptoms (e.g., chest pain, coughing blood, fever, night sweats, appetite loss, fatigue, etc.). If desired, bacterial RNA, DNA or proteins can be isolated from a subject believed to be suffering from TB and analyzed via methods known in the art and compared to known nucleic or amino acid sequences of bacterial RNA, DNA or protein.

In some embodiments, the compound of Formula (I) is administered to treat an infection of a multi-drug resistant strain of *Mycobacterium tuberculosis* (i.e., a strain that is resistant to two or more previously known anti-tuberculosis drugs, such as isoniazid, ethambutol, rifampicin, kanamycin, capreomycin, linezolid, and streptomycin.

In some embodiments, the compound of Formula (I), (Ia), (Ib), (Ic) and/or (Id) has a minimum inhibitory concentration (MIC) against *Mycobacterium tuberculosis* of 25 µg/mL or less. MICs can be determined via methods known in the art, for example, as described in Hurdle et al., *J. Antimicrob. Chemother.*, 62(5), 1037-1045 (2008).

VIII. Pharmaceutical Formulations

The compounds of Formulas (I), (Ia), (Ib), (Ic), and (Id), the pharmaceutically acceptable salts thereof, prodrugs corresponding to compounds of Formulas (I), (Ia), (Ib), (Ic), and (Id), and the pharmaceutically acceptable salts thereof, are all referred to herein as "active compounds." Pharmaceutical formulations comprising the aforementioned active compounds also are provided herein. These pharmaceutical formulations comprise active compounds as described herein, in a pharmaceutically acceptable carrier. Pharmaceutical formulations can be prepared for oral, intravenous, intramuscular, topical or aerosol administration as discussed in greater detail below. The formulations can be prepared in dosages forms, such as but not limited to, tablets, capsules, liquids (solutions or suspensions), suppositories, ointments, creams, or aerosols. Also, the presently disclosed subject matter provides such active compounds that have been lyophilized and that can be reconstituted to form pharmaceutically acceptable formulations for administration, for example, as by intravenous or intramuscular injection.

The therapeutically effective amount or dosage of any specific active compound, the use of which is within the scope of embodiments described herein, will vary somewhat from compound to compound, and patient to patient, and will depend upon the condition of the patient and the route of delivery. As a general proposition, a dosage from about 0.1 to about 50 mg/kg will have therapeutic efficacy, with all weights being calculated based upon the weight of the active compound, including the cases where a salt is employed. Toxicity concerns at the higher level can restrict intravenous dosages to a lower level, such as up to about 10 mg/kg, with all weights being calculated based on the weight of the active base, including the cases where a salt is employed. A dosage from about 10 mg/kg to about 50 mg/kg can be employed for oral administration. Typically, a dosage from about 0.5 mg/kg to 5 mg/kg can be employed for intramuscular injection. Representative dosages are 1 µmol/kg to 50 µmol/kg, and optionally 22 µmol/kg and 33 µmol/kg of the compound for intravenous or oral administration.

The duration of the treatment is usually once or twice per day for a period of two to three weeks or until the condition is essentially controlled. Lower doses given less frequently can be used prophylactically to prevent or reduce the incidence of recurrence of the infection.

For topical administration, formulations (e.g., solutions, pastes, creams, salves, ointments, etc.) can be prepared comprising between about 0.05 and about 5% active compound by weight, which can be applied one or more times daily for a period of time (e.g., one, two or three weeks) or until the condition is essentially controlled.

In accordance with the present methods, pharmaceutically active compounds as described herein can be administered orally as a solid or as a liquid, or can be administered intramuscularly or intravenously as a solution, suspension, or emulsion. Alternatively, the compounds or salts also can be administered by inhalation, intravenously, or intramuscularly as a liposomal suspension. When administered through inhalation the active compound or salt should be in the form of a plurality of solid particles or droplets having a particle size from about 0.5 to about 5 microns, and preferably from about 1 to about 2 microns.

Pharmaceutical formulations suitable for intravenous or intramuscular injection are further embodiments provided herein. The pharmaceutical formulations comprise a compound of Formula (I), (Ia), (Ib), (Ic), and/or (Id) described herein, a prodrug as described herein, or a pharmaceutically acceptable salt thereof, in any pharmaceutically acceptable carrier. If a solution is desired, water is the carrier of choice with respect to water-soluble compounds or salts. With respect to the water-soluble compounds or salts, an organic vehicle, such as glycerol, propylene glycol, polyethylene glycol, or mixtures thereof, can be suitable. In the latter instance, the organic vehicle can contain a substantial amount of water. The solution in either instance can then be sterilized in a suitable manner known to those in the art, and typically by filtration through a 0.22-micron filter. Subsequent to sterilization, the solution can be dispensed into appropriate receptacles, such as depyrogenated glass vials. The dispensing is preferably done by an aseptic method. Sterilized closures can then be placed on the vials and, if desired, the vial contents can be lyophilized.

In addition to compounds of Formula (I), (Ia), (Ib), (Ic), and/or (Id) or their salts or prodrugs, the pharmaceutical formulations can contain other additives, such as pH-adjusting additives. In particular, useful pH-adjusting agents include acids, such as hydrochloric acid, bases or buffers, such as sodium lactate, sodium acetate, sodium phosphate, sodium citrate, sodium borate, or sodium gluconate. Further, the formulations can contain antimicrobial preservatives. Useful antimicrobial preservative include methylparaben, propylparaben, and benzyl alcohol. The antimicrobial preservative is typically employed when the formulation is placed in a vial designed for multi-dose use. The pharmaceutical formulations described herein can be lyophilized using techniques well known in the art.

In yet another embodiment of the subject matter described herein, there is provided an injectable, stable, sterile formulation comprising a compound of Formula (I), (Ia), (Ib), (Ic), and/or (Id), or a salt thereof, in a unit dosage form in a sealed container. The compound or salt is provided in the form of a lyophilizate, which is capable of being reconstituted with a suitable pharmaceutically acceptable carrier to form a liquid formulation suitable for injection thereof into a subject. The unit dosage form typically comprises from about 10 mg to about 10 grams of the compound salt. When the compound or salt is substantially water-insoluble, a sufficient amount of emulsifying agent, which is physiologically acceptable, can be employed in sufficient quantity to emulsify the compound or salt in an aqueous carrier. One such useful emulsifying agent is phosphatidyl choline.

Other pharmaceutical formulations can be prepared from the water-insoluble compounds disclosed herein, or salts thereof, such as aqueous base emulsions. In such an instance, the formulation will contain a sufficient amount of pharmaceutically acceptable emulsifying agent to emulsify the desired amount of the compound or salt thereof. Particularly useful emulsifying agents include phosphatidyl cholines and lecithin.

Additional embodiments provided herein include liposomal formulations of the active compounds disclosed herein. The technology for forming liposomal suspensions is well known in the art. When the compound is an aqueous-soluble salt, using conventional liposome technology, the same can be incorporated into lipid vesicles. In such an instance, due to the water solubility of the active compound, the active compound will be substantially entrained within the hydrophilic center or core of the liposomes. The lipid layer employed can be of any conventional composition and can either contain cholesterol or can be cholesterol-free. When the active compound of interest is water-insoluble, again employing conventional liposome formation technology, the salt can be substantially entrained within the hydrophobic lipid bilayer that forms the structure of the liposome. In either instance, the liposomes that are produced can be reduced in size, as through the use of standard sonication and homogenization techniques.

The liposomal formulations comprising the active compounds disclosed herein can be lyophilized to produce a lyophilizate, which can be reconstituted with a pharmaceutically acceptable carrier, such as water, to regenerate a liposomal suspension.

Pharmaceutical formulations also are provided which are suitable for administration as an aerosol topically or by inhalation. These formulations can comprise a solution or suspension of a desired compound described herein or a salt thereof, or a plurality of solid particles of the compound or salt. The desired formulation can be placed in a small chamber and nebulized. Nebulization can be accomplished by compressed air or by ultrasonic energy to form a plurality of liquid droplets or solid particles comprising the compounds or salts. The liquid droplets or solid particles should have a particle size in the range of about 0.5 to about 10 microns, more preferably from about 0.5 to about 5 microns. The solid particles can be obtained by processing the solid compound or a salt thereof, in any appropriate manner known in the art, such as by micronization. Most preferably, the size of the solid particles or droplets will be from about 1 to about 2 microns. In this respect, commercial nebulizers are available to achieve this purpose. The compounds can be administered via an aerosol suspension of respirable particles in a manner set forth in U.S. Pat. No. 5,628,984, the disclosure of which is incorporated herein by reference in its entirety.

When the pharmaceutical formulation suitable for administration as an aerosol is in the form of a liquid, the formulation can comprise a water-soluble active compound in a carrier that comprises water. A surfactant can be present, which lowers the surface tension of the formulation sufficiently to result in the formation of droplets within the desired size range when subjected to nebulization.

As indicated, both water-soluble and water-insoluble active compounds are provided. As used herein, the term "water-soluble" is meant to define any composition that is soluble in water in an amount of about 50 mg/mL, or greater. Also, as used herein, the term "water-insoluble" is meant to define any composition that has a solubility in water of less than about 20 mg/mL. In some embodiments, water-soluble compounds or salts can be desirable whereas in other embodiments water-insoluble compounds or salts likewise can be desirable.

The subject treated in the presently disclosed subject matter in its many embodiments is desirably a human subject, although it is to be understood the methods described herein are effective with respect to all vertebrate species, which are intended to be included in the term "subject." The methods described herein are particularly useful in the treatment and/or prevention of infectious diseases in warm-blooded vertebrates. Thus, the methods can be used as treatment for mammals and birds.

More particularly, provided herein is the treatment of mammals, such as humans, as well as those mammals of importance due to being endangered (such as Siberian tigers), of economical importance (animals raised on farms for consumption by humans) and/or social importance (animals kept as pets or in zoos) to humans, for instance, carnivores other than humans (such as cats and dogs), swine (pigs, hogs, and wild boars), ruminants (such as cattle, oxen, sheep, llamas, giraffes, deer, goats, bison, and camels), and horses. Also provided herein is the treatment of birds, including the treatment of those kinds of birds that are endangered, kept in zoos or as pets (e.g., parrots), as well as fowl, and more particularly domesticated fowl, i.e., poultry, such as turkeys, chickens, ducks, geese, guinea fowl, and the like, as they also are of economical importance to humans. Thus, embodiments of the methods described herein include the treatment of livestock, including, but not limited to, domesticated swine (pigs and hogs), ruminants, horses, poultry, and the like.

EXAMPLES

The following Examples have been included to illustrate modes of the presently disclosed subject matter. In light of the present disclosure and the general level of skill in the art, those of skill will appreciate that the following Examples are intended to be exemplary only and that numerous changes, modifications, and alterations can be employed without departing from the scope of the presently disclosed subject matter.

Example 1

Synthesis of Spectinomycin Analogs

General Methods The presently disclosed 3'-deoxy 3'-acylamino and 3'-deoxy 3'(R)-alkylamino spectinomycins were synthesized according to procedures analogous to those previously described. See Woitun et al., *J. Antibiot (Tokyo)*, 34(1), 22-27 (1981); and Maier et al., *J. Antibiot (Tokyo)*, 34(1), 16-21 (1981). 1,3-Dibenzyloxycarbonyl-3'(R)-amino spectinomycin was synthesized from spectinomycin dihydrochloride pentahydrate in two steps as shown in FIG. 1. First, the secondary methyl amines on the A ring were protected as benzyl carbamates with carboxybenzyl (CBz) groups using benzyl chloroformate and $NaHCO_3$ in water. Then the 3'-deoxy-3'-amino derivative was obtained by the reductive amination of the protected intermediate with ammonium nitrate and sodium cyanoborohydride in methanol.

The amine was then used for the synthesis of the targeted 3'-acylamino spectinomycin derivatives by coupling it to a variety of acids using HBTU in dichloromethane. See FIG. 1. The CBz groups were removed by catalytic hydrogenation using palladium on carbon (Pd/C) for 2 hrs to afford the target amides. For aryl side chains sensitive to the hydrogenolysis conditions used to remove the CBz groups, exposure to aqueous HBr 48% for 2 hrs was used as an alternative method to afford the deprotected final product.

Figure 2:
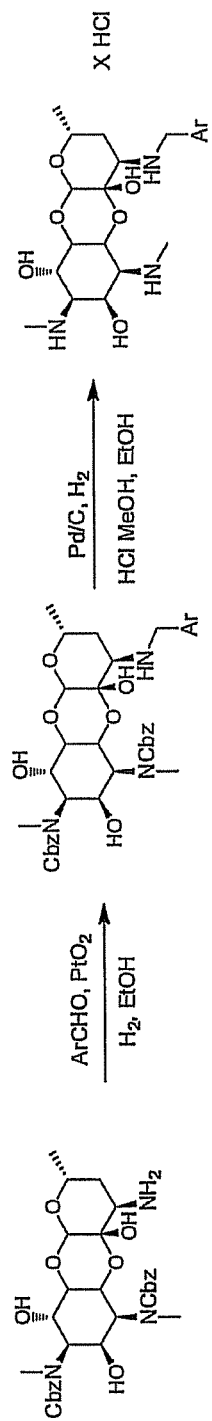
FIG. 2 is a schematic drawing of exemplary methods for synthesizing compounds of the presently disclosed subject matter.
Figure 3:
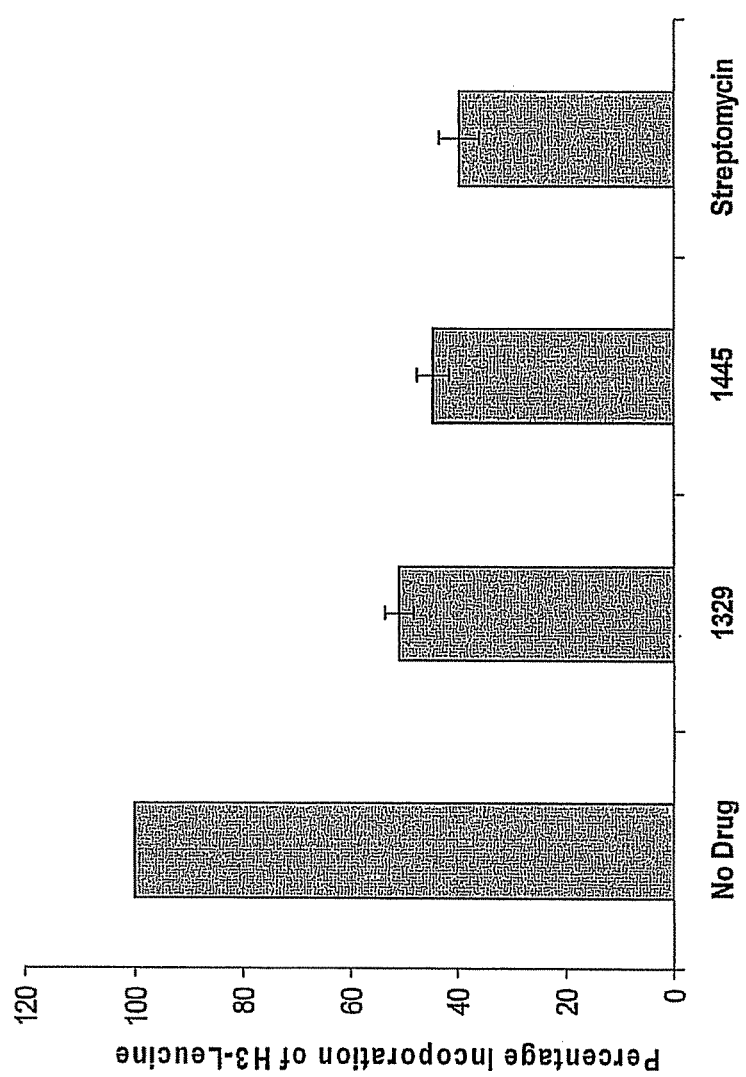
FIG. 3 is a bar graph showing the inhibition of protein synthesis in whole cell *M. bovis* BCG caused by compound 1329, 1445 or the control antibiotic streptomycin after incubation with compound for 4 hours.
Figure 4:
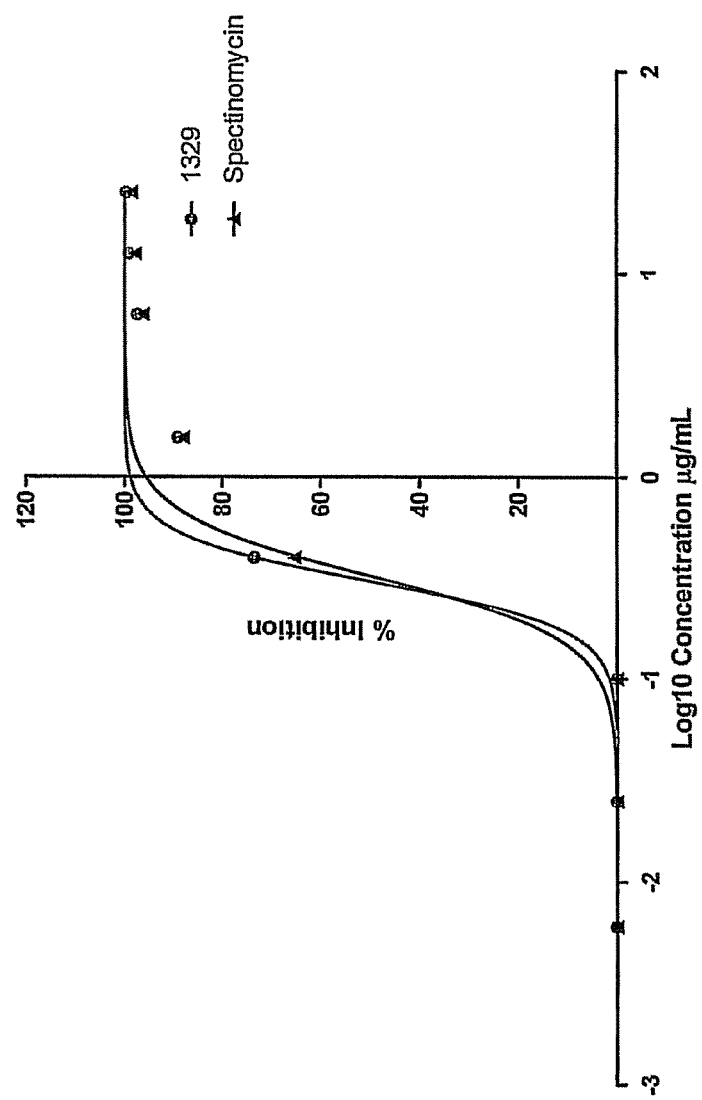
FIG. 4 is a graph comparing the inhibition of luciferase protein synthesis caused by compound 1329 (circles) or spectinomycin (triangles) in the *E. coli* S30 transcription/translation assay.
Figure 5:
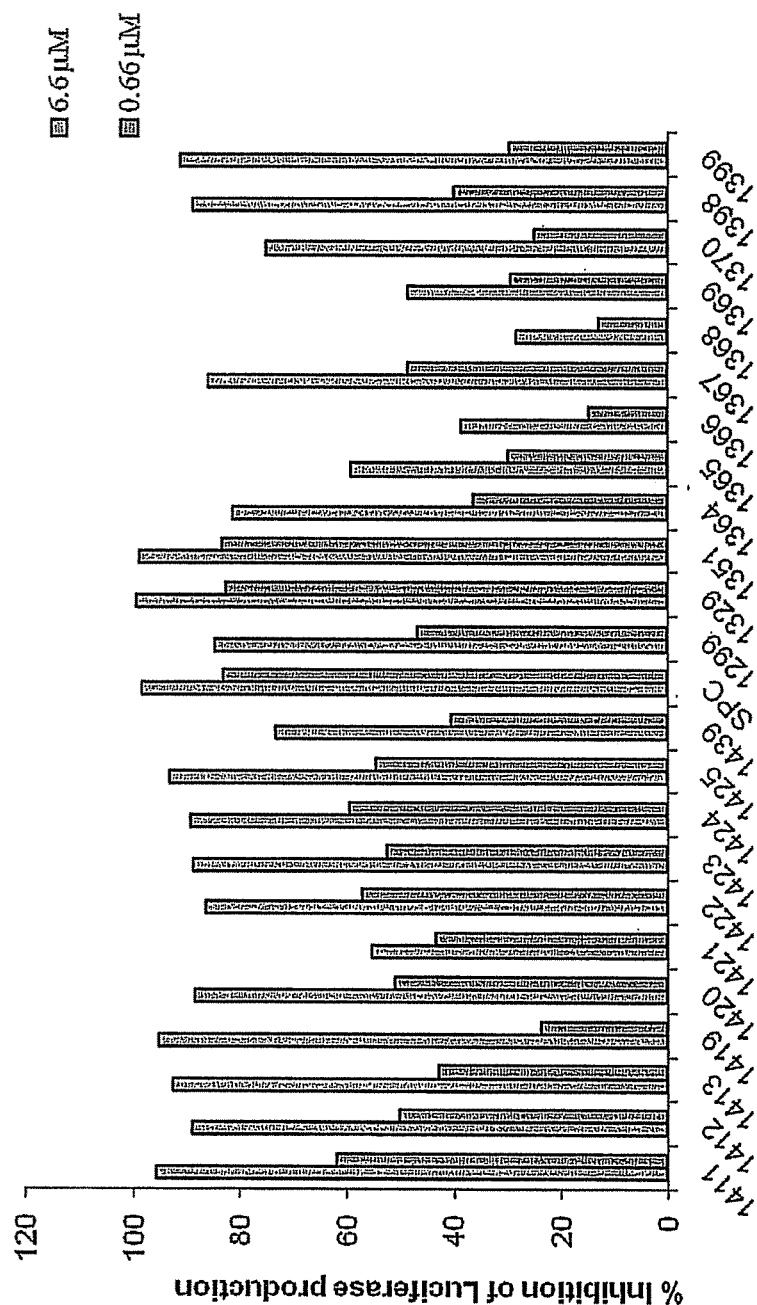
Figure 6:
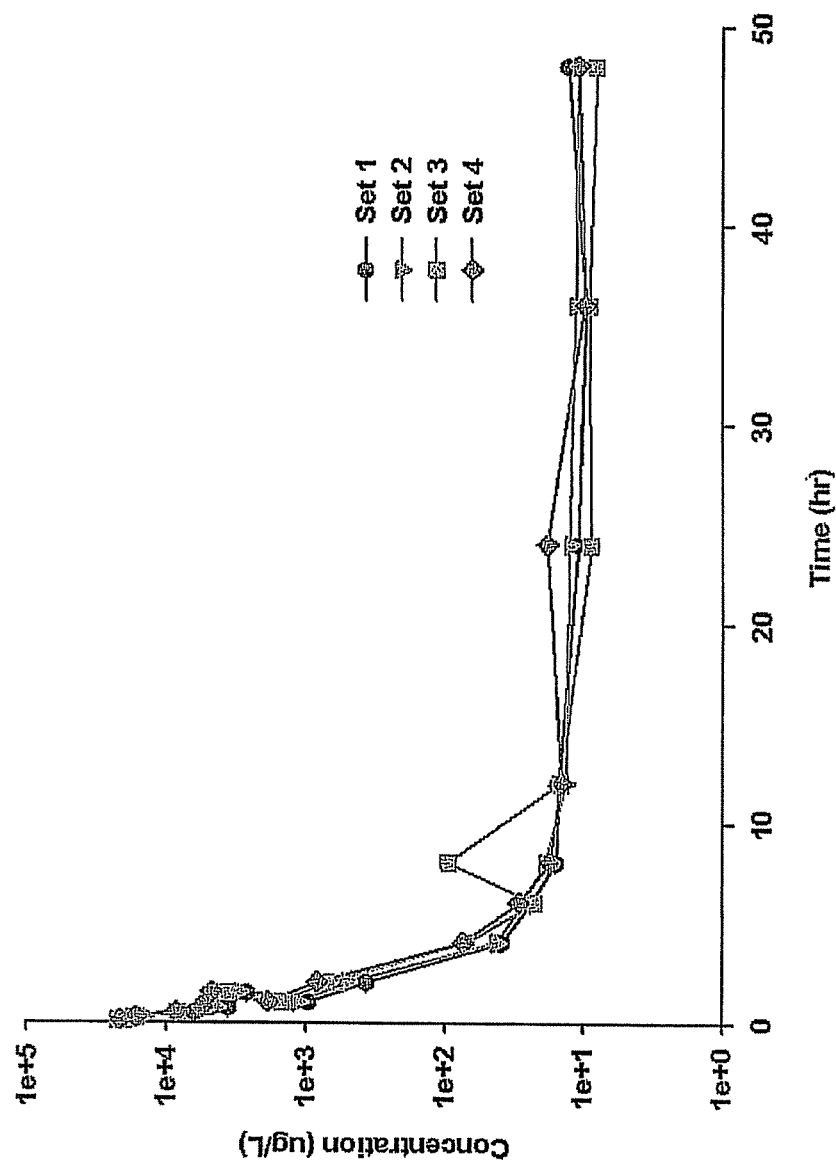

The 3'-deoxy-3'-alkylamino spectinomycin derivatives were obtained by two routes: either by reduction of corresponding di-CBz-protected amides using $NaBH_4$ in the presence of TFA and dioxane for simple alkyl substituents (see FIG. 1); or by direct reductive alkylation of 1,3-dibenzyloxycarbonyl 3'(R)-amino spectinomycin with aryl aldehydes with $PtO_2$ catalyzed hydrogenation to afford arylalkyl substituted amines. See FIG. 2. Both approaches were then followed by CBz deprotection using catalytic hydrogenation using Pd/C for 2 hrs to afford the target 3'-deoxy 3'(R)-alkylamino spectinomycins.

General Procedure for the Synthesis of 3'-deoxy 3'-acylamino spectinomycins:

To a stirred solution of selected acid (3 mmol) in $CH_2Cl_2$ (10 mL) and DIPEA (6 mmol) was added HBTU (3 mmol) and the mixture was stirred at room temperature for 1 h. Then 6,8-dibenzyloxycarbonyl 4(R)-amino spectinomycin (1 mmol) was added and stirred at room temperature for overnight. The reaction solution was diluted with excess $CH_2Cl_2$ and washed with water, dried ($Na_2SO_4$) and concentrated. The residue was purified by column chromatography to afford corresponding protected amide using petroleum/ethylacetate gradient eluent system. Deprotection of the amino protecting groups was achieved by dissolution of the protected amide in 1.25 M HCl in MeOH and EtOH (1:1) with 10% Pd—C (50% by mass). The mixture was hydrogenated under 30 Psi/$H_2$ at room temperature for 2 hrs, filtered and concentrated. The resulting solid was titurated with cold diethyl ether, filtered and the resulting solid washed with excess ether and dried in vacuo to give the target 3'-deoxy 3'-acylamino spectinomycins.

General Procedure for the Synthesis of 3'-deoxy 3'-acylamino spectinomycins, Method 2:

To a stirred solution of selected acid (3 mmol) in $CH_2Cl_2$ (10 mL) and DIPEA (6 mmol) was added HBTU (3 mmol) and the mixture was stirred at room temperature for 1 h. Then 6,8-dibenzyloxycarbonyl 4 (R)-amino spectinomycin (1 mmol) was added and stirred at room temperature for overnight. The reaction solution was diluted with excess $CH_2Cl_2$ and washed with water, dried ($Na_2SO_4$) and concentrated. The residue was purified by column chromatograph to afford corresponding protected amide using a petroleum/ethylacetate gradient eluent syntem. Deprotection of the amion protecting groups was achieved by dissolving the protected amide in 48% HBr (in water). The mixture was stirred at room temperature for 2 hs, and then the solution was dried in vacuo. The residue was dissolved by methanol, to this solution ether was added, then filtered the solid and washed with ether to give the target 3'-deoxy 3'-acylamino spectinomycins.

Analytical Data for Individual 3'-Deoxy 3'-Acylamino Spectinomycin Compounds:

3'-Dihydro-3'-deoxy-4(R)-(3-pyridin-3yl)propionylamino spectinomycin Dihydrochloride (1299)

$^1$H NMR ($D_2O$, 500 MHz): δ 8.74-8.65 (2H, m), 8.55-8.50 (1H, m), 8.03 (1H, dd, J1=8.0, J2=5.5 Hz), 4.89 (1H, s), 4.77-4.75 (2H, m), 4.36 (1H, t, J=10.5 Hz), 4.109 (1H, t, J=3.0 Hz), 4.02-3.92 (2H, m), 3.92-3.82 (1H, m), 3.51 (1H, dd, J1=11.5 Hz, J2=2.5 Hz), 3.26 (1H, dd, J1=10.0, J2=2.5 Hz), 2.83 (6H, br s), 2.81-2.76 (2H, m), 1.90-1.80 (1H, m), 1.60-1.52 (1H, m), 1.22 (3H, d, J=6.0 Hz); MS (ESI): m/z 467 ($M^+$+H).

3'-Dihydro-3'-deoxy-4(R)-(pyridin-2-yl)acetylamino spectinomycin Dihydrochloride (1329)

$^1$H NMR ($D_2O$, 500 MHz): δ 8.45 (1H, d, J=6.0 Hz), 8.57 (1H, t, J=7.5 Hz), 8.00 (1H, t, J=7.0 Hz), 7.97 (1H, d, J=8.0 Hz), 5.01 (1H, s), 4.77-4.75 (2H, m), 4.40 (1H, t, J=10.5 Hz), 4.23 (1H, t, J=6.5 Hz), 4.21 (1H, m), 4.13-4.02 (1H, m), 4.04 (1H, t, J=10.0 Hz), 3.97 (1H, t, J=10.0 Hz), 3.52 (1H, dd, J1=11.5, J2=2.5 Hz), 3.27 (1H, dd, J1=10.5, J2=2.5 Hz), 2.83 (3H, s), 2.82 (3H, s), 1.96-1.87 (1H, m), 1.81-1.74 (1H, m), 1.27 (3H, d, J=6.0 Hz); $^{13}$C NMR ($D_2O$, 75 MHz): δ 146.7 141.0, 138.2, 128.0, 125.4 92.6, 89.7, 69.53, 67.6, 65.6, 65.1, 61.1, 59.6, 58.0, 51.8, 33.7, 30.3, 30.2, 19.4; MS (ESI): m/z 453 ($M^+$+H).

3'-Dihydro-3'-deoxy-4(R)-(tert-butylamino)-acetylamino spectinomycin Dihydrochloride (1351)

$^1$HNMR ($D_2O$, 500 MHz): δ 4.96 (1H, s), 4.78-4.76 (2H, m), 4.40 (1H, t, J=10.0 Hz), 4.25-4.19 (1H, m), 4.09-4.01 (2H, m), 4.01-3.94 (1H, m), 3.92 (1H, d, J=8.0 Hz), 3.54 (1H, dd, J1=10.5, J2=2.5 Hz), 3.27 (1H, dd, J1=10.5, J2=2.5 Hz), 2.85 (3H, s), 2.84 (3H, s), 1.97-1.88 (1H, m), 1.82-1.74 (1H, m), 1.39 (9H, s), 1.27 (3H, d, J=6.0 Hz); $^{13}$C NMR ($D_2O$, 75 MHz): δ 92.6, 89.7, 69.6, 67.6, 65.6, 65.2, 59.7, 58.1, 57.4, 51.6, 42.2, 33.7, 30.4, 30.3, 24.4, 19.4; MS (ESI): m/z 447 ($M^+$+H).

3'-Dihydro-3'-deoxy-4(R)-4-fluorobenzoylamino spectinomycin Dihydrochloride (1364)

$^1$H NMR ($D_2O$, 500 MHz): δ 7.82-7.76 (2H, m), 7.32-7.24 (2H, m), 5.13 (1H, s), 4.47 (1H, t, J=10.5 Hz), 4.39 (1H, t, J=3.0 Hz), 4.20-4.12 (1H, m), 4.08 (1H, t, J=10.0 Hz), 4.01

(1H, t, J=10.0 Hz), 3.58 (1H, dd, J1=11.0, J2=2.5 Hz), 3.31 (1H, dd, J1=10.5, J2=2.5 Hz), 2.88 (3H, s), 2.87 (3H, s), 2.05-1.96 (1H, m), 1.96-1.88 (1H, m), 1.30 (3H, d, J=6.0 Hz); $^{13}$C NMR (D$_2$O, 75 MHz): δ 129.6 (d, J=9.4 Hz), 115.3 (d, J=22.1 Hz), 92.7, 90.1, 69.6, 67.7, 65.6, 65.2, 61.2, 59.7, 58.1, 52.2, 34.0, 30.4, 30.3, 19.5; MS (ESI): m/z 456 (M$^+$+H).

3'-Dihydro-3'-deoxy-4(R)-furan-2-carboxylicamino spectinomycin Dihydrochloride (1365)

$^1$H NMR (D$_2$O, 500 MHz): δ 7.70 (1H, d, J=1.0 Hz), 7.23 (1H, d, J=3.5 Hz), 6.65 (1H, dd, J1=3.5, J2=1.5 Hz), 5.14 (1H, s), 4.43 (1H, t, J=10.5 Hz), 4.38-4.33 (1H, m), 4.22-4.13 (1H, m), 4.05 (1H, t, J=10.0 Hz), 3.98 (1H, t, J=10 Hz), 3.55 (1H, dd, J1=11.0, J2=2.5 Hz), 3.28 (1H, dd, J1=10.5, J2=2.5 Hz), 2.85 (3H, s), 2.84 (3H, s), 2.02-1.93 (1H, m), 1.90-1.81 (1H, m), 1.27 (3H, d, J=6.0 Hz); MS (ESI): m/z 427 (M$^+$+H).

3'-Dihydro-3'-deoxy-4(R)-dodecanoylamino spectinomycin Dihydrochloride (1366)

$^1$H NMR (D$_2$O, 500 MHz): δ 4.98 (1H, s), 4.40 (1H, dd, J1=10.5, J2=10.0 Hz), 4.16 (1H, t, J=3.0 Hz), 4.09-4.02 (1H, m), 4.02 (1H, t, J=10.0 Hz), 3.97 (1H, t, J=10.0 Hz), 3.52 (1H, dd, J1=11.0, J2=3.0 Hz), 3.26 (1H, dd, J1=10.5, J2=3.0 Hz), 2.84 (3H, s), 2.83 (3H, s), 2.32 (2H, t, J=7.0 Hz), 1.94-1.85 (1H, m), 1.75-1.68 (1H, m), 1.66-1.55 (2H, m), 1.32-1.24 (19H, m), 0.86 (3H, t, J=7.0 Hz); MS (ESI): m/z 516 (M$^+$+H).

3'-Dihydro-3'-deoxy-4(R)-(4-fluoro-phenyl)-acetylamino spectinomycin Dihydrochloride (1367)

$^1$H NMR (D$_2$O, 500 MHz): δ 7.82-7.74 (2H, m), 7.30-7.20 (2H, m), 5.11 (1H, s), 4.45 (1H, t, J=11.0 Hz), 4.37 (1H, t, J=3.0 Hz), 4.17-4.10 (1H, m), 4.06 (1H, t, J=10.0 Hz), 3.99 (1H, t, J=10.0 Hz), 3.52 (1H, dd, J1=11.0, J2=3.0 Hz), 3.28 (1H, dd, J1=10.0, J2=2.5 Hz), 2.86 (3H, s), 2.84 (3H, s), 2.04-1.94 (2H, m), 1.94-1.86 (1H, m), 1.28 (3H, d, J=6.0 Hz); $^{13}$C NMR (D$_2$O, 75 MHz): δ 129.5 (d, J=9.4 Hz), 115.3 (d, J=22.2 Hz), 92.7, 90.0, 69.6, 67.7, 65.6, 65.2, 61.1, 59.7, 58.1, 52.2, 33.9, 30.4, 30.3, 19.5; MS (ESI): m/z 470 (M$^+$+H).

3'-Dihydro-3'-deoxy-4(R)-(pyridin-3-yl)acetylamino spectinomycin Dihydrochloride (1368)

$^1$H NMR (D$_2$O, 500 MHz): δ 8.80-8.70 (2H, m), 8.56-8.50 (1H, m), 8.07 (1H, dd, J1=7.5, J2=6.0 Hz), 5.02 (1H, s), 4.40 (1H, t, J=10.5 Hz), 4.19 (1H, t, J=3.5 Hz), 4.14-3.94 (6H, m), 3.52 (1H, dd, J1=11.0, J2=2.5 Hz), 3.27 (1H, dd, J1=10.0, J2=2.5 Hz), 2.83 (3H, s), 2.82 (3H, s), 1.96-1.86 (1H, m), 1.80-1.70 (1H, m), 1.26 (3H, d, J=6.0 Hz); MS (ESI): m/z 453 (M$^+$+H).

3'-Dihydro-3'-deoxy-4(R)-(3-methyl)-butanoylamino spectinomycin Dihydrochloride (1369)

$^1$H NMR (D$_2$O, 500 MHz): δ 5.00 (1H, s), 4.40 (1H, t, J=10.5 Hz), 4.20-4.15 (1H, m), 4.10-3.92 (3H, m), 3.52 (1H, dd, J1=11.0, J2=2.5 Hz), 3.26 (1H, dd, J1=10.0, J2=2.5 Hz), 2.84 (3H, s), 2.83 (3H, s), 2.19 (2H, d, J=8.0 Hz), 2.04-1.96 (1H, m), 1.94-1.86 (1H, m), 1.76-1.68 (1H, m), 1.25 (3H, d, J=6.0 Hz), 0.97-0.88 (6H, m); $^{13}$CNMR (D$_2$O, 75 MHz): δ 92.6, 90.0, 69.6, 67.6, 65.6, 65.1, 61.1, 59.6, 58.1, 51.3, 44.3, 34.00, 30.3, 30.2, 25.8, 21.4, 21.0, 19.4; MS (ESI): m/z 418 (M$^+$+H).

3'-Dihydro-3'-deoxy-4(R)-pyridin-2-carboxylicamino spectinomycin Dihydrochloride (1370)

$^1$H NMR (D$_2$O, 500 MHz): δ 8.66 (1H, d, J=4.5 Hz), 8.10 (2H, d, J=3.5 Hz), 7.74-7.65 (1H, m), 5.16 (1H, s), 4.45 (1H, t, J=11.0 Hz), 4.39 (1H, t, J=3.5 Hz), 4.25-4.15 (1H, m), 4.07 (1H, t, J=10.0 Hz), 4.00 (1H, t, J=10.5 Hz), 3.56 (1H, dd, J1=11.0, J2=2.5 Hz), 3.28 (1H, dd, J1=10.0, J2=2.5 Hz), 2.86 (3H, s), 2.84 (3H, s), 2.02-1.98 (1H, m), 1.97-1.91 (1H, m), 1.28 (3H, d, J=6.0 Hz); $^{13}$C NMR (D$_2$O, 75 MHz): δ 148.1, 138.8, 127.3, 122.5, 92.5, 69.63, 67.6, 65.6, 65.3, 61.1, 59.7, 58.1, 33.7, 30.4, 30.2, 19.4; MS (ESI): m/z 439 (M$^+$+H).

3'-Dihydro-3'-deoxy-4(R)-phenylacetylamino spectinomycin Dihydrochloride (1398)

$^1$H NMR (D$_2$O, 500 MHz): δ 7.41 (2H, t, J=7.3 Hz), 7.31-7.36 (3H, m), 5.45 (1H, s), 4.39 (1H, t, J=10.7 Hz), 4.15 (1H, br s), 3.94-4.05 (3H, m), 3.64-3.67 (2H, m), 3.50-3.58 (3H, m), 2.81 (6H, s), 1.85-1.91 (1H, m), 1.71 (1H, d, J=14.6 Hz), 1.24 (3H, d, J=5.8 Hz); $^{13}$C NMR (CD$_3$OD, 125 MHz): δ 135.4, 128.7, 126.4, 93.5, 90.6, 70.4, 66.2, 61.7, 58.5, 52.3, 41.9, 37.5, 34.6, 30.0, 19.7; MS (ESI): m/z 452 (M$^+$+H).

3'-Dihydro-3'-deoxy-4(R)-p-tolylacetylamino spectinomycin Dihydrochloride (1399)

$^1$H NMR (D$_2$O, 500 MHz): δ 7.20 (4H, q, J=7.8 Hz), 4.96 (1H, s), 4.36 (1H, t, J=10.5 Hz), 4.12 (1H, br s), 3.92-4.03 (2H, m), 3.60 (2H, s), 3.49 (2H, d, J=10.7 Hz), 3.24 (2H, d, J=10.2 Hz), 2.80 (6H, s), 2.30 (3H, s), 1.85 (1H, t, J=11.4 Hz), 1.68 (1H, d, J=14.1 Hz), 1.21 (3H, d, J=5.86 Hz); $^{13}$C NMR (CD$_3$OD, 125 MHz): δ 175.7, 137.7, 133.8, 130.3, 130.29, 95.1, 92.2, 72.0, 68.5, 63.2, 60.0, 43.0, 39.0, 36.1, 31.9; MS (ESI): m/z 466 (M$^+$+H).

3'-Dihydro-3'-deoxy-4(R)-(3-methoxy-phenyl)acetylamino spectinomycin Dihydrochloride (1400)

$^1$H NMR (D$_2$O, 500 MHz): δ 7.33 (1H, t, J=8.0 Hz), 6.93 (3H, t, J=9.5 Hz), 4.97 (1H, s), 4.73 (2H, s), 4.36 (1H, t, J=10.5 Hz), 4.13 (1H, s), 3.92-4.04 (3H, m), 3.81 (3H, s), 3.63 (3H, s), 3.48-3.57 (1H, m), 3.24 (1H, d, J=10.0 Hz), 2.80 (6H, s), 1.86 (1H, t, J=11.4 Hz), 1.69 (1H, d, J=14.1 Hz), 1.22 (3H, d, J=6.3 Hz); $^{13}$C NMR (CD$_3$OD, 125 MHz): δ 175.3, 161.4, 138.3, 130.6, 122.5, 115.8, 113.5, 95.1, 92.2, 71.9, 67.8, 63.2, 55.7, 43.5, 39.0; MS (ESI): m/z 482 (M$^+$+H).

3'-Dihydro-3'-deoxy-4(R)-[3,4-(methylene dioxy) phenyl]acetyl amino spectinomycin Dihydrochloride (1411)

$^1$H NMR (D$_2$O, 500 MHz): δ 6.76-6.86 (3H, m), 5.95 (2H, s), 4.96 (1H, s), 4.36 (1H, t, J=10.5 Hz), 4.12 (1H, s), 3.92-4.02 (4H, m), 3.48-3.56 (3H, m), 3.23 (1H, d, J=9.7 Hz), 2.79 (6H, s), 1.86 (1H, t, J=11.4 Hz), 1.69 (1H, d, J=14.4 Hz), 1.22 (3H, d, J=5.8 Hz); $^{13}$C NMR (CD$_3$OD, 125 MHz): δ 130.5, 123.4, 110.5, 102.4, 95.1, 72.0, 67.2, 63.2, 60.0, 43.0, 39.0, 31.8, 21.3; MS (ESI): m/z 496 (M$^+$+H).

3'-Dihydro-3'-deoxy-4(R)-m-tolylacetylamino spectinomycin Dihydrochloride (1412)

$^1$H NMR (D$_2$O, 500 MHz): δ 7.28 (1H, t, J=7.5 Hz), 7.09-7.18 (3H, m), 4.97 (1H, s), 4.37 (1H, t, J=10.7 Hz), 4.12 (1H, s), 3.92-4.02 (2H, m), 3.61 (2H, s), 3.49 (2H, d, J=10.9 Hz), 3.24 (2H, d, J=10.0 Hz), 2.79 (6H, s), 2.31 (3H, s), 1.85 (1H, t, J=11.4 Hz), 1.69 (1H, d, J=13.9 Hz), 1.22 (3H, d, J=5.8 Hz); MS (ESI): m/z 466 (M$^+$+H).

3'-Dihydro-3'-deoxy-4(R)-(pyridin-4-yl)acetylamino spectinomycin Dihydrochloride (1413)

$^1$H NMR (D$_2$O, 500 MHz): δ 8.71 (2H, t, J=6.3 Hz), 7.97 (1H, d, J=5.8 Hz), 7.89 (1H, d, J=6.1 Hz), 4.99 (1H, s), 4.36 (1H, t, J=10.0 Hz), 4.17 (1H, d, J=10.9 Hz), 3.92-4.18 (3H, m), 3.62 (1H, q, J=7.0 Hz), 3.50 (1H, d, J=10.9 Hz), 3.41 (1H, d, J=11.9 Hz), 3.24 (1H, d, J=9.7 Hz), 2.96-3.02 (1H, m), 2.81 (6H, s), 1.86-1.89 (1H, m), 1.64-1.74 (1H, m), 1.23 (3H, d, J=5.3 Hz); $^{13}$C NMR (CD$_3$OD, 125 MHz): δ 139.4, 136.8, 130.9, 129.5, 128.7, 127.2, 95.1, 92.2, 72.0, 68.6, 67.8, 63.2, 53.9, 49.7, 43.4, 39.0; MS (ESI): m/z 453 (M$^+$+H).

3'-Dihydro-3'-deoxy-4(R)-(pyrimidin-2-yl)acetylamino spectinomycin Dihydrochloride (1439)

$^1$H NMR (D$_2$O, 500 MHz): δ 8.27 (1H, d, J=7.5 Hz), 7.99 (1H, d, J=6.35 Hz), 7.00 (1H, t, J=7.0 Hz), 5.06 (1H, s), 4.35-4.43 (2H, m), 4.00-4.08 (2H, m), 3.89-3.98 (1H, m), 3.54 (2H, dd, J=10.9 Hz), 3.43-3.46 (1H, m), 3.35-3.40 (1H, m), 3.25 (1H, t, J=6.3 Hz), 2.82 (6H, s), 2.14-2.15 (2H, m), 1.25 (3H, d, J=5.6 Hz); MS (ESI): m/z 454 (M$^+$+H).

3'-Dihydro-3'-deoxy-4(R)-(4-methoxy-phenyl)acetylamino spectinomycin Dihydrochloride (1446)

$^1$H NMR (D$_2$O, 500 MHz): δ 7.25 (2H, d, J=8.5 Hz), 6.98 (2H, d, J=8.5 Hz), 4.97 (1H, s), 4.38 (1H, t, J=10.1 Hz), 4.13 (1H, s), 3.93-4.04 (3H, m), 3.82 (3H, s), 3.49-3.64 (3H, m), 3.34 (1H, s), 3.25 (1H, d, J=7.57 Hz), 2.80 (6H, s), 1.86 (1H, t, J=11.4 Hz), 1.70 (1H, d, J=14.8 Hz), 1.23 (3H, d, J=6.1 Hz); MS (ESI): m/z 482 (M$^+$+H).

3'-Dihydro-3'-deoxy-4(R)-(2,3-difluoro-phenyl)acetylamino spectinomycin Dihydrochloride (1447)

$^1$H NMR (D$_2$O, 500 MHz): δ 7.23 (1H, q, J=8.8 Hz), 7.14 (1H, q, J=8.0 Hz), 7.09 (1H, t, J=7.5 Hz), 5.01 (1H, s), 4.39 (1H, t, J=10.5 Hz), 4.17 (1H, s), 3.94-4.10 (3H, m), 3.77 (2H, s), 3.50-3.58 (2H, m), 3.34 (1H, s), 3.25 (1H, dd, J=2.6, 10.2 Hz), 2.82 (6H, s), 1.86-1.89 (1H, m), 1.75 (1H, d, J=14.6 Hz), 1.25 (3H, d, J=6.1 Hz); MS (ESI): m/z 488 (M$^+$+H).

3'-Dihydro-3'-deoxy-4(R)-(2-methoxy-phenyl)acetylamino spectinomycin Dihydrochloride (1448)

$^1$H NMR (D$_2$O, 500 MHz): δ 7.36 (1H, t, J=7.32 Hz), 7.24 (1H, d, J=7.3 Hz), 7.05 (1H, d, J=8.3 Hz), 7.00 (1H, t, J=7.5 Hz), 4.96 (1H, s), 4.37 (1H, t, J=10.7 Hz), 4.12 (1H, s), 3.93-4.06 (3H, m), 3.82 (3H, s), 3.50-3.63 (3H, m), 3.33 (2H, s), 3.25 (1H, dd, J=2.4, 10.5 Hz), 2.80 (6H, s), 1.84-1.90 (1H, m), 1.72 (1H, d, J=14.4 Hz), 1.25 (3H, d, J=6.1 Hz); MS (ESI): m/z 482 (M$^+$+H).

3'-Dihydro-3'-deoxy-4(R)-(thiazol-4-yl)acetylamino spectinomycin trihydrobromide (1443)

$^1$H NMR (D$_2$O, 500 MHz): δ 9.00 (1H, s), 7.45 (1H, s), 4.99 (1H, s), 4.40 (1H, t, J=10.0 Hz), 4.17 (1H, m), 4.08-3.94 (3H, m), 3.90 (2H, s), 3.64 (1H, q, J=7.0 Hz), 3.51 (1H, dd, J$_1$=11.0 Hz, J$_2$=2.5 Hz), 3.25 (1H, dd, J$_1$=10.0 Hz, J$_2$=2.5 Hz), 2.82 (3H, s), 2.81 (3H, s), 1.88 (1H, m), 1.78 (1H, m), 1.25 (3H, d, J=6.0 Hz). MS (ESI): m/z 459 (M$^+$+H).

3'-Dihydro-3'-deoxy-4(R)-(2-aminothiazol-4-yl) acetylamino spectinomycin trihydrobromide (1444)

$^1$H NMR (D$_2$O, 500 MHz): δ 6.61 (1H, s), 4.98 (1H, s), 4.39 (1H, t, J=10.0 Hz), 4.18 (1H, t, J=3.0 Hz), 4.05-3.94 (3H, m), 3.77 (1H, m), 3.71 (1H, d, J=6.5 Hz), 3.63 (1H, q, J=7.0 Hz), 3.51 (1H, dd, J$_1$=11.0 Hz, J$_2$=2.5 Hz), 3.22 (1H, dd, J$_1$=10.5 Hz, J$_2$=2.5 Hz), 2.83 (3H, s), 2.82 (3H, s), 1.93-1.87 (1H, m), 1.77-1.74 (1H, m), 1.25 (3H, d, J=6.0 Hz). MS (ESI): m/z 474 (M$^+$+H).

3'-Dihydro-3'-deoxy-4(R)-(5-fluoropyridin-2-yl) acetylamino spectinomycin trihydrobromide (1445)

$^1$H NMR (D$_2$O, 500 MHz): δ 8.46 (1H, br), 7.76 (1H, br), 7.53 (1H, br), 5.00 (1H, s), 4.40 (1H, t, J=10.5 Hz), 4.18 (1H, t, J=3.0 Hz), 4.08-3.91 (5H, m), 3.64 (1H, q, J=7.0 Hz), 3.51 (1H, dd, J$_1$=11.0 Hz, J$_2$=2.5 Hz), 3.25 (1H, dd, J$_1$=10.0 Hz, J$_2$=2.5 Hz), 2.82 (3H, s), 2.81 (3H, s), 1.92-1.83 (1H, m), 1.78-1.75 (1H, m), 1.25 (3H, d, J=6.5 Hz). MS (ESI): m/z 471 (M$^+$+H).

3'-Dihydro-3'-deoxy-4(R)-(pyridazin-3-yl)acetylamino spectinomycin tetrahydrobromide (1449)

$^1$H NMR (D$_2$O, 500 MHz): δ 9.18 (1H, br), 7.90 (2H, m), 5.01 (1H, s), 4.39 (1H, t, J=10.5 Hz), 4.19 (1H, m), 4.11 (2H, m), 4.03 (1H, t, J=10.0 Hz), 3.96 (1H, t, J=10.0 Hz), 3.77 (1H, t, J=10.0 Hz), 3.51 (1H, dd, J$_1$=11.3 Hz, J$_2$=2.5 Hz), 3.41 (1H, t, J=9.5 Hz), 3.25 (1H, dd, J$_1$=10.3 Hz, J$_2$=3.0 Hz), 3.22 (1H, dd, J$_1$=10.75 Hz, J$_2$=2.5 Hz), 2.82 (3H, s), 2.81 (3H, s), 1.92-1.86 (1H, m), 1.78-1.75 (1H, m), 1.25 (3H, d, J=5.5 Hz). MS (ESI): m/z 454 (M$^+$+H).

3'-Dihydro-3'-deoxy-4(R)-(pyrazine-2-yl)carboxylicamino spectinomycin tetrahydrobromide (1453)

$^1$H NMR (D$_2$O, 400 MHz): δ 9.20 (1H, d, J=1.4 Hz), 8.84 (1H, d, J=2.5 Hz), 8.75 (1H, dd, J=2.5 Hz, 1.5 Hz), 5.16 (1H, s), 4.90 (1H, s), 4.51-4.36 (2H, m), 4.21 (1H, d, J=5.8 Hz), 4.08 (1H, t, J=9.8 Hz), 3.99 (1H, t, J=10.1 Hz), 3.60-3.53 (1H, m), 3.29 (1H, dd, J=10.2 Hz, 2.8 Hz), 2.85 (6H, d, J=8.5 Hz), 2.04-1.91 (2H, m), 1.28 (3H, d, J=6.1 Hz). MS (ESI): m/z 440 (M$^+$+H).

3'-Dihydro-3'-deoxy-4(R)-(benzooxazol-2-yl)acetylamino spectinomycin trihydrobromide (1465)

$^1$H NMR (D$_2$O, 400 MHz): δ 7.82-7.69 (1H, m), 7.67 (1H, dd, J=6.7 Hz, 2.3 Hz), 7.46 (2H, pd, J=7.5 Hz, 3.8 Hz), 5.02 (1H, s), 4.48-4.35 (1H, m), 4.22 (1H, t, J=3.0 Hz), 4.15-4.05 (2H, m), 4.05-3.93 (2H, m), 3.53 (1H, dd, J=11.1 Hz, 2.6 Hz), 3.26 (1H, dt, J=15.6 Hz, 7.9 Hz), 2.83 (8H, s), 1.96-1.85 (1H, m), 1.82 (1H, d, J=14.4 Hz), 1.27 (3H, d, J=6.1 Hz). MS (ESI): m/z 493 (M$^+$+H).

3'-Dihydro-3'-deoxy-4(R)-(1H-imidazol-4-yl)acetylamino spectinomycin tetradrobromide (1466)

$^1$H NMR (D$_2$O, 400 MHz): δ 8.67 (1H, d, J=1.4 Hz), 7.36 (1H, d, J=1.3 Hz), 5.00 (1H, s), 4.90 (1H, s), 4.40 (1H, dd, J=10.9 Hz, 10.0 Hz), 4.19 (1H, t, J=3.0 Hz), 4.13-3.90 (3H, m), 3.88 (2H, d, J=3.5 Hz), 3.54 (1H, dd, J=7.9 Hz, 3.3 Hz), 3.27 (1H, dd, J=10.2 Hz, 2.7 Hz), 2.83 (6H, s), 1.96-1.85 (1H, m), 1.76 (1H, dd, J=12.3 Hz, 2.3 Hz), 1.26 (3H, d, J=6.1 Hz). MS (ESI): m/z 442 (M$^+$+H).

3'-Dihydro-3'-deoxy-4(R)-[2(S)-amino]propanoylamino spectinomycin Trihydrochloride (1467)

$^1$H NMR (D$_2$O, 400 MHz): δ 4.23 (2H, t, J=8.0 Hz), 3.94-4.06 (2H, m), 3.76-3.93 (3H, m), 3.38 (1H, d, J=10.3 Hz), 3.22 (1H, s), 3.11 (1H, d, J=8.8 Hz), 2.67 (6H, d, J=2.6 Hz), 1.70-1.80 (1H, m), 1.59 (1H, d, J=14.1 Hz), 1.36 (3H, d, J=7.0 Hz), 1.09 (3H, d, J=6.0 Hz); MS (ESI): m/z 405 (M$^+$+H).

3'-Dihydro-3'-deoxy-4(R)-(3-amino)propanoylamino spectinomycin Trihydrochloride (1469)

$^1$H NMR (D$_2$O, 400 MHz): δ 4.31 (2H, t, J=8 Hz), 4.10 (1H, s), 3.83-4.02 (3H, m), 3.44 (2H, d, J=8 Hz), 3.14-3.24 (3H, m), 2.75 (6H, d, J=5.8 Hz), 2.67 (2H, t, J=8.0 Hz), 1.76-1.86 (1H, m), 1.66 (1H, d, J=16 Hz), 1.16 (3H, d, J=4.0 Hz); MS (ESI): m/z 405 (M$^+$+H).

3'-Dihydro-3'-deoxy-4(R)-(2-amino)acetylamino spectinomycin Trihydrochloride (1470)

$^1$H NMR (D$_2$O, 400 MHz): δ 4.26 (2H, t, J=8.0 Hz), 4.08 (1H, s), 3.71-3.96 (4H, m), 3.36-3.47 (1H, m), 3.24 (2H, s), 3.13 (1H, d, J=8.0 Hz), 2.70 (6H, d, J=5.8 Hz), 1.73-1.83 (1H, m), 1.64 (1H, d, J=12 Hz), 1.12 (3H, d, J=4.0 Hz); MS (ESI): m/z 391 (M$^+$+H).

3'-Dihydro-3'-deoxy-4(R)-[(2S,3S)-2-amino,3-methyl]pentanoylamino spectinomycin Trihydrochloride (1485)

$^1$H NMR (D$_2$O, 400 MHz): δ 4.39 (2H, t, J=8 Hz), 4.20 (1H, s), 3.88-4.06 (4H, m), 3.50 (1H, d, J=12 Hz), 3.23 (1H, d, J=12 Hz), 2.79 (6H, d, J=8 Hz), 1.85-2.01 (2H, m), 1.70 (1H, d, J=16 Hz), 1.40-1.53 (1H, m), 1.22 (3H, d, J=4.0 Hz), 1.10-1.19 (1H, m), 0.98 (3H, d, J=8 Hz), 0.90 (3H, t, J=8 Hz); MS (ESI): m/z 447 (M$^+$+H).

3'-Dihydro-3'-deoxy-4(R)-[2(S)-amino,3-methyl]butanoylamino spectinomycin Trihydrochloride (1486)

$^1$H NMR (D$_2$O, 400 MHz): δ 4.30 (2H, t, J=8.0 Hz), 4.14 (1H, s), 3.80-4.00 (4H, m), 3.44 (1H, d, J=8.0 Hz), 3.27 (1H, s), 3.17 (1H, d, J=8.0 Hz), 2.74 (6H, d, J=4.0 Hz), 2.08-2.20 (1H, m), 1.79-1.90 (1H, m), 1.64 (1H, d, J=16.0 Hz), 1.15 (3H, d, J=6.0 Hz), 0.92 (6H, t, J=8.0 Hz); MS (ESI): m/z 433 (M$^+$+H).

3'-Dihydro-3'-deoxy-4(R)-[3(R)-amino,3-(4-fluorophenyl)]propanoyl-amino spectinomycin Trihydrochloride (1487)

$^1$H NMR (D$_2$O, 400 MHz): δ 7.42 (2H, d, J=4.0 Hz), 7.19 (2H, d, J=4.0 Hz), 4.26 (2H, t, J=8.0 Hz), 3.97 (1H, s), 3.90 (2H, t, J=8.0 Hz), 3.68-3.79 (2H, m), 3.44 (2H, d, J=12.0 Hz), 3.19 (2H, d, J=8.0 Hz), 3.03 (2H, d, J=8.0 Hz), 2.73 (6H, s), 1.74 (1H, t, J=12.0 Hz), 1.47 (1H, d, J=12.0 Hz), 1.13 (3H, d, J=4.0 Hz); MS (ESI): m/z 499 (M$^+$+H).

3'-Dihydro-3'-deoxy-4(R)-(thiazol-2-yl)acetylamino spectinomycin tetradrobromide (1489)

$^1$H NMR (D$_2$O, 400 MHz): δ 7.88 (1H, d, J=3.6 Hz), 7.74-7.65 (1H, m), 4.98 (1H, s), 4.74 (1H, t, J=2.7 Hz), 4.37 (1H, dd, J=11.0 Hz, 9.9 Hz), 4.17 (1H, t, J=3.1 Hz), 4.10-3.89 (4H, m), 3.52-3.47 (1H, m), 3.24 (1H, dd, J=10.1 Hz, 2.9 Hz), 2.81 (7H, s), 1.94-1.82 (1H, m), 1.79-1.71 (1H, m), 1.23 (3H, d, J=6.1 Hz). MS (ESI): m/z 459 (M$^+$+H).

3'-Dihydro-3'-deoxy-4(R)-(5-nitropyridin-2-yl)acetylamino spectinomycin trihydrobromide (1490)

$^1$H NMR (D$_2$O, 400 MHz): δ 9.34 (1H, s), 8.64 (1H, d, J=8.6 Hz), 7.66 (1H, d, J=8.6 Hz), 5.02 (1H, s), 4.76 (1H, t, J=2.8 Hz), 4.46-4.31 (1H, m), 4.20 (1H, t, J=3.1 Hz), 4.15-3.92 (3H, m), 3.81-3.55 (1H, m), 3.53 (1H, dd, J=11.2 Hz, 2.7 Hz), 3.33-3.22 (1H, m), 2.83 (6H, d, J=1.9 Hz), 1.99-1.83 (1H, m), 1.78 (1H, d, J=14.5 Hz), 1.26 (3H, d, J=6.1 Hz). MS (ESI): m/z 498 (M$^+$+H).

3'-Dihydro-3'-deoxy-4(R)-(benzothiazol-2-yl)acetylamino spectinomycin trihydrobromide (1491)

$^1$H NMR (D$_2$O, 400 MHz): δ 8.03 (2H, dd, J=17.1 Hz, 8.1 Hz), 7.65-7.57 (1H, m), 7.57-7.48 (1H, m), 5.03 (1H, s), 4.77 (1H, t, J=2.7 Hz), 4.44-4.37 (1H, m), 4.23 (1H, t, J=3.1 Hz), 4.16-3.89 (4H, m), 3.53 (1H, dd, J=8.3 Hz, 2.8 Hz), 3.27 (1H, dd, J=10.1 Hz, 2.8 Hz), 2.83 (6H, d, J=5.2 Hz), 2.23 (1H, s), 1.97-1.85 (1H, m), 1.80 (1H, dd, J=12.2 Hz, 2.3 Hz), 1.26 (3H, d, J=6.1 Hz). MS (ESI): m/z 509 (M$^+$+H).

3'-Dihydro-3'-deoxy-4(R)-(2-fluorobenzene-1-yl)carboxylicamino spectinomycin dihydrochloride (1492)

$^1$H NMR (D$_2$O, 400 MHz): δ 7.62 (2H, m), 7.38-7.24 (2H, m), 5.05 (1H, s), 4.77 (1H, s), 4.47 (1H, dd, J=10.9 Hz, 10.0 Hz), 4.40 (1H, t, J=2.9 Hz), 4.18-3.95 (3H, m), 3.58 (1H, m), 3.30 (1H, dd, J=10.2 Hz, 2.8 Hz), 2.87 (6H, d, J=7.8 Hz), 2.06-1.87 (2H, m), 1.30 (3H, d, J=6.1 Hz). MS (ESI): m/z 456 (M$^+$+H).

3'-Dihydro-3'-deoxy-4(R)-(2(S)-4-amino-2-hydroxy)butanoylamino spectinomycin trihydrochloride (1493)

$^1$H NMR (D$_2$O, 400 MHz): δ 5.03 (1H, s), 4.76 (1H, s), 4.45-4.34 (2H, m), 4.19 (1H, t, J=3.1 Hz), 4.14-3.92 (3H, m), 3.56-3.50 (1H, m), 3.27 (1H, dd, J=10.2 Hz, 2.8 Hz), 3.16 (2H, t, J=6.7 Hz), 2.84 (6H, d, J=3.4 Hz), 2.16 (1H, m), 2.07-1.89 (2H, m), 1.78 (1H, dd, J=12.4 Hz, 2.2 Hz), 1.26 (3H, d, J=6.1 Hz). MS (ESI): m/z 435 (M$^+$+H).

3'-Dihydro-3'-deoxy-4(R)-[2(R)-amino]propanoylamino spectinomycin Trihydrochloride (1501)

$^1$H NMR (D$_2$O, 400 MHz): δ 4.34 (2H, t, J=8.0 Hz), 4.15 (1H, s), 4.08 (1H, d, J=8.0 Hz), 3.88-4.04 (2H, m), 3.46-3.52 (1H, m), 3.31 (2H, s), 3.19-3.25 (1H, m), 2.79 (6H, d, J=4.0 Hz), 1.82-1.93 (1H, m), 1.71 (1H, d, J=16.0 Hz), 1.49 (3H, d, J=8.0 Hz). 1.21 (3H, d, J=8.0 Hz). MS (ESI): m/z 405 (M$^+$+H).

3'-Dihydro-3'-deoxy-4(R)-[2(S)-(2-aminoacetamido)-3-phenyl]-propanoylamino spectinomycin Trihydrochloride (1502)

$^1$H NMR (D$_2$O, 400 MHz): δ 7.07-7.25 (5H, m), 4.26-4.36 (2H, m), 3.85-3.94 (2H, m), 3.70-3.83 (3H, m), 3.38-3.50 (1H, m), 3.31 (2H, s), 3.15-3.23 (2H, m), 2.96-3.08 (2H, m), 2.77 (6H, d, J=4.0 Hz), 1.78-1.88 (1H, m), 1.54-1.69 (1H, m), 1.18 (3H, d, J=8.0 Hz). MS (ESI): m/z 538 (M⁺+H).

3'-Dihydro-3'-deoxy-4(R)-3-benzamido propanoylamino spectino-mycin Dihydrochloride (1503)

¹H NMR (D₂O, 400 MHz): δ 7.73 (2H, d, J=8.0 Hz), 7.57-7.63 (2H, m), 7.51 (2H, t, J=8.0 Hz), 4.34 (2H, t, J=8.0 Hz), 4.11 (1H, s), 3.93 (2H, p, J=8.0 Hz), 3.57-3.83 (3H, m), 3.43-3.51 (1H, m), 3.32 (1H, s), 3.19-3.25 (1H, m), 2.79 (6H, s), 2.51-2.71 (2H, m), 1.71-1.82 (1H, m), 1.55 (1H, d, J=12.0 Hz), 0.97 (3H, d, J=4.0 Hz). MS (ESI): m/z 509 (M⁺+H).

3'-Dihydro-3'-deoxy-4(R)-3-(2-phenylacetamido) propanoylamino spectinomycin Dihydrochloride (1504)

¹H NMR (D₂O, 400 MHz): δ 7.23-7.42 (5H, m), 4.35 (2H, t, J=8.0 Hz), 4.07 (1H, s), 3.83-4.01 (3H, m), 3.39-3.57 (3H, m), 3.17-3.36 (4H, m), 2.79 (6H, s), 2.46 (2H, br. s), 1.74-1.86 (1H, m), 1.58 (1H, d, J=12.0 Hz), 1.18 (3H, d, J=4.0 Hz). MS (ESI): m/z 523 (M⁺+H).

3'-Dihydro-3'-deoxy-4(R)-(2,2-diphenyl)acetylamino spectinomycin dihydrochloride (1514)

¹H NMR (D₂O, 400 MHz): δ 7.46-7.31 (10H, m), 5.30 (1H, s), 4.91 (1H, s), 4.76 (1H, s), 4.40 (1H, dd, J=11.0 Hz, 9.7 Hz), 4.23 (1H, t, J=3.0 Hz), 4.05-3.90 (3H, m), 3.53 (1H, dd, J=11.1 Hz, 2.7 Hz), 3.27 (1H, dd, J=9.9 Hz, 2.7 Hz), 2.84 (6H, s), 1.97-1.86 (1H, m), 1.77 (1H, dd, J=12.4 Hz, 2.2 Hz), 1.23 (3H, d, J=6.1 Hz). MS (ESI): m/z 528 (M⁺+H).

3'-Dihydro-3'-deoxy-4(R)-[(2(S)-amino,3-phenyl] propanoylamino spectinomycin Trihydrochloride (1515)

¹H NMR (400 MHz, D₂O): δ 7.32-7.42 (3H, m), 7.22-7.29 (2H, m), 4.29 (2H, t, J=8H Hz), 4.00 (1H, s), 3.83-3.94 (2H, m), 3.39-3.58 (2H, m), 3.15-3.34 (3H, m), 2.97-3.14 (2H, m), 2.77 (6H, s), 1.59-1.71 (1H, m), 1.09-1.17 (1H, m), 1.06 (3H, d, J=4.0 Hz). MS (ESI): m/z 481 (M⁺+H).

3'-Dihydro-3'-deoxy-4(R)-(5-bromopyridin-2-yl) acetylamino spectinomycin trihydrobromide (1516)

¹H NMR (D₂O, 400 MHz): δ 8.77 (1H, s), 8.33 (1H, s), 7.58 (1H, s), 5.03 (1H, s), 4.78 (1H, s), 4.42 (1H, dd, J=10.9 Hz, 9.9 Hz), 4.20 (1H, d, J=3.0 Hz), 4.14-3.95 (5H, m), 3.55 (1H, dd, J=11.2 Hz, 2.5 Hz), 3.29 (1H, dd, J=10.1 Hz, 2.7 Hz), 2.85 (6H, d, J=1.6 Hz), 1.96-1.88 (1H, m), 1.79 (1H, d, J=14.6 Hz), 1.28 (3H, d, J=6.1 Hz). MS (ESI): m/z 531, 533 (M⁺+H).

3'-Dihydro-3'-deoxy-4(R)-(2-phenylthiazol-4-yl) acetylamino spectinomycin trihydrobromide (1517)

¹H NMR (D₂O, 400 MHz): δ 7.94 (2H, dd, J=7.8 Hz, 1.7 Hz), 7.67-7.55 (3H, m), 7.51 (1H, s), 5.03 (1H, s), 4.48-4.38 (1H, m), 4.21 (1H, d, J=3.1 Hz), 4.14-3.92 (5H, m), 3.55 (1H, dd, J=11.1 Hz, 2.6), 3.29 (1H, dd, J=10.1 Hz, 2.8 Hz), 2.85 (6H, d, J=1.4 Hz), 1.95-1.87 (1H, m), 1.81 (1H, d, J=14.4 Hz), 1.27 (3H, d, J=6.1 Hz). MS (ESI): m/z 535 (M⁺+H).

3'-Dihydro-3'-deoxy-4(R)-(pyridin-2-yl)propanoylamino spectinomycin trihydrobromide (1518)

¹H NMR (D₂O, 400 MHz): δ 8.60-8.56 (1H, m), 8.45 (1H, td, J=8.0 Hz, 1.6 Hz), 7.88-7.82 (2H, m), 4.84 (1H, s), 4.76 (1H, s), 4.29 (1H, dd, J=10.9 Hz, 9.8 Hz), 4.03 (1H, d, J=2.9 Hz), 3.98-3.81 (3H, m), 3.44 (1H, d, J=11.2 Hz), 3.29 (2H, dd, J=11.6 Hz, 4.5 Hz), 3.22-3.15 (1H, m), 2.83 (2H, dd, J=10.2 Hz, 4.4 Hz), 2.75 (6H, s), 1.83-1.73 (1H, m), 1.52 (1H, d, J=14.6 Hz), 1.14 (3H, d, J=6.1 Hz). MS (ESI): m/z 467 (M⁺+H).

3'-Dihydro-3'-deoxy-4(R)-(5-phenylpyridin-2-yl) acetylamino spectinomycin trihydrobromide (1519)

¹H NMR (D₂O, 400 MHz): δ 8.91 (1H, s), 8.66 (1H, m), 7.88 (1H, m), 7.67 (2H, m), 7.50 (3H, m), 4.91 (1H, s), 4.65 (1H, s), 4.28 (1H, d, J=10.0 Hz), 4.12 (2H, d, J=8.2 Hz), 4.03-3.71 (3H, m), 3.41 (1H, s), 3.14 (1H, s), 2.70 (6H, d, J=7.8 Hz), 1.79 (1H, m), 1.68 (1H, d, J=11.0 Hz), 1.15 (3H, d, J=6.1 Hz). MS (ESI): m/z 529 (M⁺+H).

3'-Dihydro-3'-deoxy-4(R)-(2-(phenylamino)thiazol-4-yl)acetylamino spectinomycin trihydrobromide (1520)

¹H NMR (D₂O, 400 MHz): δ 7.60-7.54 (2H, m), 7.50-7.43 (3H, m), 6.76 (1H, s), 5.00 (1H, s), 4.42 (1H, dd, J=10.9 Hz, 9.9 Hz), 4.21 (1H, t, J=3.1 Hz), 4.12-3.95 (3H, m), 3.84-3.74 (2H, m), 3.57 (1H, dd, J=11.1 Hz, 2.6 Hz), 3.30 (1H, dd, J=10.2 Hz, 2.7), 2.86 (6H, d, J=1.4 Hz), 1.93 (1H, ddd, J=15.0 Hz, 10.3 Hz, 3.9 Hz), 1.78 (1H, dd, J=12.3 Hz, 2.2 Hz), 1.28 (3H, d, J=6.1 Hz). MS (ESI): m/z 550 (M⁺+H).

3'-Dihydro-3'-deoxy-4(R)-(5-(4-chlorophenyl)pyridin-2-yl)acetylamino spectinomycin trihydrobromide (1535)

¹H NMR (D₂O, 400 MHz): δ 8.92 (1H, d, J=2.2 Hz), 8.66 (1H, dd, J=8.4, 2.2 Hz), 7.90 (1H, d, J=8.4 Hz), 7.69-7.62 (2H, m), 7.56-7.50 (2H, m), 4.94 (1H, s), 4.67 (1H, m), 4.34-4.28 (1H, m), 4.13 (2H, m), 4.07-3.85 (3H, m), 3.56 (1H, q, J=7.1 Hz), 3.45 (1H, dd, J=11.1, 2.6 Hz), 3.19 (1H, dd, J=10.2, 2.7 Hz), 2.74 (6H, d, J=0.9 Hz), 1.90-1.78 (1H, m), 1.70 (1H, m), 1.19 (3H, d, J=6.1 Hz). MS (ESI): m/z 563 (M⁺+H).

3'-Dihydro-3'-deoxy-4(R)-(quinoline-8-yl)carbonylamino spec-tinomycin trihydrobromide (1536)

¹H NMR (D₂O, 400 MHz): δ 9.10-9.05 (1H, m), 9.02 (1H, d, J=8.5 Hz), 8.42 (1H, d, J=7.3 Hz), 8.39-8.31 (1H, m), 7.98 (1H, dd, J=8.4, 5.3 Hz), 7.89 (1H, t, J=7.9 Hz), 5.07 (1H, s), 4.45 (1H, t, J=3.0 Hz), 4.42-4.34 (1H, m), 4.16-4.05 (1H, m), 4.01 (1H, t, J=10.0 Hz), 3.91 (1H, t, J=10.1 Hz), 3.50 (1H, d, J=11.2 Hz), 3.21 (1H, d, J=10.3 Hz), 2.77 (6H, d, J=13.0 Hz), 2.01-1.91 (2H, m), 1.21 (3H, d, J=6.1 Hz). MS (ESI): m/z 489 (M⁺+H).

3'-Dihydro-3'-deoxy-4(R)-2-(1-benzyl-1H-1,2,3-triazol-4-yl)acetyl-amino spectinomycin tetrabromide (1537)

¹H NMR (D₂O, 400 MHz): δ 7.84 (1H, s), 7.34 (3H, ddd, J=8.1, 4.4, 1.5 Hz), 7.28-7.24 (2H, m), 5.53 (2H, s), 4.85 (1H, s), 4.66 (1H, t, J=2.5 Hz), 4.35-4.25 (1H, m), 4.05 (1H, t, J=3.1 Hz), 3.89 (3H, dt, J=24.4, 9.8 Hz), 3.55 (2H, q, J=7.1 Hz), 3.43 (1H, d, J=8.7 Hz), 3.20-3.13 (1H, m), 2.73 (6H, d, J=2.1 Hz), 1.82-1.73 (1H, m), 1.63 (1H, dd, J=12.3, 2.4 Hz), 1.13 (3H, d, J=6.1 Hz). MS (ESI): m/z 533 (M⁺+H).

3'-Dihydro-3'-deoxy-4(R)-(2-((4-fluorophenyl)amino)thiazol-4-yl)acetylamino spectinomycin tribromide (1538)

¹H NMR (D₂O, 400 MHz): δ 7.39-7.34 (2H, m), 7.20-7.14 (2H, m), 6.62 (1H, s), 4.87 (1H, s), 4.68-4.66 (1H, m), 4.30 (1H, dd, J=10.9, 9.9 Hz), 4.09 (1H, t, J=3.0 Hz), 3.91 (3H, m), 3.65 (1H, d, J=3.8 Hz), 3.55 (1H, q, J=7.1 Hz), 3.46-3.41 (1H, m), 3.18 (1H, dd, J=10.2, 2.7 Hz), 2.74 (s, 6H), 1.86-1.77 (1H, m), 1.66 (1H, d, J=14.6 Hz), 1.16 (3H, d, J=6.1 Hz). MS (ESI): m/z 568 (M⁺+H).

3'-Dihydro-3'-deoxy-4(R)-(2-((3-fluorophenyl)amino)thiazol-4-yl)acetylamino spectinomycin tribromide (1539)

¹H NMR (D₂O, 400 MHz): δ 7.40 (1H, td, J=8.2, 6.6 Hz), 7.22-7.13 (2H, m), 6.99 (1H, td, J=8.6, 2.4 Hz), 6.67 (1H, s), 4.88 (1H, s), 4.67 (1H, t, J=2.8 Hz), 4.35-4.21 (1H, m), 4.09 (1H, t, J=3.1 Hz), 4.01-3.83 (3H, m), 3.66 (1H, d, J=1.8 Hz), 3.58-3.53 (1H, m), 3.44 (1H, dd, J=7.7, 3.4 Hz), 3.18 (1H, dd, J=10.2, 2.7 Hz), 2.74 (6H, s), 1.86-1.76 (1H, m), 1.71-1.62 (1H, m), 1.14 (3H, d, J=6.1 Hz). MS (ESI): m/z 568 (M⁺+H).

3'-Dihydro-3'-deoxy-4(R)-(2-((4-(trifluoromethoxy)phenyl)amino)-thiazol-4-yl)acetylamino spectinomycin tribromide (1540)

¹H NMR (D₂O, 400 MHz): δ 7.45-7.41 (2H, m), 7.35 (2H, d, J=8.5 Hz), 6.65 (1H, s), 4.88 (1H, s), 4.67 (1H, t, J=2.8 Hz), 4.30 (1H, dd, J=10.9, 9.9 Hz), 4.09 (1H, t, J=3.1 Hz), 4.00-3.83 (3H, m), 3.66 (1H, d, J=2.6 Hz), 3.55 (1H, q, J=7.1 Hz), 3.44 (1H, dd, J=7.7, 3.4 Hz), 3.18 (1H, dd, J=10.2, 2.8 Hz), 2.74 (6H, s), 1.86-1.75 (1H, m), 1.71-1.63 (1H, m), 1.15 (3H, d, J=6.1 Hz). MS (ESI): m/z 634 (M⁺+H).

3'-Dihydro-3'-deoxy-4(R)-(2-((4-(trifluoromethyl)phenyl)amino)-thiazol-4-yl)acetylamino spectinomycin tribromide (1541)

¹H NMR (D₂O, 400 MHz): δ 7.71 (2H, d, J=8.5 Hz), 7.51 (2H, d, J=8.6 Hz), 6.71 (1H, s), 4.88 (1H, s), 4.68-4.66 (1H, m), 4.30 (1H, dd, J=11.0, 9.9 Hz), 4.09 (1H, t, J=3.0 Hz), 3.98-3.84 (3H, m), 3.67 (1H, s), 3.55 (1H, q, J=7.1 Hz), 3.43 (1H, m), 3.18 (1H, dd, J=10.2, 2.7 Hz), 2.74 (s, 6H), 1.86-1.75 (1H, m), 1.67 (1H, d, J=14.5 Hz), 1.14 (3H, d, J=6.1 Hz). MS (ESI): m/z 618 (M⁺+H).

3'-Dihydro-3'-deoxy-4(R)-(5-(4-fluorophenyl)pyridin-2-yl)acetylamino spectinomycin tribromide (1542)

¹H NMR (D₂O, 400 MHz): δ 8.90 (1H, d, J=2.2 Hz), 8.66 (1H, dd, J=8.4, 2.2 Hz), 7.91 (1H, d, J=8.4 Hz), 7.74-7.66 (2H, m), 7.29-7.21 (2H, m), 4.94 (1H, s), 4.69-4.67 (1H, m), 4.35-4.27 (1H, m), 4.16 (1H, d, J=4.6 Hz), 4.14-4.11 (1H, m), 4.07-3.85 (3H, m), 3.56 (1H, q, J=7.1 Hz), 3.49-3.42 (1H, m), 3.19 (1H, dd, J=10.2, 2.6 Hz), 2.75 (s, 6H), 1.90-1.77 (1H, m), 1.70 (1H, d, J=14.6 Hz), 1.19 (3H, d, J=6.1 Hz). MS (ESI): m/z 547 (M⁺+H).

3'-Dihydro-3'-deoxy-4(R)-(5-(3-methoxyphenyl)pyridin-2-yl)acetyl-amino spectinomycin tribromide (1543)

¹H NMR (D₂O, 400 MHz): ¹H NMR (400 MHz, D₂O) δ 8.90 (1H, s), 8.63 (1H, d, J=8.3 Hz), 7.87 (1H, d, J=8.5 Hz), 7.47 (1H, t, J=8.0 Hz), 7.29 (1H, d, J=7.6 Hz), 7.25 (1H, s), 7.10 (1H, d, J=8.3 Hz), 4.94 (1H, s), 4.31 (1H, t, J=10.4 Hz), 4.13 (2H, s), 4.06-3.87 (3H, m), 3.83 (s, 3H), 3.56 (1H, dd, J=14.2, 7.1 Hz), 3.44 (1H, d, J=3.9 Hz), 3.18 (1H, d, J=8.9 Hz), 2.74 (s, 6H), 1.87-1.81 (1H, m), 1.70 (1H, d, J=14.0 Hz), 1.19 (3H, d, J=6.0 Hz). MS (ESI): m/z 559 (M⁺+H).

3'-Dihydro-3'-deoxy-4(R)-(4-chloropyridin-2-yl)acetylamino spec-tinomycin tribromide (1544)

¹H NMR (D₂O, 400 MHz): ¹H NMR (400 MHz, D₂O) δ 8.57 (1H, dd, J=5.3, 1.8 Hz), 7.87-7.85 (2H, m), 4.93 (1H, s), 4.69-4.66 (1H, m), 4.34-4.28 (1H, m), 4.11 (1H, t, J=3.0 Hz), 4.09-3.83 (m, 5H), 3.45 (1H, dd, J=11.1, 2.6 Hz), 3.19 (1H, dd, J=10.2, 2.8 Hz), 2.74 (6H, d, J=0.9 Hz), 1.87-1.78 (1H, m), 1.69 (1H, d, J=14.5 Hz), 1.18 (3H, d, J=6.1 Hz). MS (ESI): m/z 487 (M⁺+H).

General Procedure for the Synthesis of 3'-deoxy 3'-alkylamino spectinomycins (1419, 1420 and 1421):

To a stirred suspension of NaBH₄ (10 mmol) and diCbz protected amide (1 mmol) in anhydrous dioxane (10 mL) was added CF₃COOH (10 mmol) in dioxane (2 mL) at room temperature. After the evolution of the gas had ceased, the mixture was heated to reflux for 2 h, cooled, poured into water (50 mL) and extracted with CH₂Cl₂ (2×30 mL), washed with water (30 mL), dried (Na₂SO₄), evaporated and the residue was purified by column chromatography. Deprotection of the amino protecting groups was achieved by dissolution of the protected amide in a mixture of 1.25 M HCl in MeOH and EtOH (1:1) with 10% Pd—C (50% by mass). The mixture was hydrogenated under 30 Psi/H₂ at room temperature for 2 hrs, filtered and concentrated. The resulting solid was titurated with cold diethyl ether, filtered and the resulting solid washed with excess ether and dried in vacuo to give the target 3'-deoxy 3'-alkylamino spectinomycins.

General Procedure for the Synthesis of 3'-deoxy 3'-alkylamino spectinomycins (1422-1425):

6,8-dibenzyloxycarbonyl 4(R)-amino spectinomycin (1 mmol) and corresponding aryl aldehyde (1.2 mmol) in anhydrous EtOH (10 mL) were stirred at room temperature for 5 h. PtO₂ (cat) was added and the mixture hydrogenated at 30 Psi/H₂ at room temperature for overnight, filtered, concentrated and purified by column chromatography. Deprotection of the amino CBz protecting groups was achieved by dissolution of the protected amide in a mixture of 1.25 M HCl in MeOH and EtOH (1:1) with 10% Pd—C (50% by mass). The mixture was hydrogenated under 30 Psi/H₂ at room temperature for 2 hrs, filtered and concentrated. The resulting solid was titurated with cold diethyl ether, filtered and the resulting solid washed with excess ether and dried in vacuo to give the target 3'-deoxy 3'-alkylamino spectinomycins.

Analytical Data for Individual 3'-Deoxy 3'-Alkylamino Spectinomycin Compounds:

3'-Dihydro-3'-deoxy-4(R)-cyclopropylmethylamino spectinomycin Trihydrochloride (1419)

¹H NMR (CD₃OD, 500 MHz): δ 5.01 (1H, s), 4.33 (1H, t, J=10.2 Hz), 3.99 (1H, t, J=9.5 Hz), 3.88 (1H, t, J=10.0 Hz), 3.62-3.67 (3H, m), 3.42-3.53 (1H, m), 3.05-3.11 (3H, m), 2.81 (3H, s), 2.78 (3H, s), 1.99-2.08 (1H, m), 1.62-1.82 (1H, m), 1.28 (3H, d, J=5.6 Hz), 1.14-1.19 (1H, m), 0.72 (2H, d, J=5.3 Hz), 0.43 (2H, d, J=16.6 Hz); MS (ESI): m/z 388 (M⁺+H).

3'-Dihydro-3'-deoxy-4(R)-(3-methyl)butylamino spectinomycin Trihydrochloride (1420)

¹H NMR (CD₃OD, 500 MHz): δ5.04 (1H, s), 4.39 (1H, t, J=10.5 Hz), 3.84-4.00 (3H, m), 3.67-3.77 (2H, m), 3.06-3.23

(4H, m), 2.89 (3H, s), 2.85 (3H, s), 2.12-2.22 (2H, m), 1.62-1.74 (3H, m), 1.34 (3H, d, J=5.8 Hz), 1.01 (6H, br s); $^{13}$CNMR (CD$_3$OD, 125 MHz): δ 93.2, 88.9, 75.5, 70.2, 69.0, 66.5, 66.2, 61.7, 61.5, 60.0, 58.4, 37.5, 34.1, 30.5, MS (ESI): m/z 404 (M$^+$+H).

3'-Dihydro-3'-deoxy-4(R)-dodecylamino spectinomycin Trihydrochloride (1421)

$^1$H NMR (D$_2$O, 500 MHz): δ 5.03 (1H, s), 4.28-4.37 (1H, m), 4.03 (2H, t, J=9.7 Hz), 3.96 (1H, t, J=10.0 Hz), 3.75 (1H, t, J=10.0 Hz), 3.53 (1H, d, J=8.5 Hz), 3.84-3.42 (1H, m), 3.09-3.26 (3H, m), 3.02 (1H, d, J=15.6 Hz), 2.81 (8H, s), 1.98-2.10 (1H, m), 1.67-1.72 (1H, m), 1.28 (20H, br s), 0.82 (3H, d, J=6.5 Hz); $^{13}$C NMR (CD$_3$OD, 125 MHz): δ 94.8, 90.4, 71.9, 70.3, 67.6, 63.2, 61.0, 33.2, 30.8, 27.8, 23.8, 21.1; MS (ESI): m/z 502 (M$^+$+H).

3'-Dihydro-3'-deoxy-4(R)-furan-2-yl-methylamino spectinomycin Trihydrochloride (1422)

$^1$H NMR (D$_2$O, 500 MHz): δ 7.61 (1H, s), 6.68 (1H, d, J=2.4 Hz), 6.51 (1H, s), 5.04 (1H, s), 4.47 (1H, s), 4.28-4.36 (3H, m), 4.01-4.09 (2H, m), 3.90-3.97 (1H, m), 3.81-3.90 (1H, m), 3.46-3.54 (1H, m), 3.24-3.26 (1H, m), 2.81 (6H, s), 1.89-2.17 (2H, m), 1.28 (3H, d, J=5.6 Hz); MS (ESI): m/z 414 (M$^+$+H).

3'-Dihydro-3'-deoxy-4(R)-(3-methoxy)benzylamino spectinomycin Trihydrochloride (1423)

$^1$H NMR (D$_2$O, 500 MHz): δ 7.44 (1H, t, J=8.5 Hz), 7.11 (3H, d, J=7.8 Hz), 5.02 (1H, s), 4.26-4.54 (3H, m), 3.92-4.06 (3H, m), 3.84 (3H, s), 3.40-3.54 (2H, m), 3.20-3.26 (2H, m), 2.80 (6H, s), 2.06 (1H, d, J=15.6 Hz), 1.92-1.98 (1H, m), 1.28 (3H, d, J=5.8 Hz); MS (ESI): m/z 454 (M$^+$+H).

3'-Dihydro-3'-deoxy-4(R)-4-fluoro)benzylamino spectinomycin Trihydrochloride (1424)

$^1$H NMR (D$_2$O, 500 MHz): δ 7.52 (2H, t, J=7.5 Hz), 7.22 (2H, t, J=8.5 Hz), 5.02 (1H, s), 4.41 (2H, dd, J=13.4 Hz), 4.29 (1H, t, J=10.5 Hz), 4.00-4.09 (3H, m), 3.95 (1H, t, J=10.0 Hz), 3.49 (2H, t, J=14.4 Hz), 3.24 (1H, d, J=10.2 Hz), 2.80 (3H, s), 2.78 (3H, s), 2.09 (1H, d, J=15.8 Hz), 1.95-2.00 (1H, m), 1.27 (3H, d, J=5.8 Hz); MS (ESI): m/z 442 (M$^+$+H).

3'-Dihydro-3'-deoxy-4(R)-(4-methyl)benzylamino spectinomycin Trihydrochloride (1425)

$^1$H NMR (D$_2$O, 500 MHz): δ 7.35 (4H, dd, J=7.5 Hz), 5.01 (1H, s), 4.38 (2H, dd, J=13.1 Hz), 4.28 (1H, t, J=10.5 Hz), 4.00-4.09 (3H, m), 3.94 (1H, t, J=10.0 Hz), 3.50 (1H, d, J=10.9 Hz), 3.42 (1H, br s), 3.25 (1H, d, J=10.0 Hz), 2.80 (3H, s), 2.77 (3H, s), 2.35 (3H, s), 2.06 (1H, d, J=15.8 Hz), 1.95 (1H, t, J=11.7 Hz), 1.27 (3H, d, J=5.8 Hz); MS (ESI): m/z 438 (M$^+$+H).

3'-Dihydro-3'-deoxy-4(R)-2-phenylethylamino spectinomycin Trihydrochloride (1450)

$^1$H NMR (D$_2$O, 400 MHz): δ 7.32-7.42 (3H, m), 7.22-7.29 (2H, m), 5.01 (1H, s), 4.38 (2H, dd, J=13.1 Hz), 4.28 (1H, t, J=10.5 Hz), 4.00-4.09 (3H, m), 3.94 (1H, t, J=10.0 Hz), 3.50 (1H, d, J=10.9 Hz), 3.42 (1H, br s), 3.25 (1H, d, J=10.0 Hz), 2.62 (2H, m), 2.77 (3H, s), 2.35 (3H, s), 2.06 (1H, d, J=15.8 Hz), 1.95 (1H, t, J=11.7 Hz), 1.27 (3H, d, J=5.8 Hz); MS (ESI): m/z 438 (M$^+$+H).

Example 2

General In Vitro and In Vivo Methods

MIC Determination:

MICs were determined using the microbroth dilution method according to Clinical Laboratory Standards Institute (CLSI; National, C. F. C. L. S., *Methods for Dilution Antimicrobial Susceptibility Tests for Bacteria that Grow Aerobically-Seventh Edition: Approved Standard M7-A7*, CLSI, Wayne, Pa., United States of America, 2008) and were read by visual inspection. Two-fold serial dilutions of antibiotic in 100 μL of the appropriate broth media were first prepared in 96-well round bottom microtiter plates (Nalge Nunc International, Rochester, N.Y., United States of America). An equivalent volume (100 μL) of bacterial broth inocula containing approximately 10$^5$ bacterial cfu/mL was added to each well to give final concentrations of drug starting at 200 μg/mL and the plates were incubated aerobically at 37° C. *M. tuberculosis* and *M. bovis* BCG microtiter plates were incubated for 7 days and all other strains were incubated overnight. MICs against *M. tuberculosis* were also evaluated by a method based on the agar proportion approach by CLSI. Briefly, 24 well plates were prepared with 2-fold serial dilutions of antibiotic in 2 mL of 7H11 agar and were inoculated with ca. 10$^5$ cfu and incubated for 3 weeks. After incubations, in all cases the MIC was recorded as the lowest concentration of drug that prevented bacterial growth.

Chequerboard Synergy Assay:

The activity of 1329 in combination with rifampicin, isoniazid and ethambutol were evaluated in triplicate against *M. tuberculosis* H37Rv by the chequerboard titration method in 96-well round bottom plates. Similar combinations with streptomycin were evaluated for comparison. Plates contained bacterial inocula (10$^5$ cfu/mL) and 2-fold serial dilutions of each antibiotic in total volumes of 200 μL of broth. The maximum and minimum concentrations of each diluted drug were at least ±4-fold their MIC. Following 7 days of incubation at 37° C., MICs of drug combinations were read by visual inspection and fractional inhibitory concentration (FIC) indices against *M. tuberculosis* H37Rv were calculated as described by Eliopoulos et al. See Eliopoulos et al., Antimicrobial Combinations, in *In Antibiotics in Laboratory Medicine*, Williams and Wilkins, Co., Baltimore, Md., United States of America, 2000, pp 432-449. FIC indices were interpreted as follows: ≤0.5, synergy; >0.5 to 4, additive; and >4, antagonism. See Odds, F. C., *J. Antimicrob. Chemother.*, 52, 1 (2003).

Selection and Phenotypic Characterization of Resistant Mutants:

Spontaneous mutation frequencies were determined against *M. tuberculosis* H37Rv by plating 100 μl of a saturated culture onto 7H11 agar plates containing drug at 4, 8 and 16× the agar MIC. Plates were incubated for 3 weeks at 37° C. and the mutation frequency was recorded as the number of resistant colonies divided by the total viable cells. Isolated colonies were then picked at random from the selection plates and inoculated into 7H9 broth containing the concentration of antibiotic on which they were selected. Colonies able to re-grow were then grown to mid-log phase in the absence of drug and antibiotic MICs determined by broth microdilution.

Detection of Spectinomycin Resistance Mutations:

To determine the genetic mechanism of resistance to spectinomycin in *M. tuberculosis*, genes for 16S rRNA and rpsE were PCR amplified using the respective oligonucleotide primers from Integrated DNA Technologies (Coralville, Iowa, United States of America). The 16S rRNA was amplified using 16S-F (5'-CCG 111 GTT TTG TCA GGA TA) (SEQ ID NO: 1) and 16S-R (TIC TCA AAC ACC ACA CCC CA) (SEQ ID NO: 2) and rpsE was amplified with rpsE-F (5'-GGC GTG CCG GGT GAC AAA AAG G) (SEQ ID NO: 3) and rpsE-R (5'-GAA TCC TTC GTA AGC CCA) (SEQ ID NO: 4) under touchdown PCR cycling conditions. Amplicons were purified using Qiagen's MINELUTE™ PCR Kit (Qiagen, N.V., Venlo, the Netherlands) and sequenced by the Molecular Resource Center, University of Tennessee Health Science Center (Memphis, Tenn., United States of America), using an ABI Model 3130XL Genetic Analyzer (Applied Biosystems, Foster City, Calif., United States of America). Sequence chromatograms were next analyzed using the software program CLC Main Workbench (CLC bio, Aarhus, Denmark).

Cytotoxicity:

Vero epithelial cells (from African green monkey; American Type Culture Collection (ATCC)CCL-81; Manassas, Va., United States of America) were cultured in Dulbecco's Modified Eagle's Medium (DMEM) supplemented with 10% fetal bovine serum (FBS) and maintained in a humidified incubator (37° C., 5% $CO_2$). Cells were dislodged with a cell scraper, collected by centrifugation, resuspended in fresh medium at ~$10^6$ cells/mL, dispensed into 96-well microtiter plates (100 μL/well) and incubated for 18 hours at 37° C. Two-fold serial dilutions of test compounds (800-0.4 mg/L) in DMEM with FBS were subsequently added and cells incubated for another 72 hours. From triplicate studies the cytopathic effects of compounds were evaluated colorimetrically using the MTT Cell Proliferation Assay (ATCC, Manassas, Va., United States of America). $IC_{50}$ data were obtained from dose response curves plotted using GraphPad prism 5 (GraphPad Software, San Diego, Calif., United States of America).

*E. coli* S30 Transcription/Translation Assay:

The commercially available *E. coli* S30 assay (Promega, Madison, Wis., United States of America) monitors luciferase production and was performed as described by the manufacturer. Reactions were performed in 25 μL volumes consisting of 10 □L of Premix, 2.5 μL complex amino acids, 7.5 μL of S30 extract, 2.5 μL of inhibitor or DMSO (2.5%), 1 μL of pBESTluc plasmid (1 μg) and 1.5 μL of nuclease-free water. Reactions were incubated for 30 mins before being stopped by placing on ice for five mins. Subsequently, 50 μL of Luciferase Assay Reagent (Promega, Madison, Wis., United States of America) was added and luminescence readings obtained in a BioTek SYNERGY™ HT plate reader (BioTek Instruments, Inc., Winooski, Vt., United States of America). $IC_{50}$ data were obtained from dose response curves plotted using GraphPad prism 5 (GraphPad Software, San Diego, Calif., United States of America). Using the determined micromolar $IC_{50}$ value for compound 1329, other spectinomycin derivatives were examined.

In Vitro Microsomal Metabolic Stability:

In vitro microsomal metabolic stability of the compounds was assessed using pooled rat liver microsomal preparations (Cellzdirect, Austin, Tex., United States of America). Reactions were started by adding 25 μL of microsomal protein solution (10 mg/mL) to 25 μL of test compound (20 μM) and 200 μL of NADPH regenerating solution (1.3 mM NADP+, 3.3 mM glucose-6-phosphate, 3.3 mM $MgCl_2$ and 1 unit/mL glucose-6-phosphate dehydrogenase in pH 7.4 phosphate buffer solution). The reaction mixture was incubated at 37° C. and samples were taken at 0, 5, 10, 15, 30, 45, 60 and 90 minutes respectively. A reaction mixture containing above mentioned composition but instead using deactivated microsomes was used for control. All the samples were analyzed using LC-MS/MS assay. Disappearance of the parent compound was monitored during the incubation period. The percentage of parent compound remaining intact was estimated by comparing analyte concentrations before and after incubation.

Protein Binding:

Protein binding of the compounds was determined using equilibrium dialysis. Biologically relevant concentrations of test compound were prepared (low and high) in rat plasma. 200 μL of the plasma sample was placed in the central chamber and 350 μL of blank isotonic phosphate buffer, pH 7.4 was added to the peripheral chamber of a dialysis device (MW cutoff 6000-8000 D, RED® device, Pierce Biotechnology Inc, Rockford, Ill., United States of America). The chambers were covered with a seal and incubated at 37° C. for four hours on a shaker set at 100 rpm. At the end of incubation, the volumes of plasma and recipient buffer were measured to identify and account for volume shift, if any. Aliquots of plasma and buffer were used to determine the drug concentration using an LC-MS/MS assay. The free fraction of the drug was calculated as ratio of the concentrations in the buffer and in plasma.

Pharmacokinetic Studies:

Catheterized male Sprague-Dawley rats (jugular vein alone for oral study and jugular vein and femoral vein for intravenous study) weighing approximately 225 g were obtained from Harlan Bioscience (Indianapolis, Ind., United States of America). The animals were kept on a 12 hr light/dark cycle with food and water available ad libitum. Groups of rats (n=4) received either an intravenous (IV) or oral dose of a test compound at a dose level of 10 mg/kg or 100 mg/kg, respectively. For oral administration, the animals were fasted overnight and until 4 hr after administration of test compound. Serial blood samples (approx. 250 μL) were collected pre-dose and at predetermined time points post-dose until 48 hours. Plasma was separated immediately by centrifugation (10,000 rpm for 10 min at 4° C.) and stored at −80° C. until analysis. Urine specimens were collected for a period of 48 hours following drug administration. The study protocol was approved by the institutional animal care and use committee of the University of Tennessee Health Science Center (Memphis, Tenn., United States of America).

Sample Preparation and LC-MS/MS Assay:

A calibration curve ranging from 7.81-1000 μg/L was constructed for each test compound by spiking the test compound into 50 μL of blank rat plasma. A structurally similar analogue to the test compounds, compound 1369, was used as internal standard (IS) to all calibration standards and all plasma specimens. Plasma proteins were precipitated by the addition of four volumes of ice cold methanol containing IS. These samples were vortexed and kept on ice for 20 minutes. Following this, the samples were centrifuged at 10,000 rpm for 10 minutes at 4° C. and the supernatants were diluted if necessary and injected onto LC-MS/MS for analysis. Chromatographic separations were carried out using a Shimadzu liquid chromatograph (Shimadzu Corporation, Kyoto, Japan) consisting of two pumps, online degasser, system controller and a CTC Leap auto sampler (Leap Technologies, Carrboro, N.C., United States of America). A gradient of methanol and 10 mM ammonium acetate at pH 3.5 was used at a flow rate of 0.4 mL/min. A Phenomenex® Luna 3μ HILIC, 100×4.6 mm column (Phenomenex, Torrance, Calif., United States of America) protected with a guard column was used for the separation. 10 μL of sample was injected onto the column and the eluate was led directly into an API 3000 triple-quadrupole mass spectrometer (Applied Biosystems ABI/MDS-Sciex, Foster City, Calif., United States of America) equipped with an electrospray ion source. The instrument was operated in the positive ion mode with nebulizer gas (NEB) at 7 psi, curtain gas (CUR) at 8 psi, collision gas (CAD) at 10 psi, ion spray voltage (IS) at +4000 V and temperature (TEM) at 500° C. The resulting multiple reaction monitoring chromatograms were used for quantification using Analyst software version 1.4.1 (Applied Biosystems ABI/MDS-Sciex, Foster City, Calif., United States of America).

Pharmacokinetic Data Analysis:

Plasma concentration-time data for oral dose were analyzed by non-compartmental analysis. A two compartment open model with bolus input and first order output was used to analyze the IV plasma concentration-time data. The area under the plasma concentration-time curve from time 0 to infinity (AUCinf) was calculated by the trapezoidal rule with extrapolation to time infinity. Mean residence time (MRT), the average amount of time a particle remains in a compartment of system was calculated for IV dose using MRT=AUMCinf/AUCinf where AUMCinf is the area under the moment curve when the concentration-time curve is extrapolated to infinity. The systemic clearance (CL) was calculated using the equation CL=Doseiv/AUCinf iv, where Doseiv and AUCinf, iv are the IV dose and corresponding area under the plasma concentration-time curve from time 0 to infinity, respectively. An estimate of volume of distribution at steady state (Vss) was obtained from IV data using Vss=MRT*CL. Oral bioavailability (F) was calculated using F=(AUCinf, oral* Doseiv)/(AUCinf, iv *Doseoral), where Doseoral, Doseiv, AUCinf, iv, and AUCinf, oral are the oral and IV doses and the corresponding areas under the plasma concentration-time curves from time 0 to infinity, respectively. Physiologic parameters for rats obtained from Davies et al. (*Pharm. Res.*, 10(7), 1093-1095 (1993)) were used to calculate the excretion ratio and hepatic extraction ratio.

Example 3

Anti-Tuberculosis Activity

The anti-tuberculosis activity of the spectinomycin analogs was determined against *M. tuberculosis* H37Rv in Middlebrook 7H9 supplemented with 10% ADC media by microbroth dilution of drug in 96 well plates. The plates were incubated at 37° C. for 7 days and then read visually for growth inhibition according to previously described methods. See, e.g., Hurdle et al., *J. Antimicrob. Chemother*, 62(5), 1037-1045 (2008). Results are shown in Tables 1 and 2.

TABLE 1

Anti-tubercular Activity of the 3'-Deoxy 3'(R)-Acylamino Spectinomycins.

| Comp. No | Structure | MIC (μg/mL) |
|---|---|---|
| 1299 | | 25 |
| 1329 | 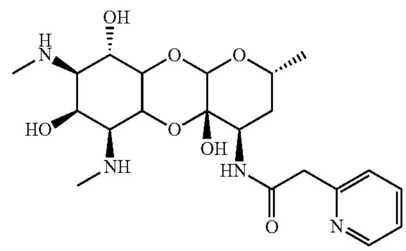 [SMILES: CN[C@@H]1[C@H](O)[C@H](NC)C2O[C@]3(O)C(OC2[C@H]1O)O[C@H](C)C[C@H]3NC(=O)Cc1ccccn1] | 0.8 |
| 1351 | 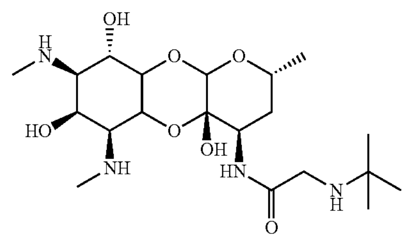 [SMILES: CN[C@@H]1[C@H](O)[C@H](NC)C2O[C@]3(O)C(OC2[C@H]1O)O[C@H](C)C[C@H]3NC(=O)CNC(C)(C)C] | 25 |
| 1364 | 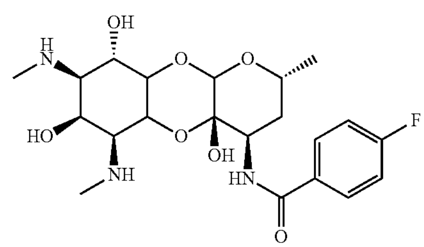 [SMILES: CN[C@@H]1[C@H](O)[C@H](NC)C2O[C@]3(O)C(OC2[C@H]1O)O[C@H](C)C[C@H]3NC(=O)c1ccc(F)cc1] | 50 |
| 1365 | 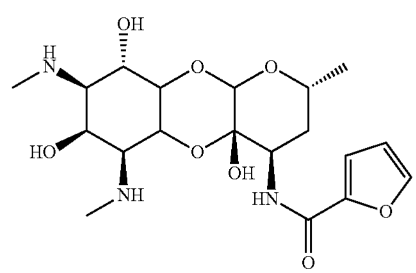 [SMILES: CN[C@@H]1[C@H](O)[C@H](NC)C2O[C@]3(O)C(OC2[C@H]1O)O[C@H](C)C[C@H]3NC(=O)c1ccco1] | 100 |
| 1366 | 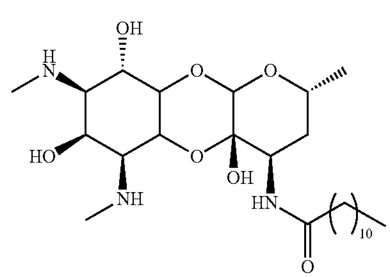 | 1.6 |

TABLE 1-continued
Anti-tubercular Activity of the 3'-Deoxy 3'(R)-Acylamino Spectinomycins.
| Comp. No | Structure | MIC (μg/mL) |
|---|---|---|
| 1367 | 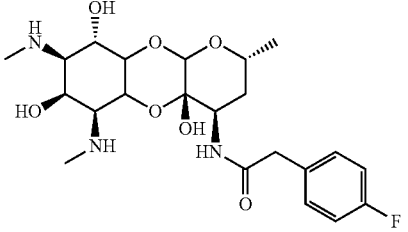 [SMILES: CN[C@@H]1[C@H](O)[C@H](NC)C2O[C@]3(O)C(OC2[C@H]1O)O[C@H](C)C[C@H]3NC(=O)Cc1ccc(F)cc1] | 3.1 |
| 1368 | 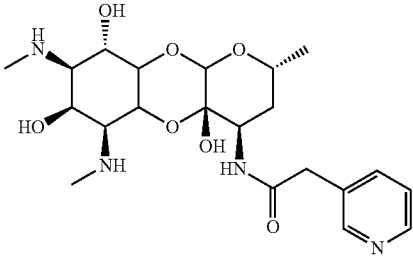 [SMILES: CN[C@@H]1[C@H](O)[C@H](NC)C2O[C@]3(O)C(OC2[C@H]1O)O[C@H](C)C[C@H]3NC(=O)Cc1cccnc1] | 12.5 |
| 1369 | 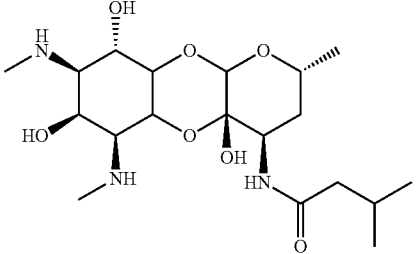 [SMILES: CN[C@@H]1[C@H](O)[C@H](NC)C2O[C@]3(O)C(OC2[C@H]1O)O[C@H](C)C[C@H]3NC(=O)CC(C)C] | 200 |
| 1370 | 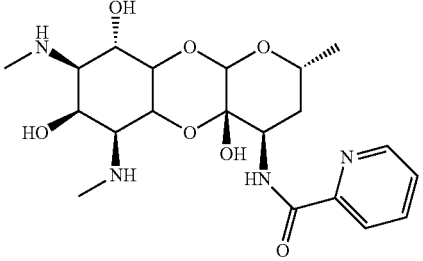 [SMILES: CN[C@@H]1[C@H](O)[C@H](NC)C2O[C@]3(O)C(OC2[C@H]1O)O[C@H](C)C[C@H]3NC(=O)c1ccccn1] | 100 |
| 1398 | 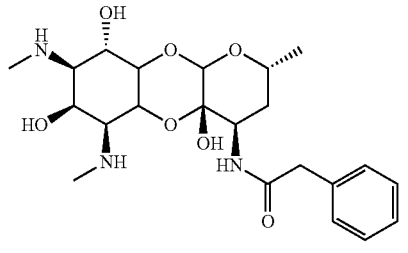 [SMILES: CN[C@@H]1[C@H](O)[C@H](NC)C2O[C@]3(O)C(OC2[C@H]1O)O[C@H](C)C[C@H]3NC(=O)Cc1ccccc1] | 6.1 |
| 1399 | 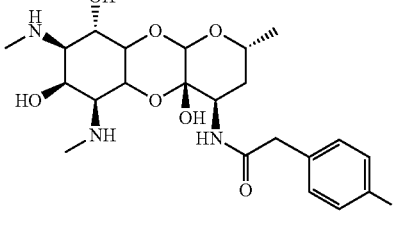 | 6.1 |
| 1400 | 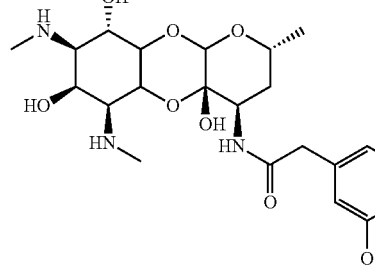 | 12.5 |
| 1411 | 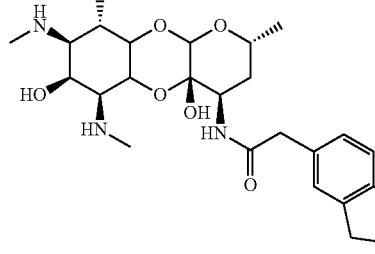 | 25 |
| 1412 | 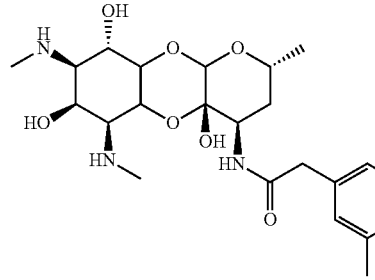 | 25 |
| 1413 | 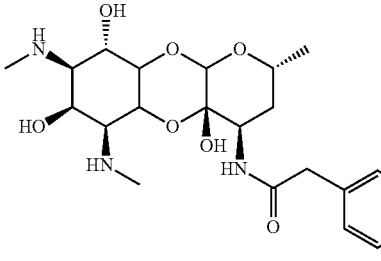 | 100 |

TABLE 1-continued

Anti-tubercular Activity of the 3'-Deoxy 3'(R)-Acylamino Spectinomycins.

| Comp. No | Structure | MIC (μg/mL) |
|---|---|---|
| 1439 | 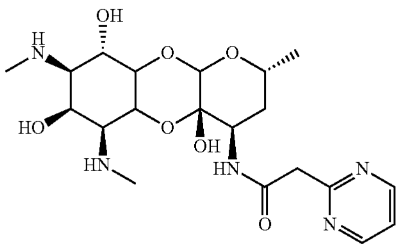 [SMILES: CN[C@@H]1[C@H](O)[C@H](NC)C2O[C@]3(O)C(OC2[C@H]1O)O[C@H](C)C[C@H]3NC(=O)Cc1ncccn1] | >200 |
| 1443 | 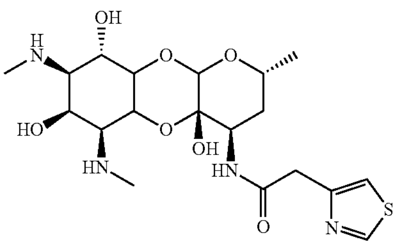 [SMILES: CN[C@@H]1[C@H](O)[C@H](NC)C2O[C@]3(O)C(OC2[C@H]1O)O[C@H](C)C[C@H]3NC(=O)Cc1cscn1] | 1.6 |
| 1444 | 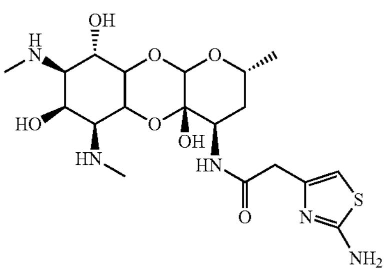 [SMILES: CN[C@@H]1[C@H](O)[C@H](NC)C2O[C@]3(O)C(OC2[C@H]1O)O[C@H](C)C[C@H]3NC(=O)Cc1csc(N)n1] | 3.1 |
| 1445 | 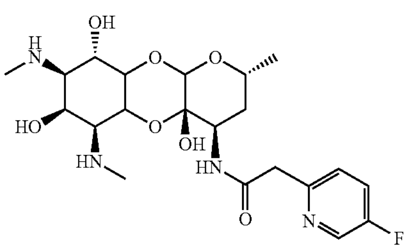 [SMILES: CN[C@@H]1[C@H](O)[C@H](NC)C2O[C@]3(O)C(OC2[C@H]1O)O[C@H](C)C[C@H]3NC(=O)Cc1ccc(F)cn1] | 0.4 |
| 1446 | 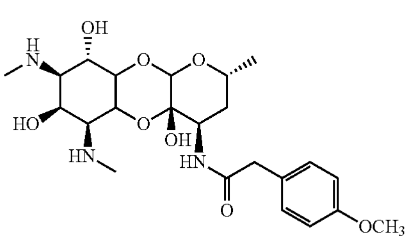 [SMILES: CN[C@@H]1[C@H](O)[C@H](NC)C2O[C@]3(O)C(OC2[C@H]1O)O[C@H](C)C[C@H]3NC(=O)Cc1ccc(OC)cc1] | 12.5 |
| 1447 | 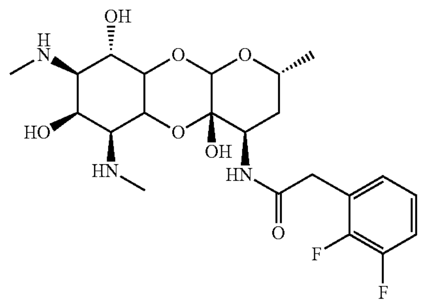 [SMILES: CN[C@@H]1[C@H](O)[C@H](NC)C2O[C@]3(O)C(OC2[C@H]1O)O[C@H](C)C[C@H]3NC(=O)Cc1cccc(F)c1F] | 50 |
| 1448 | 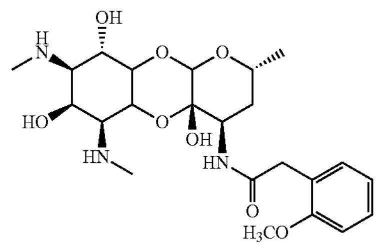 [SMILES: CN[C@@H]1[C@H](O)[C@H](NC)C2O[C@]3(O)C(OC2[C@H]1O)O[C@H](C)C[C@H]3NC(=O)Cc1ccccc1OC] | 200 |
| 1449 | 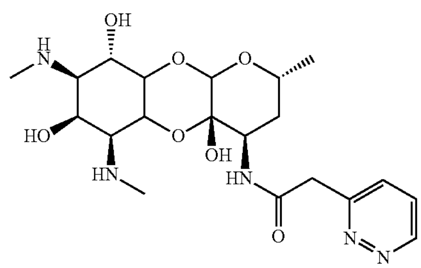 [SMILES: CN[C@@H]1[C@H](O)[C@H](NC)C2O[C@]3(O)C(OC2[C@H]1O)O[C@H](C)C[C@H]3NC(=O)Cc1cccnn1] | 25 |
| 1453 | 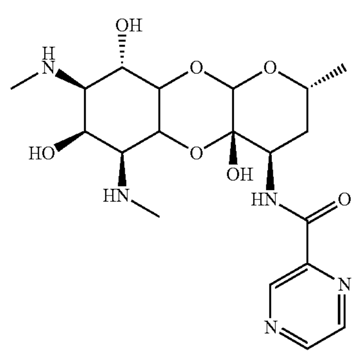 [SMILES: CN[C@@H]1[C@H](O)[C@H](NC)C2O[C@]3(O)C(OC2[C@H]1O)O[C@H](C)C[C@H]3NC(=O)c1cnccn1] | >200 |

TABLE 1-continued

Anti-tubercular Activity of the 3'-Deoxy 3'(R)-Acylamino Spectinomycins.

| Comp. No | Structure | MIC (µg/mL) |
|---|---|---|
| 1465 | 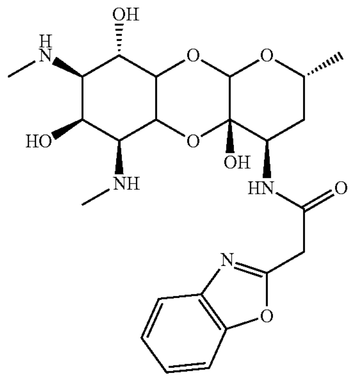 | 3.12 |
| 1466 | 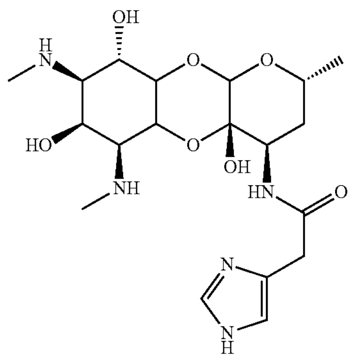 [SMILES: CN[C@@H]1[C@H](O)[C@H](NC)C2O[C@]3(O)C(OC2[C@H]1O)O[C@H](C)C[C@H]3NC(=O)Cc1c[nH]cn1] | 6.25 |
| 1467 | 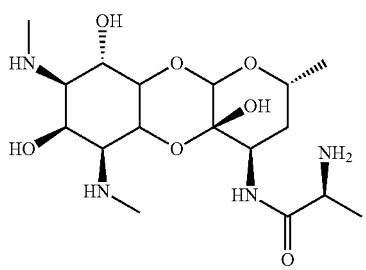 | 200 |
| 1469 | 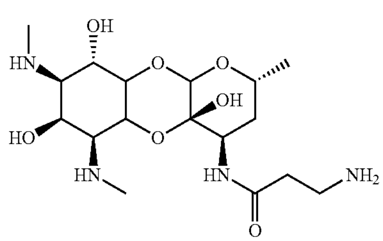 | 200 |
| 1470 | 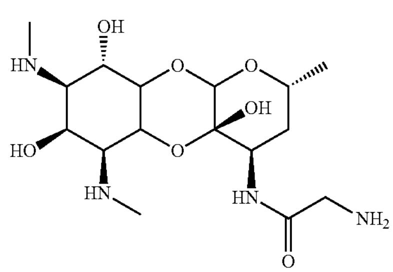 | 200 |
| 1485 | | 200 |
| 1486 | | 200 |
| 1487 | | 200 |
| 1489 | | 6.25 |
| 1490 | | 6.25 |

TABLE 1-continued

Anti-tubercular Activity of the 3'-Deoxy 3'(R)-Acylamino Spectinomycins.

| Comp. No | Structure | MIC (µg/mL) |
|---|---|---|
| 1491 | 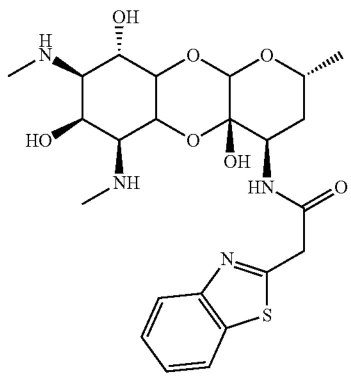 | 1.6 |
| 1492 | 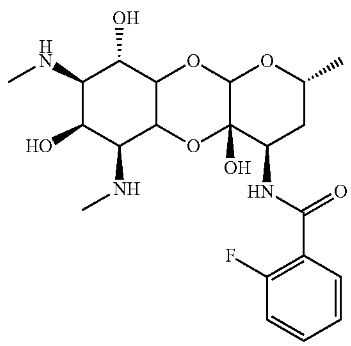 | >200 |
| 1493 | 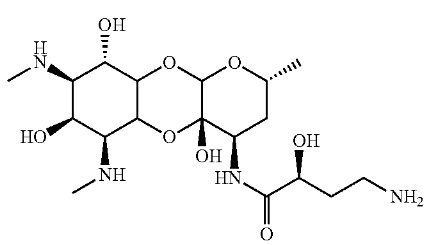 [SMILES: CN[C@@H]1[C@H](O)[C@H](NC)C2O[C@]3(O)C(OC2[C@H]1O)O[C@H](C)C[C@H]3NC(=O)[C@@H](O)CCN] | >200 |
| 1501 | 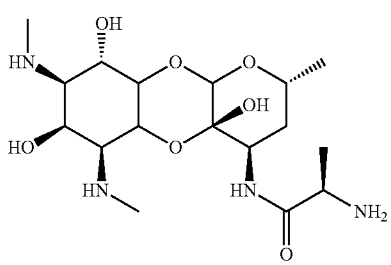 | >200 |
| 1502 | 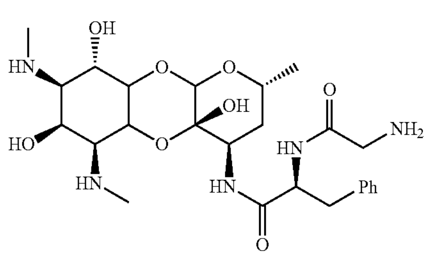 | >200 |
| 1503 | 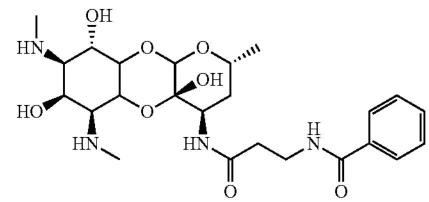 | >200 |
| 1504 | 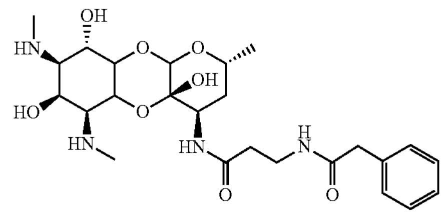 | >200 |
| 1514 | 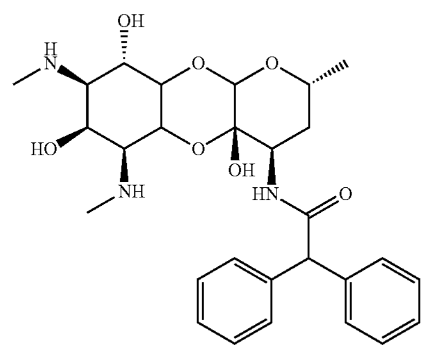 [SMILES: CN[C@@H]1[C@H](O)[C@H](NC)C2O[C@]3(O)C(OC2[C@H]1O)O[C@H](C)C[C@H]3NC(=O)C(c1ccccc1)c1ccccc1] | >200 |
| 1515 | 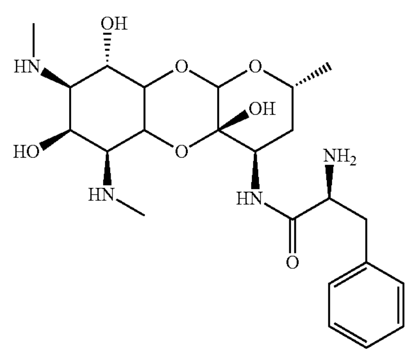 | 200 |
| 1516 | 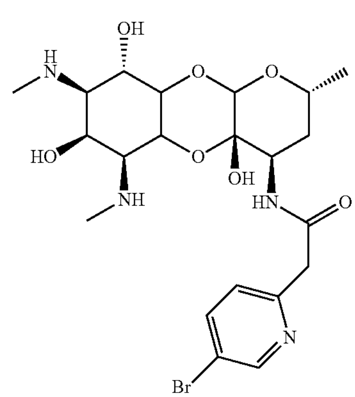 | 1.56 |

TABLE 1-continued

Anti-tubercular Activity of the 3'-Deoxy 3'(R)-Acylamino Spectinomycins.

| Comp. No | Structure | MIC (μg/mL) |
|---|---|---|
| 1517 | 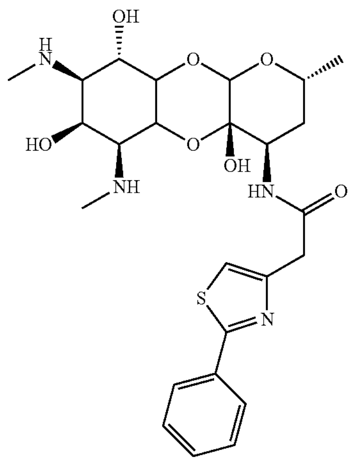 | 50 |
| 1518 | 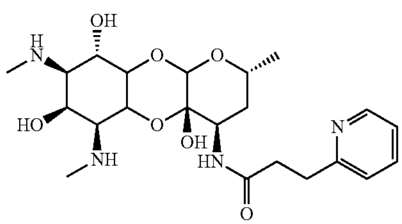 [SMILES: CN[C@@H]1[C@H](O)[C@H](NC)C2O[C@]3(O)C(OC2[C@H]1O)O[C@H](C)C[C@H]3NC(=O)CCc1ccccn1] | 50 |
| 1519 | 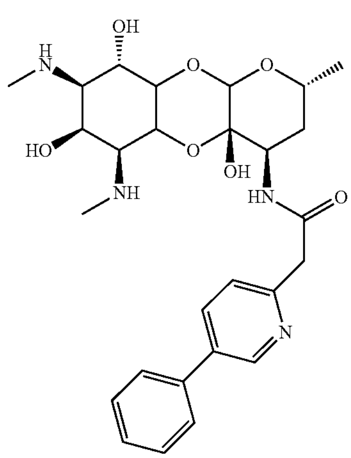 | 3.12 |
| 1520 | | 6.25 |
| 1535 | | 3.12 |
| 1536 | | >200 |

TABLE 1-continued

Anti-tubercular Activity of the 3'-Deoxy 3'(R)-Acylamino Spectinomycins.

| Comp. No | Structure | MIC (μg/mL) |
|---|---|---|
| 1537 | (spectinomycin core with acylamino-CH2-triazole-N-benzyl) | 50 |
| 1538 | (spectinomycin core with acylamino-CH2-thiazole-2-NH-(4-fluorophenyl)) | 6.25 |
| 1539 | (spectinomycin core with acylamino-CH2-thiazole-2-NH-(3-fluorophenyl)) | 6.25 |
| 1540 | (spectinomycin core with acylamino-CH2-thiazole-2-NH-(4-OCF3-phenyl)) | 6.25 |
| 1541 | (spectinomycin core with acylamino-CH2-thiazole-2-NH-(4-CF3-phenyl)) | 6.25 |
| 1542 | (spectinomycin core with acylamino-CH2-pyridine-5-(4-fluorophenyl)) | 3.12 |

TABLE 1-continued

Anti-tubercular Activity of the 3'-Deoxy 3'(R)-Acylamino Spectinomycins.

| Comp. No | Structure | MIC (µg/mL) |
|---|---|---|
| 1543 | [structure: spectinomycin core with HN-C(O)-CH2-pyridine-phenyl-OMe substituent] | 6.25 |
| 1544 | [structure: spectinomycin core with HN-C(O)-CH2-(4-chloropyridin-2-yl) substituent] | 0.8 |
| Spectinomycin | | 25 |

TABLE 2

Anti-tubercular Activity of the 3'-Deoxy 3'(R)-Alkylamino Spectinomycins.

| Comp. No | Structure | MIC (µg/mL) |
|---|---|---|
| 1419 | [structure: spectinomycin core with HN-CH2-cyclopropyl substituent] | 50 |
| 1420 | [structure: spectinomycin core with HN-CH2CH2-isopropyl (isopentyl) substituent] | 200 |
| 1421 | [structure: spectinomycin core with HN-(CH2)11-CH3 substituent] | 25 |
| 1422 | [structure: spectinomycin core with HN-CH2-furan-2-yl substituent] | 200 |
| 1423 | [structure: spectinomycin core with HN-CH2-(3-methoxyphenyl) substituent] | 200 |

TABLE 2-continued

Anti-tubercular Activity of the 3'-Deoxy 3'(R)-Alkylamino Spectinomycins.

| Comp. No | Structure | MIC (µg/mL) |
|---|---|---|
| 1424 | (structure) | 200 |
| 1425 | (structure) | 1000 |
| 1450 | (structure) | 200 |

Several compounds showed good anti-tubercular MIC values, with many having superior anti-tuberculosis activity compared to spectinomycin. The structure-activity relationship of this series with respect to structural changes and MIC values was very tight. Without being bound to any one theory, this is believed to be indicative of specific binding to a receptor site on the ribosome and strict rules for uptake of the inhibitors into the tuberculosis bacilli.

Example 4

Antibacterial Activity

The MICs of synthesized analogs of spectinomycin were determined against several other clinically important gram-positive and -negative pathogens, including *Staphylococcus aureus*, *Enterococcus faecalis*, *Bacillus anthracis*, *Streptococcus pyogenes*, *Streptococcus pneumoniae*, *Escherichia coli*, *Pseudomonas aeruginosa*, *Burkholderia cepacia*, *Proteus mirabilis*, *Proteus vulgaris*, *Klebsiella pneumoniae*, *Acinetobacter baumannii* and *Strenotrophomonas maltophillia*. These results are shown in Tables 3 and 4.

TABLE 3

Activity Against Gram-positive Bacteria.*

| | MIC µg/mL | | | | |
|---|---|---|---|---|---|
| Comp # | S. aureus | S. pyogenes | S. pneumoniae | E. faecalis | B. anthracis 34F2 |
| 1299 | 200 | 200 | 200 | >200 | 200 |
| 1329 | 50 | 50 | 6.25 | 100 | 50 |
| 1351 | 200 | 100 | 200 | >200 | 50 |
| 1364 | >200 | 100 | >200 | >200 | 200 |
| 1365 | >200 | >200 | >200 | >200 | >200 |
| 1366 | 25 | >200 | 25 | 25 | >200 |
| 1367 | 50 | 50 | 50 | 200 | 50 |
| 1368 | 50 | >200 | >200 | >200 | 6.25 |
| 1369 | >200 | >200 | >200 | >200 | 200 |
| 1370 | >200 | >200 | >200 | >200 | 50 |
| 1398 | 100 | 50 | 100 | >200 | 100 |
| 1399 | 50 | 25 | 25 | 200 | 100 |
| 1411 | 50 | 50 | 50 | 200 | 100 |
| 1412 | 50 | 25 | 25 | 200 | 100 |
| 1413 | 50 | 200 | >200 | >200 | 200 |
| 1419 | 100 | 50 | 100 | 200 | 50 |
| 1420 | 100 | 200 | 100 | 200 | 50 |
| 1421 | 200 | 50 | 200 | 200 | 200 |
| 1422 | 25 | 200 | 50 | 12.5 | 12.5 |
| 1423 | 200 | 25 | 200 | >200 | 200 |
| 1424 | 50 | 50 | 25 | 100 | 100 |
| 1425 | 50 | 12.5 | 100 | 100 | 100 |
| 1439 | 25 | >200 | 12.5 | 50 | 50 |
| 1400 | >200 | >200 | 100 | 100 | 200 |
| 1443 | 50 | 6.25 | 12.5 | 50 | 1.6 |
| 1444 | 100 | 25 | 25 | 50 | 6.25 |
| 1445 | 25 | 12.5 | 12.5 | 25 | 25 |
| 1446 | >200 | 6.25 | 6.25 | 200 | 100 |
| 1447 | >200 | 6.25 | 6.25 | 100 | 100 |
| 1448 | >200 | 25 | 25 | >200 | >200 |
| 1449 | >200 | 200 | 25 | >200 | >200 |
| 1453 | >200 | 25 | 25 | >200 | >200 |
| 1463 | >200 | >200 | >200 | >200 | >200 |
| 1465 | >200 | 12.5 | 12.5 | 100 | 100 |
| 1466 | >200 | 25 | 12.5 | >200 | >200 |
| 1467 | >200 | 50 | 50 | >200 | >200 |
| 1469 | >200 | 100 | 50 | 50 | 50 |
| 1470 | >200 | >200 | >200 | >200 | >200 |
| 1471 | >200 | 12.5 | 50 | >200 | >200 |
| 1477 | NT | NT | NT | >200 | NT |
| 1478 | >200 | 200 | >200 | >200 | >200 |
| 1485 | >200 | 25 | 25 | >200 | >200 |
| 1486 | >200 | 50 | >200 | >200 | >200 |
| 1487 | >200 | 50 | 12.5 | >200 | >200 |
| 1489 | 100 | 12.5 | 12.5 | 100 | >200 |
| 1490 | 100 | 12.5 | 12.5 | 50 | >200 |
| 1491 | 100 | 12.5 | 6.25 | 25 | >200 |
| 1492 | >200 | 50 | 100 | >200 | >200 |
| 1493 | >200 | 50 | 50 | >200 | >200 |
| 1501 | >200 | >200 | >200 | >200 | >200 |
| 1502 | >200 | >200 | >200 | >200 | >200 |
| 1503 | >200 | >200 | >200 | >200 | >200 |
| 1504 | >200 | >200 | >200 | >200 | >200 |
| 1514 | >200 | >200 | >200 | >200 | >200 |
| 1515 | >200 | 12.5 | 6.25 | >200 | >200 |
| 1516 | 50 | 6.25 | 6.25 | 100 | >200 |
| 1517 | 200 | 6.25 | 6.25 | 100 | >200 |
| 1518 | 200 | 6.25 | 12.5 | >200 | >200 |
| 1519 | 100 | 12.5 | 3.1 | 25 | >200 |
| 1520 | 100 | 3.1 | 3.1 | 100 | >200 |
| 1535 | 50 | 1.6 | 0.8 | 3.1 | >200 |
| 1536 | >200 | >200 | 200 | >200 | >200 |
| 1537 | 100 | 3.1 | 3.1 | 25 | >200 |

TABLE 3-continued

Activity Against Gram-positive Bacteria.*

| Comp # | MIC μg/mL | | | | |
|---|---|---|---|---|---|
| | S. aureus | S. pyogenes | S. pneumoniae | E. faecalis | B. anthracis 34F2 |
| 1538 | 100 | 6.25 | 3.1 | 25 | >200 |
| 1539 | 100 | 3.1 | 3.1 | 25 | >200 |
| 1540 | 100 | 6.25 | 6.25 | 25 | >200 |
| 1541 | 100 | 6.25 | 3.1 | 25 | >200 |
| 1542 | 100 | 6.25 | 3.1 | 25 | >200 |
| 1543 | 100 | 6.25 | 3.1 | 12.5 | >200 |
| 1544 | 50 | 12.5 | 6.25 | 100 | >200 |
| Spectinomycin (Spc) | 25 | 25 | 50 | 50 | 25 |
| Streptomycin (Stp) | 0.4 | 25 | 12.5 | 50 | 0.8 |

The complete names of test organisms listed in the table are as follows: *S. aureus* 8325 or strain ATCC 29213 (for 1471-1544); *Strep. pyogenes* ATCC 700294; *Strep. pneumoniae* DAW27 or strain R6 (for 1443-1544); *E. faecalis* ATCC 33186 and *B. anthracis* Sterne 34F2. NT—Not tested

TABLE 4

Activity Against Gram-negative Bacteria.*

| Comp # | MIC μg/mL | | | | | | | | |
|---|---|---|---|---|---|---|---|---|---|
| | B. cepcia | P. mir | P. vul | K. pneu. | A. bau. | P. aer. | S. mal | E. coli K12 | E. coli K12 ΔtolC |
| 1299 | >200 | >200 | >200 | >200 | >200 | >200 | >200 | >200 | 200 |
| 1329 | >200 | >200 | >200 | >200 | >200 | 100 | 200 | 200 | 50 |
| 1351 | >200 | >200 | >200 | 200 | >200 | 200 | 50 | >200 | 50 |
| 1364 | >200 | >200 | >200 | >200 | >200 | >200 | >200 | >200 | 100 |
| 1365 | >200 | >200 | >200 | >200 | >200 | >200 | >200 | >200 | 200 |
| 1366 | >200 | >200 | >200 | >200 | >200 | 50 | 25 | >200 | 12.5 |
| 1367 | >200 | >200 | >200 | >200 | >200 | 100 | >200 | 200 | 50 |
| 1368 | >200 | >200 | >200 | >200 | >200 | >200 | >200 | 100 | >200 |
| 1369 | >200 | >200 | >200 | >200 | >200 | >200 | >200 | >200 | >200 |
| 1370 | >200 | >200 | >200 | >200 | >200 | >200 | >200 | 200 | 100 |
| 1398 | >200 | >200 | >200 | >200 | >200 | 100 | >200 | >200 | 200 |
| 1399 | >200 | >200 | >200 | >200 | >200 | 100 | >200 | >200 | 100 |
| 1411 | >200 | >200 | >200 | >200 | >200 | 100 | >200 | >200 | 200 |
| 1412 | >200 | >200 | >200 | >200 | >200 | 100 | >200 | >200 | 200 |
| 1413 | >200 | >200 | >200 | >200 | >200 | >200 | >200 | 200 | 50 |
| 1419 | >200 | >200 | >200 | >200 | >200 | >200 | >200 | 100 | 25 |
| 1420 | >200 | >200 | >200 | >200 | >200 | 200 | 200 | 100 | 25 |
| 1421 | 50 | >200 | >200 | >200 | 50 | >200 | 12.5 | 200 | 50 |
| 1422 | >200 | >200 | >200 | >200 | >200 | 25 | >200 | 25 | 12.5 |
| 1423 | >200 | >200 | >200 | >200 | >200 | >200 | >200 | 200 | 100 |
| 1424 | >200 | >200 | >200 | >200 | >200 | 200 | >200 | 200 | 50 |
| 1425 | >200 | >200 | >200 | >200 | >200 | 200 | >200 | 200 | 100 |
| 1439 | >200 | >200 | >200 | >200 | >200 | 50 | >200 | 100 | 12.5 |
| 1400 | >200 | >200 | >200 | >200 | >200 | 100 | >200 | >200 | >200 |
| 1443 | >200 | >200 | >200 | 100 | >200 | >200 | >200 | 100 | 200 |
| 1444 | >200 | >200 | >200 | 100 | >200 | >200 | >200 | 100 | 200 |
| 1445 | >200 | >200 | >200 | 100 | >200 | >200 | >200 | 100 | 200 |
| 1446 | >200 | >200 | >200 | 200 | >200 | >200 | >200 | 200 | >200 |
| 1447 | >200 | >200 | >200 | 200 | >200 | >200 | >200 | 200 | >200 |
| 1448 | 200 | >200 | >200 | >200 | >200 | >200 | >200 | >200 | >200 |
| 1449 | >200 | >200 | >200 | >200 | >200 | >200 | >200 | >200 | 100 |
| 1453 | >200 | >200 | >200 | >200 | >200 | >200 | >200 | >200 | 200 |
| 1463 | >200 | >200 | >200 | >200 | >200 | >200 | >200 | >200 | >200 |
| 1465 | >200 | >200 | >200 | >200 | >200 | >200 | >200 | >200 | 12.5 |
| 1466 | >200 | >200 | >200 | >200 | >200 | >200 | >200 | 100 | 50 |
| 1467 | >200 | 200 | >200 | >200 | >200 | >200 | 100 | 200 | 200 |
| 1469 | >200 | >200 | >200 | >200 | >200 | >200 | 25 | >200 | 100 |
| 1470 | >200 | >200 | >200 | >200 | >200 | >200 | >200 | >200 | >200 |
| 1471 | >200 | >200 | >200 | >200 | >200 | >200 | >200 | >200 | 200 |
| 1477 | >200 | >200 | >200 | >200 | >200 | >200 | >200 | 100 | 100 |
| 1478 | >200 | >200 | >200 | >200 | >200 | >200 | >200 | >200 | >200 |
| 1485 | >200 | >200 | >200 | >200 | >200 | >200 | >200 | NT | >200 |
| 1486 | >200 | >200 | >200 | >200 | >200 | >200 | >200 | NT | >200 |
| 1487 | >200 | >200 | >200 | >200 | >200 | >200 | >200 | 200 | 200 |
| 1489 | >200 | >200 | >200 | >200 | >200 | >200 | >200 | 200 | 50 |
| 1490 | >200 | >200 | >200 | >200 | >200 | >200 | >200 | 200 | 12.5 |
| 1491 | >200 | >200 | >200 | >200 | >200 | >200 | >200 | 200 | 12.5 |

TABLE 4-continued

Activity Against Gram-negative Bacteria.*

| Comp # | B. cepcia | P. mir | P. vul | K. pneu. | A. bau. | P. aer. | S. mal | E. coli K12 | E. coli K12 ΔtolC |
|---|---|---|---|---|---|---|---|---|---|
| 1492 | >200 | >200 | >200 | >200 | >200 | >200 | >200 | >200 | 200 |
| 1493 | >200 | >200 | 100 | >200 | >200 | >200 | >200 | 100 | 25 |
| 1501 | >200 | >200 | >200 | >200 | >200 | >200 | >200 | >200 | >200 |
| 1502 | >200 | >200 | >200 | >200 | >200 | >200 | >200 | >200 | >200 |
| 1503 | >200 | >200 | >200 | >200 | >200 | >200 | >200 | >200 | >200 |
| 1504 | >200 | >200 | >200 | >200 | >200 | >200 | >200 | >200 | >200 |
| 1514 | >200 | >200 | >200 | >200 | >200 | >200 | >200 | >200 | >200 |
| 1515 | >200 | >200 | 100 | >200 | >200 | >200 | >200 | >200 | 12.5 |
| 1516 | >200 | >200 | >200 | >200 | >200 | >200 | >200 | >200 | 12.5 |
| 1517 | >200 | >200 | >200 | >200 | >200 | >200 | >200 | >200 | 200 |
| 1518 | >200 | >200 | >200 | >200 | >200 | >200 | >200 | >200 | 50 |
| 1519 | >200 | >200 | >200 | >200 | >200 | >200 | >200 | >200 | 12.5 |
| 1520 | >200 | >200 | >200 | >200 | >200 | >200 | >200 | >200 | 25 |
| 1535 | >200 | >200 | >200 | >200 | >200 | 100 | >200 | 200 | <6.25 |
| 1536 | >200 | >200 | >200 | >200 | >200 | >200 | >200 | >200 | >200 |
| 1537 | >200 | >200 | >200 | >200 | >200 | >200 | >200 | >200 | 12.5 |
| 1538 | >200 | >200 | >200 | >200 | >200 | 200 | >200 | >200 | 25 |
| 1539 | >200 | >200 | >200 | >200 | >200 | >200 | >200 | >200 | 12.5 |
| 1540 | >200 | >200 | >200 | >200 | >200 | 25 | 200 | >200 | 12.5 |
| 1541 | >200 | >200 | >200 | >200 | >200 | 25 | 200 | >200 | 12.5 |
| 1542 | >200 | >200 | >200 | >200 | >200 | >200 | >200 | >200 | 12.5 |
| 1543 | >200 | >200 | >200 | >200 | >200 | >200 | 200 | >200 | <6.25 |
| 1544 | >200 | >200 | >200 | >200 | >200 | >200 | >200 | >200 | 12.5 |
| Spc | >200 | >200 | 50 | 50 | >200 | 100 | >200 | 12.5-50 | 12.5 |
| Stp | >200 | 50 | 1.6 | >200 | >200 | 25 | 3.12 | 0.8 | 1.6 |

*The complete names of test organisms listed in the table are as follows: Burkholderia cepacia ATCC 25416, Proteus mirabilis ATCC 25933, Proteus vulgaris ATCC 33420, Klebsiella pneumoniae ATCC 33495, Acinetobacter baumannii ATCC 19606, Strenotrophomonas maltophilia ATCC 13637, P. aeruginosa PAO1, E. coli K12 and E. coli K12 ΔtolC. NT—Not tested.

As shown in Table 3, some organisms were more susceptible to particular derivatives than others. For example, the compounds 1443, 1444 and 1368 displayed MICs of 1.6, 6.25 and 6.25 μg/mL respectively, against B. anthracis, which represents a 4-16 fold improvement over spectinomycin. Similarly, the compounds 1422, 1535 and 1543 showed 4-16 fold improvement over spectinomycin against E. facecalis. Several compounds showed significant activity against Strep. pneumoniae. For example, 1329, 1446, 1447, 1491, 1515, 1516, 1517, 1519, 1520, 1535, 1537, 1538, 1539, 1540, 1541, 1542, 1543, and 1544 showed 8-62.5 fold improvement in activity against Strep. pneumoniae over spectinomycin.

As shown in Table 4, the E. coli K12 tolC knockout strain that possesses a defective multi-drug efflux pump was more susceptible than parental E. coli K12 to the spectinomycin analogs, whereas the MIC of spectinomycin was not substantially affected. Without being bound to any one theory, this appears suggestive that drug efflux systems and/or cell permeability might account for the relative inactivity of spectinomycin against most bacterial organisms and that the presently disclosed spectinamides differ from spectinomycin in their uptake and efflux into bacterial cells. Further, it was recently reported that spectinomycin is effluxed by M. tuberculosis (see Ramon-Garcia et al., J. Antimicrobial Chemistry, 59(3), 544-547 (2007)), which can in part explain its general lack of activity against TB cells. Therefore, it is believed that the enhanced anti-tubercular activities of compounds 1329, 1443, 1444 and 1445 and their related analogs against other organisms reflect the increased ability of these molecules to penetrate into specific organisms. Additionally, it is also likely that these inhibitors are less susceptible to extrusion by drug efflux mechanisms.

Example 5

Lack of Cross Resistance and Mode of Action Studies

To determine whether the mode of action of spectinamides against M. tuberculosis is consistent with the known information for spectinomycin, spontaneous drug resistant mutants of compound 1329 were selected on agar containing drug at 4, 8 and 16 times their MICs. Mutants exhibiting resistance to 1329 emerged at a frequency of $1.9-3.7\times10^{-6}$, which is comparable to the mutation frequency for isoniazid resistance as was previously determined using the same method. See Hurdle et al., J. Antimicrob. Chemother, 62(5), 1037-1045 (2008). However, this was higher than the mutation frequency for streptomycin-resistant mutants that emerged at $0.7-1.6\times10^{-7}$. In the spirochete Borrelia burgdorferi, spectinomycin resistance also arises at a frequency of $10^{-6}$ in contrast to streptomycin that emerges at $10^{-7}$ and results from mutations at different loci to those conferring spectinomycin resistance. See Criswell et al., Antimicrob. Agents Chemother., 50(2), 445-452 (2006). Without being bound to any one theory, since spectinomycin and streptomycin both target the 16S rRNA, it is plausible that the elevated mutation frequencies observed for 1329 reflect the occurrence of mutations at sites other than within the target, such as in genes controlling the uptake of 1329. However, two stable mutants exhibiting high-level drug resistance to 1329 and spectinomycin (MICs=>200 μg/mL) were examined for cross resistance to streptomycin, kanamycin, and other anti-tubercular antibiotics. See Table 5. None of the mutants were cross resistant to the aminoglycosides streptomycin and kanamycin, capreomycin and the 23S ribosomal inhibitor linezolid. Similarly, spontaneous mutants of streptomycin were highly susceptible to 1329, including the reference strain ATCC 35820 that is resistant to streptomycin due to mutations in ribosomal protein S12. See Nair et al., Mol. Microbiol., 10(3), 521-527 (1993). Importantly, there was no cross resistance between 1329 and the first-line TB drugs for isoniazid, rifampicin and ethambutol. See Table 5. Together, these results demonstrate that 1329 and spectinomycins appear to exhibit a novel mode of action against M. tuberculosis that is unlikely to be affected by mechanisms that confer resistance to other established TB antibiotics including streptomycin and related aminoglycosides.

TABLE 5

Activity of 1329 Compared to Streptomycin.

| Strain | 1329 | Streptomycin |
|---|---|---|
| H37RV | 0.8-1.6 | 0.2 |
| ATCC35822- Inh-resistant | 0.8 | 0.8 |
| ATCC -35820 Stp-Resistant | 0.8 | 6.25 |
| ATCC35837-Emb-Resistant | 0.8 | 0.2 |
| HL-mutant 15* | >200 | 0.8 |
| HL-mutant 14* | >200 | 0.4 |
| Streptomycin-resistant Mutant 1 | 0.8 | 1.6 |
| Streptomycin-resistant Mutant 2 | 1.6 | >200 |
| Streptomycin-resistant Mutant 6 | 0.4 | >200 |

*Strains are also susceptible to Streptomycin, Kanamycin, Capreomycin, Linezolid, Rifampicin, Ethambutol and Isoniazid.

To explore the genetic basis of resistance to 1329 and reasons for the lack of cross resistance with aminoglycosides, molecular genetic analysis was performed on the two high-level mutants of 1329. In non-tuberculosis organisms mutations in helix 34, the binding domain for spectinomycin, is commonly associated with specific resistance to this antibiotic. See Galimand et al., *Antimicrob. Agents Chemother.,* 44(5), 1365-1366 (2000); and O'Connor and Dahlberg, *Current Microbiology,* 45(6), 429-433 (2002). Similarly, mutations within the ribosomal protein S5 (encoded by rpsE) that interacts with the spectinomycin binding domain also confers spectinomycin resistance as a result of conformational changes that alter the binding domain for spectinomycin in the 16S rRNA. To determine if 1329 also binds to helix 34 and whether mutations within the ribosomal protein S5 or the 16S rRNA engender spectinomycin resistance in *M. tuberculosis*, these genes were sequenced in their entirety in both 1329-resistant mutants i.e. HL-14 and 15. No nucleotide changes were detected in the rpsE genes of the two mutants when these were compared to the rpsE derived from their wild type progenitor H37Rv and the reference sequence for rpsE that is denoted by Rv0721 in the H37Rv genome. In contrast, the mutants HL-14 and 15 contained single point transversions in the genes for the 16S rRNA. Whereas a point mutation involving a C1057A nucleotide change conferred resistance in HL-14, the mutant HL-15 contained a mutation of C1184A in its 16S rRNA. The location of these mutations in relation to the spectinomycin binding domain was ascertained using a BLAST sequence analysis and homology modeling of the TB 16S rRNA (constructed from the crystal structure of the *E. coli* ribosome with bound spectinomycin). The tuberculosis and *E. coli* 16S rRNAs were found to be highly homologous, being 80% identical in sequence. Moreover, these sequences were found to be 100% identical within the 10 Å core area surrounding the spectinomycin binding site, further supporting the use of *E. coli* to map the location of our mutations in relation to spectinamide binding for *M. tuberculosis* 16S rRNA.

Mutations at position C1192 or its cross helix partner G1064, within the helix 34, are common sites for spectinomycin resistance in *E. coli* and other organisms. From the primary sequence alignment and structural analysis it was observed that position C1184 in the *M. tuberculosis* ribosome is homologous to position C1192 in *E. coli*. See Galimand et al., *Antimicrob. Agents Chemother.,* 44(5), 1365-1366 (2000); and O'Connor and Dahlberg, *Current Microbiology,* 45(6), 429-433 (2002). These positions both make equivalent direct H-bonding contact with spectinomycin. Thus the mutation in *M. tuberculosis* resulting in an adenine residue at position 1184 removes the H-bonding contact that is vital for stabilizing spectinomycin within the *M. tuberculosis* ribosome. Similarly, position C1057 is homologous to the *E. coli* residue C1066 that also stabilizes spectinomycin through H-bonding interaction. A mutation involving C1066U is reported to confer spectinomycin resistance in *Salmonella enterica Serovar Typhimurium* and *E. coli*, which supports our finding that the equivalent locus (C1057) in *M. tuberculosis* confers high-level resistance to 1329 and spectinomycin. See O'Connor and Dahlberg, *Current Microbiology,* 45(6), 429-433 (2002). Without being bound to any one theory, that mutational resistance to 1329 maps directly in helix 34 of the 16S rRNA of *M. tuberculosis* is believed to be consistent with the reported mode of action for spectinomycin and explains why there is a lack of target mediated cross resistance with streptomycin and other ribosomal inhibitors against *M. tuberculosis*. Indeed, mutations within helix 44 (i.e., the binding site for aminoglycosides) are required for resistance to streptomycin. Mutations in the ribosomal protein S12 and/or within helix 44 do not affect spectinomycin binding to helix 34.

To further probe the macromolecular basis of mycobacterial inhibition by spectinamides, radiolabelling assays for macromolecular protein synthesis were performed on mid-log cells of *M. bovis* BCG, using $H^3$-Leucine (GE Healthcare, Life Sciences, Piscataway, N.J., United States of America). Within 4 hours after the addition of 1329 or 1445 at 10 times their MICs, protein synthesis was inhibited by 50% or more. See FIG. 3. The control antibiotic streptomycin also inhibited protein synthesis. This appears to indicate that the spectinamides act on their ribosomal target in the bacterial cell to inhibit protein synthesis.

In addition to having enhanced cellular uptake or resistance to efflux mechanisms, it is also plausible that 1329 is more potent than spectinomycin at the ribosomal level. The commercially available cell free *E. coli* S30 coupled transcription/translation system (Promega, Madison, Wis., United States of America) that measures the production of luciferase enzyme on *E. coli* ribosomes, and has been previously used in quantifying the antibacterial target level activity for ribosomal inhibitor antibiotics, was used to assay the protein synthesis inhibition by spectinomycins. See Murray et al., *Antimicrob. Agents Chemother.,* 42(4), 947-950 (1998). The concentrations of 1329 and spectinomycin that caused a 50% reduction in the synthesis of luciferase were found to be 0.66 μM and 0.90 μM respectively. See FIG. 4. These results indicate that 1329 is as potent as spectinomycin at the ribosomal level, but that 1329 is better able to penetrate mycobacteria to reach its ribosomal target.

Using the $IC_{50}$ of 1329 as a standard, the relative inhibitory activity of several other compounds was investigated at 0.66 and 6.6 μM (i.e. 1 and 10 times the $IC_{50}$ of 1329). See FIG. 5. The results indicate that the compounds inhibit luciferase protein production on the *E. coli* ribosomes, though at different levels of activity relative to 1329.

Most compounds in the assay were less active than 1329 at 0.66 μM. Compound 1351 was the next most active. However, 1351 has a MIC value of 25 μg/mL, which suggests that this compound has relatively poor permeability and that selective transport into the tuberculosis bacilli plays a major role in the activity of this series. Likewise the 3'-aminoalkyl series compounds 1420, 1422, 1423, 1424 and 1425 all inhibited well in the cell free assay, but have relatively poor anti-tubercular MIC activity compared to 1329, suggesting that they also suffer from poor permeability. Benzamides (1364, 1365, 1370), alkyl substituted compounds (1421, 1369) and the pyrimidine-substituted compound (1439) were less active than 1329 in the protein synthesis assay suggesting that their lower anti-tubercular activity is due to poorer target affinity.

To further compare the target level activities of spectinamides, concentrations that caused 50% reduction ($IC_{50}$) in luciferase synthesis in the *E. coli* transcription/translation assay were determined for several compounds. As shown in Table 6, the $IC_{50}$s of the compounds varied from 0.12-2.63 μg/mL. The compounds 1329, 1443, 1444 and 1445 all exhibited low $IC_{50}$s comparable to spectinomycin and streptomycin, indicating that the uptake of these molecules into bacterial cells is accompanied by potent inhibition of microbial protein synthesis. Compounds 1351 and 1447 also displayed comparably low $IC_{50}$s, but their higher MICs against TB bacilli probably reflect reduced uptake into these cells, as mentioned above. Altogether these results indicate that the presently disclosed spectinamides are highly potent inhibitors of bacterial protein synthesis.

TABLE 6

Concentration of Spectinamides Causing 50% Inhibition of Luciferase Biosynthesis in S30 Assay.

| Compound[1] | $IC_{50}$ (μg/mL) |
|---|---|
| 1299 | 0.97 |
| 1329 | 0.29 |
| 1351 | 0.22 |
| 1366 | 15.3 |
| 1367 | 1.05 |
| 1368 | 1.08 |
| 1370 | 0.89 |
| 1398 | 0.78 |
| 1413 | 1.92 |
| 1424 | 0.80 |
| 1439 | 2.63 |
| 1443 | 0.29 |
| 1444 | 0.12 |
| 1445 | 0.25 |
| 1446 | 0.68 |
| 1447 | 0.22 |
| 1448 | 2.41 |
| 1453 | 1.04 |
| 1463 | 6.34 |
| 1465 | 0.50 |
| 1466 | 0.57 |
| 1471 | 0.17 |
| Spectinomycin | 0.32 |
| Streptomycin | 0.27 |

[1]Compounds with MIC anti-tubercular activity of ≤6.25 μg/mL and $IC_{50}$s for luciferase biosynthesis of ≤0.57 μg/mL are shown in bold.

From these results it appears that the structural activity relationship of spectinomycins against *M. tuberculosis* and possibly other organisms is mediated by (i) the extent of their cellular uptake to reach their ribosomal drug target and (ii) the ability for molecules to interact with key residues within the spectinomycin binding domain. The high activity of 1329, 1443 and 1445 appear to come from both high target affinity and good cellular uptake:

Example 6

Combination with Other Antibiotics

In some embodiments, it can be efficacious to use anti-tuberculosis drugs in combination. Standard chequerboard assays were performed to evaluate whether 1329, 1443, or 1445 combined with front-line anti-tubercular drugs could exhibit enhanced activity against *M. tuberculosis*. Fractional inhibitory concentration (FIC) indices between 0.5 and 4 suggest additive effects. See Odds, F. C., *J. Antimicrob. Chemother.* 52, 1 (2003). Thus, the results shown in Table 7 indicate that combinations of isoniazid, ethambutol or rifampin with 1329 exhibited additive effects. Therefore, the presently disclosed spectinomycins would most likely be suitable for combination therapy with other anti-tuberculosis drugs.

TABLE 7

Effects of Combination Therapies

| Combination | FIC ranges |
|---|---|
| 1329 + Rifampicin | 1-1.25 |
| 1329 + Isoniazid | 1-1.5 |
| 1329 + Ethambutol | 1-1.5 |
| Streptomycin + Rifampicin | 0.62 |
| Streptomycin + Isoniazid | 0.62 |
| Streptomycin + Ethambutol | 1 |

Example 7

Pharmacokinetic Data and in Vivo Activity

For all antimicrobial drug candidates it is important to assess the toxicity of lead compounds to ensure they have selective killing of the target pathogen over host cells. Thus, the cytotoxicity of 1329 was assessed against VERO epithelial cells using a well validated colorimetric MTT based cell proliferation. See Hurdle et al., *J. Antimicrob. Chemother,* 62(5), 1037-1045 (2008). The mean cytotoxic $IC_{50}$ for spectinomycin, 1329, streptomycin, and ethambutol were 1030, 2182.4, 1536.1, and 731.6, respectively. The therapeutic indices obtained as the $IC_{50}$ divided by the MIC were 41.5, 5456, 7680.5, and 913.8 respectively, which indicates that 1329, like streptomycin and ethambutol, is highly selective for the killing of *M. tuberculosis*. The poor index of unmodified spectinomycin reflects its poor activity against TB bacilli. To determine whether lack of cytotoxicity resulted from poor binding to the mammalian ribosomes, compounds were assayed fro ability to inhibit mammalian protein synthesis in Rabbit Reticulocytes (Promega, Madison, Wis., United States of America). The $IC_{50}$, of compounds 1329, 1443, and 1445 were greater than the highest concentration tested (i.e., >512 μg/mL). This indicates the compounds are highly selective for bacterial ribosomes as shown in Table 6.

A preliminary pharmacokinetic profile was determined for 1329 (i.e., Lee 1329) using previously described methods. See Budha et al., *The AAPS Journal,* 10(1), 157-165 (2008); and Budha et al., *Curr. Med. Chem.,* 15(8), 809-825 (2008).

Following intravenous administration of 10 mg/kg in rats, 1329 follows a bi-exponential concentration/time profile with distinct distribution and elimination phases. See FIG. 6. Plasma protein binding of the compound is approximately 30%. 1329 is widely distributed with a steady state volume of distribution of 4.3 L/kg. It has a mean residence time in the body of approximately 5.3 hours. In vitro experiments using hepatic microsomes suggest that 1329 is metabolically stable with 95% of parent drug remaining intact after 90 min of incubation.

Following intravenous administration in rats, 1329 has a mean systemic clearance of 0.8 L/hr/kg. The fraction of dose excreted unchanged by the kidneys is 0.46, with approx. 40% of the dose being eliminated unchanged in the first 6 hours. The excretion ratio (ratio of renal clearance to glomerular filtration rate) of 1329 is 1.7 indicating filtration and active secretion as the net urinary elimination processes. The hepatic extraction ratio of the molecule is 0.13 indicating that 1329 can be classified as a low hepatic extraction drug.

It will be understood that various details of the presently disclosed subject matter may be changed without departing from the scope of the presently disclosed subject matter. Furthermore, the foregoing description is for the purpose of illustration only, and not for the purpose of limitation.

What is claimed is:

1. A compound of Formula (I):

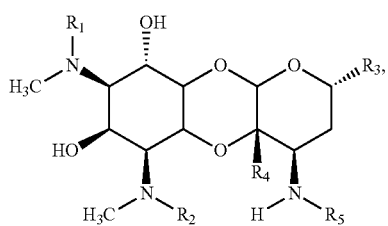

(I)

wherein:
$R_1$ and $R_2$ are each independently H, alkoxycarbonyl, or aralkoxycarbonyl;
$R_3$ is alkyl;
$R_4$ is H, hydroxy, alkyl, or alkoxy; and
$R_5$ is —C(=O)$R_6$, wherein $R_6$ is:
(a) selected from the group consisting of —CH$_2$NHC(CH$_3$)$_3$, —CH(NH$_2$)CH(CH$_3$)CH$_2$CH$_3$, —CH(NH$_2$)CH(CH$_3$)$_2$, —CH(CH$_2$C$_6$H$_5$)NHC(=O)CH$_2$NH$_2$, —CH$_2$CH$_2$NHC(=O)C$_6$H$_5$, and —CH$_2$CH$_2$NHC(=O)CH$_2$C$_6$H$_5$; or
(b) selected from the group consisting of heteroaryl, substituted heteroaryl, 2-substituted phenyl, 4-halo-substituted phenyl, —CH₂R₇, and —C(R₈)₂; wherein R₇ is selected from the group consisting of aralkyl, substituted aralkyl, heteroaryl, substituted heteroaryl, and substituted phenyl, wherein said substituted phenyl is selected from the group consisting of fluoro-substituted phenyl, alkyl-substituted phenyl, 2-substituted phenyl, 3-monosubstituted phenyl, 2,3-di-substituted phenyl, and di-substituted phenyl wherein two phenyl carbons are together substituted with an alkylene; and each R₈ is independently aryl or substituted aryl; and wherein said heteroaryl and said substituted heteroaryl are selected from the group consisting of pyridyl, pyrimidinyl, pyridazinyl, oxazolyl, furanyl, triazolyl, triazinyl, benzofuranyl, pyrrolyl, imidazoyl, pyrazole, thiazolyl, quinolinyl, isoquinolinyl, benzoxazolyl, and benzothiazolyl, or a pharmaceutically acceptable salt thereof.

2. The compound of claim 1, wherein R₁ and R₂ are each H.

3. The compound of claim 1, wherein R₁ and R₂ are each aralkoxycarbonyl selected from the group consisting of benzyloxycarbonyl and benzyloxycarbonyl substituted by one or more halo, alkoxy, and nitro groups.

4. The compound of claim 3, wherein R₁ and R₂ are each benzyloxycarbonyl.

5. The compound of claim 1, wherein R₃ is methyl or butyl.

6. The compound of claim 1, wherein R₄ is H, OH, methyl, or methoxy.

7. The compound of claim 1, wherein R₆ is 4-fluorophenyl or 2-fluorophenyl.

8. The compound of claim 1, wherein R₆ is —C(R₈)₂, wherein each R₈ is phenyl or substituted phenyl.

9. The compound of claim 1, wherein the compound of Formula (I) is a compound of Formula (Ia):

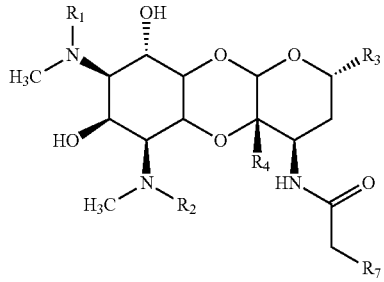

(Ia)

wherein:
R₁ and R₂ are each independently H, alkoxycarbonyl, or aralkoxycarbonyl;
R₃ is alkyl;
R₄ is H, hydroxy, alkyl, or alkoxy; and
R₇ is selected from the group consisting of aralkyl, substituted aralkyl, heteroaryl, substituted heteroaryl, and substituted phenyl, wherein said substituted phenyl is selected from the group consisting of fluoro-substituted phenyl, alkyl-substituted phenyl, 2-substituted phenyl, 3-mono-substituted phenyl, 2,3-di-substituted phenyl, and di-substituted phenyl wherein two phenyl carbons are together substituted with an alkylene; and wherein said heteroaryl and said substituted heteroaryl are selected from the group consisting of pyridyl, triazolyl, triazinyl, pyrimidinyl, pyridazinyl, oxazolyl, furanyl, benzofuranyl, thiophenyl, pyrrolyl, imidazoyl, thiazolyl, quinolinyl, isoquinolinyl, benzoxazolyl, and benzothiazolyl, or a pharmaceutically acceptable salt thereof.

10. The compound of claim 9, wherein R₇ is substituted phenyl selected from the group consisting of 4-fluorophenyl, 4-methylphenyl, 3-methylphenyl, 3-methoxyphenyl, 2-methoxyphenyl, 3,4-methylenedioxyphenyl, and 2,3-difluorophenyl.

11. The compound of claim 9, wherein the heteroaryl group of R₇ is substituted heteroaryl, wherein the heteroaryl is substituted with one or more of the group consisting of NH₂, OH, alkylamino, arylamino, nitro, halo, alkyl, substituted alkyl, alkoxy, perhaloalkoxy, aralkyl, acyl, aryl, aryloxy, and substituted aryl.

12. The compound of claim 11, wherein the heteroaryl group of R₇ is substituted heteroaryl, wherein the heteroaryl is substituted with one or more of the group consisting of fluoro, chloro, bromo, methoxy, methyl, nitro, trifluoromethoxy, phenylamino, phenyl, and trifluoromethyl.

13. The compound of claim 9, wherein R₇ is aralkyl or substituted aralkyl, wherein said aralkyl or substituted aralkyl comprises a heteroaryl or substituted heteroaryl group.

14. The compound of claim 9, wherein the heteroaryl group of R₇ comprises a nitrogen-containing heteroaryl group and the compound of Formula (Ia) has a structure of one of Formulas (Ib), (Ic), or (Id):

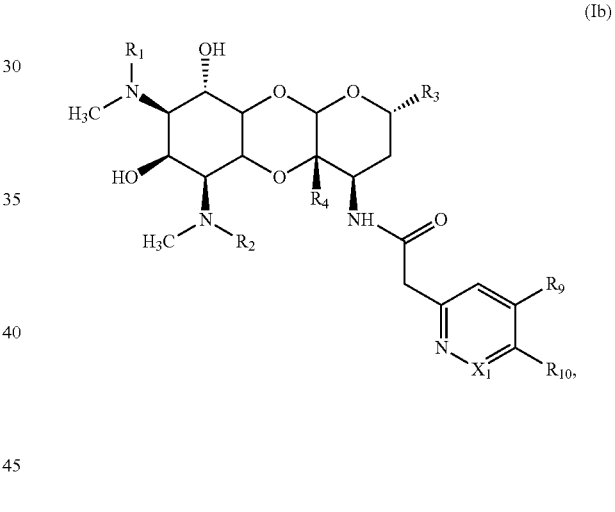

(Ib)

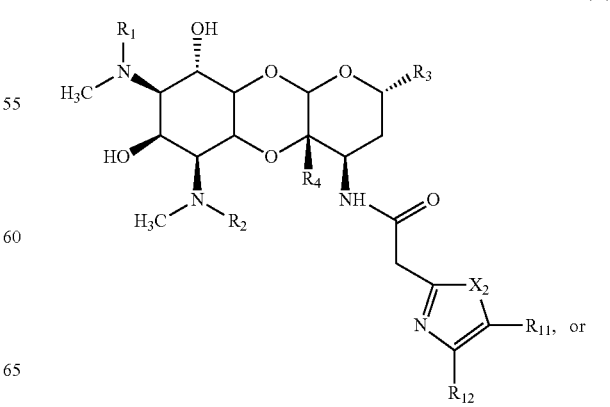

(Ic)

-continued

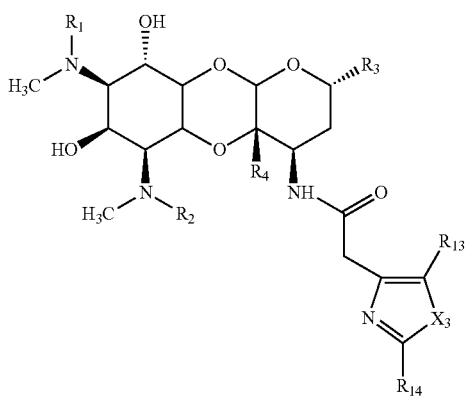

(Id)

wherein:
R$_1$ and R$_2$ are each independently H, alkoxycarbonyl, or aralkoxycarbonyl;
R$_3$ is alkyl;
R$_4$ is H, hydroxy, alkyl, or alkoxy;
X$_1$ is CH or N;
X$_2$ and X$_3$ are each O, S, or NH;
R$_9$, R$_{10}$, R$_{11}$, R$_{12}$, R$_{13}$, and R$_{14}$ are independently selected from the group consisting of H, halo, hydroxy, nitro, N(R$_{15}$)$_2$, alkyl, substituted alkyl, alkoxy, perhaloalkoxy, aralkyl, substituted aralkyl, aralkoxy, aryl, aryloxy, acyl and substituted aryl;
or wherein R$_9$ and R$_{10}$ together or R$_{11}$ and R$_{12}$ together are alkylene; and
each R$_{15}$ is independently selected from the group consisting of H, alkyl, substituted alkyl, aralkyl, substituted aralkyl, aryl, and substituted aryl;
or a pharmaceutically acceptable salt thereof.

15. The compound of claim 1, wherein the compound is selected from the group consisting of:
3'-dihydro-3'-deoxy-4(R)-(3-pyridin-3-yl)propionylamino spectinomycin;
3'-dihydro-3'-deoxy-4(R)-(pyridin-2-yl)acetylamino spectinomycin;
3'-dihydro-3'-deoxy-4(R)-4-fluorobenzoylamino spectinomycin;
3'-dihydro-3'-deoxy-4(R)-furan-2-carboxylicamino spectinomycin;
3'-dihydro-3'-deoxy-4(R)-(4-fluorophenyl)acetylamino spectinomycin;
3'-dihydro-3'-deoxy-4(R)-(pyridin-3-yl)acetylamino spectinomycin;
3'-dihydro-3'-deoxy-4(R)-pyridin-2-carboxylicamino spectinomycin;
3'-dihydro-3'-deoxy-4(R)-p-tolylacetylamino spectinomycin;
3'-dihydro-3'-deoxy-4(R)-(3-methoxy-phenyl)acetylamino spectinomycin;
3'-dihydro-3'-deoxy-4(R)-[3,4-(methylene dioxy)phenyl]acetylamino spectinomycin;
3'-dihydro-3'-deoxy-4(R)-m-tolylacetylamino spectinomycin;
3'-dihydro-3'-deoxy-4(R)-(pyridin-4-yl)acetylamino spectinomycin;
3'-dihydro-3'-deoxy-4(R)-(pyrimidin-2-yl)acetylamino spectinomycin;
3'-dihydro-3'-deoxy-4(R)-(thiazol-4-yl)acetylamino spectinomycin;
3'-dihydro-3'-deoxy-4(R)-(2-aminothiazol-4-yl)acetylamino spectino-mycin;
3'-dihydro-3'-deoxy-4(R)-(5-fluoropyridin-2-yl)acetylamino spectinomycin;
3'-dihydro-3'-deoxy-4(R)-(2,3-difluorophenyl)acetylamino spectinomycin;
3'-dihydro-3'-deoxy-4(R)-(2-methoxyphenyl)acetylamino spectinomycin;
3'-dihydro-3'-deoxy-4(R)-(pyridazin-3-yl)acetylamino spectinomycin;
3'-dihydro-3'-deoxy-4(R)-(pyrazine-2-yl)carboxylicamino spectinomycin;
3'-dihydro-3'-deoxy-4(R)-(benzooxazol-2-yl)acetylamino spectinomycin;
3'-dihydro-3'-deoxy-4(R)-(1H-imidazol-4-yl)acetylamino spectinomycin;
3'-dihydro-3'-deoxy-4(R)-[3(R)-amino-3-(4-fluorophenyl)]propanoylamino spectinomycin;
3'-dihydro-3'-deoxy-4(R)-(thiazol-2-yl)acetylamino spectinomycin;
3'-dihydro-3'-deoxy-4(R)-(5-nitropyridin-2-yl)acetylamino spectinomycin;
3'-dihydro-3'-deoxy-4(R)-(benzothiazol-2-yl)acetylamino spectinomycin;
3'-dihydro-3'-deoxy-4(R)-(2-fluorobenzene-1-yl)carboxylicamino spectinomycin;
3'-dihydro-3'-deoxy-4(R)-(2,2-diphenyl)acetylamino spectinomycin;
3'-dihydro-3'-deoxy-4(R)-(5-bromopyridin-2-yl)acetylamino spectino-mycin;
3'-dihydro-3'-deoxy-4(R)-(2-phenylthiazol-4-yl)acetylamino spectino-mycin;
3'-dihydro-3'-deoxy-4(R)-(pyridin-2-yl)propanoylamino spectinomycin;
3'-dihydro-3'-deoxy-4(R)-(5-phenylpyridin-2-yl)acetylamino spectino-mycin;
3'-dihydro-3'-deoxy-4(R)-(2-(phenylamino)thiazol-4-yl)acetylamino spectinomycin;
3'-Dihydro-3'-deoxy-4(R)-(5-(4-chlorophenyl)pyridin-2-yl)acetylamino spectinomycin;
3'-Dihydro-3'-deoxy-4(R)-(quinoline-8-yl)carbonylamino spectinomycin;
3'-Dihydro-3'-deoxy-4(R)-2-(1-benzyl-1H-1,2,3-triazol-4-yl)acetylamino spectinomycin;
3'-Dihydro-3'-deoxy-4(R)-(2-((4-fluorophenyl)amino)thiazol-4-yl)acetylamino spectinomycin;
3'-Dihydro-3'-deoxy-4(R)-(2-((3-fluorophenyl)amino)thiazol-4-yl)acetylamino spectinomycin;
3'-Dihydro-3'-deoxy-4(R)-(2-((4-(trifluoromethoxy)phenyl)amino)thiazol-4-yl)acetylamino spectinomycin;
3'-Dihydro-3'-deoxy-4(R)-(2-((4-(trifluoromethyl)phenyl)amino)thiazol-4-yl)acetylamino spectinomycin;
3'-Dihydro-3'-deoxy-4(R)-(5-(4-fluorophenyl)pyridin-2-yl)acetylamino spectinomycin;
3'-Dihydro-3'-deoxy-4(R)-(5-(3-methoxyphenyl)pyridin-2-yl)acetylamino spectinomycin;
3'-Dihydro-3'-deoxy-4(R)-(4-chloropyridin-2-yl)acetylamino spectino-mycin;
3'-dihydro-3'-deoxy-4(R)-(tert-butylamino)acetylamino spectinomycin;
3'-dihydro-3'-deoxy-4(R)-(3-methyl)butanoylamino spectinomycin;
3'-dihydro-3'-deoxy-4(R)-[(2S,3S)-2-amino-3-methyl]pentanoylamino spectinomycin;
3'-dihydro-3'-deoxy-4(R)-[2(S)-amino-3-methyl]butanoylamino spectino-mycin;

3'-dihydro-3'-deoxy-4(R)-[2(S)-(2-aminoacetamido)-3-phenyl]propanoyl-amino spectinomycin;

3'-dihydro-3'-deoxy-4(R)-3-benzamido propanoylamino spectinomycin; and

3'-dihydro-3'-deoxy-4(R)-3-(2-phenylacetamido)propanoylamino spectinomycin;

or a pharmaceutically acceptable salt thereof.

16. The compound of claim 1, wherein the compound is a pharmaceutically acceptable salt.

17. The compound of claim 16, wherein the compound is a hydrochloride or hydrobromide salt.

18. A pharmaceutical formulation comprising:
(a) a compound of claim 1; and
(b) a pharmaceutically acceptable carrier.

19. The pharmaceutical formulation of claim 18, wherein the pharmaceutically acceptable carrier is pharmaceutically acceptable in humans.

20. The pharmaceutical formulation of claim 18, further comprising an additional antibacterial compound.

21. The pharmaceutical formulation of claim 20, wherein the additional antibacterial compound is an anti-tuberculosis compound.

22. The pharmaceutical formulation of claim 20, wherein the additional antibacterial compound is selected from the group consisting of isoniazid, ethambutol, rifampicin, kanamycin, capreomycin, linezolid, and streptomycin.

23. The pharmaceutical formulation of claim 18, wherein the formulation is for oral or topical administration.

24. A compound selected from the group consisting of:

3'-dihydro-3'-deoxy-4(R)-cyclopropylmethylamino spectinomycin;

3'-dihydro-3'-deoxy-4(R)-furan-2-yl-methylamino spectinomycin;

3'-dihydro-3'-deoxy-4(R)-(3-methoxy)benzylamino spectinomycin;

3'-dihydro-3'-deoxy-4(R)-(4-fluoro)benzylamino spectinomycin; and

3'-dihydro-3'-deoxy-4(R)-2-phenylethylamino spectinomycin;

or a pharmaceutically acceptable salt thereof.

* * * * *